(12) United States Patent
Brown et al.

(10) Patent No.: US 9,833,429 B2
(45) Date of Patent: *Dec. 5, 2017

(54) THERAPEUTIC COMPOSITIONS

(71) Applicant: LEO Laboratories Limited, Dublin (IE)

(72) Inventors: Marc Barry Brown, Watford (GB); Michael Edward Donald Crothers, Hillsborough (GB); Tahir Nazir, Middlesex (GB)

(73) Assignee: LEO Laboratories Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 15/163,295

(22) Filed: May 24, 2016

(65) Prior Publication Data
US 2016/0263069 A1    Sep. 15, 2016

Related U.S. Application Data

(63) Continuation of application No. 14/269,055, filed on May 2, 2014, which is a continuation of application No. 13/769,809, filed on Feb. 18, 2013, now Pat. No. 8,716,271, which is a continuation of application No. 13/563,698, filed on Jul. 31, 2012, now Pat. No. 8,377,919, which is a continuation of application No. 12/097,258, filed as application No. PCT/GB2006/004739 on Dec. 18, 2006, now Pat. No. 8,278,292.

(30) Foreign Application Priority Data

Dec. 16, 2005 (GB) .................. 0525680.5

(51) Int. Cl.
| | | |
|---|---|---|
| A61K 31/25 | (2006.01) | |
| A61P 35/00 | (2006.01) | |
| A61K 31/22 | (2006.01) | |
| A61K 9/00 | (2006.01) | |
| A61K 9/06 | (2006.01) | |
| A61K 47/10 | (2017.01) | |
| A61K 47/12 | (2006.01) | |
| A61K 47/32 | (2006.01) | |
| A61K 31/215 | (2006.01) | |
| A61K 47/38 | (2006.01) | |
| A61K 36/47 | (2006.01) | |

(52) U.S. Cl.
CPC .......... *A61K 31/22* (2013.01); *A61K 9/0014* (2013.01); *A61K 9/06* (2013.01); *A61K 31/215* (2013.01); *A61K 36/47* (2013.01); *A61K 47/10* (2013.01); *A61K 47/12* (2013.01); *A61K 47/32* (2013.01); *A61K 47/38* (2013.01)

(58) Field of Classification Search
USPC ........................................................ 514/183
See application file for complete search history.

(56) References Cited

U.S. PATENT DOCUMENTS

| | | |
|---|---|---|
| 5,720,963 A | 2/1998 | Smith |
| 6,432,452 B1 | 8/2002 | Aylward |
| 7,378,445 B2 | 5/2008 | Aylward et al. |
| 8,278,292 B2 | 10/2012 | Brown et al. |
| 8,372,827 B2 | 2/2013 | Brown et al. |
| 8,372,828 B2 | 2/2013 | Brown et al. |
| 8,377,919 B2 | 2/2013 | Brown et al. |
| 8,536,163 B2 | 9/2013 | Brown et al. |
| 8,716,271 B2 | 5/2014 | Brown et al. |
| 8,735,375 B2 | 5/2014 | Brown et al. |
| 8,901,356 B2 | 12/2014 | Hogberg et al. |
| 9,314,458 B2 | 4/2016 | Aylward et al. |
| 9,416,084 B2 | 8/2016 | Hogberg et al. |
| 9,676,698 B2 | 6/2017 | Hogberg et al. |
| 2003/0191179 A1 | 10/2003 | Joshi-Hangal et al. |
| 2004/0131665 A1 | 7/2004 | Wepfer |

FOREIGN PATENT DOCUMENTS

| | | |
|---|---|---|
| EP | 0330094 A1 | 2/1989 |
| EP | 1466594 B1 | 12/2008 |
| EP | 2399571 A1 | 12/2011 |
| EP | 1988877 B1 | 2/2014 |
| GB | 20050025680 | 12/2005 |
| JP | 2005-521657 | 7/2005 |
| WO | WO-96/07396 | 3/1996 |
| WO | WO 2002/11743 A2 | 2/2002 |
| WO | WO 2004/045634 | 6/2004 |
| WO | WO 2005/000289 | 1/2005 |
| WO | WO-2006/063382 | 6/2006 |
| WO | WO-2007/053912 | 5/2007 |
| WO | WO 2007/068963 | 6/2007 |

OTHER PUBLICATIONS

Statutory Declaration of Professor Peter Hersey, dated Dec. 9, 2013, in the matter of Australian Patent Application No. 2006325255 to Leo Laboratories Limited and Opposition thereto by Sandoz AG (140 pages).
Statutory Declaration of Kieran Williams, dated Dec. 10, 2013, in the matter of Australian Patent Application No. 2006325255 to Leo Laboratories Limited and Opposition thereto by Sandoz AG (130 pages).
Declaration of Marco Fachini, dated Dec. 19, 2013, in the matter of Australian Patent Application No. 2006325255 to Leo Laboratories Limited and Opposition thereto by Sandoz AG (81 pages).
Declaration of Emma-Louise Moore, dated Dec. 19, 2013, in the matter of Australian Patent Application No. 2006325255 to Leo Laboratories Limited and Opposition thereto by Sandoz AG (11 pages).
Declaration of Associate Professor Roberta Cavalli, dated Dec. 20, 2013, in the matter of Australian Patent Application No. 2006325255 to Leo Laboratories Limited and Opposition thereto by Sandoz AG (28 pages).
Declaration of Professor Giovanni Appendino, dated Dec. 20, 2013, in the matter of Australian Patent Application No. 2006325255 to Leo Laboratories Limited and Opposition thereto by Sandoz AG (293 pages).
Statutory Declaration of Peter Gordon Parsons, dated Apr. 1, 2014, in the matter of Australian Patent Application No. 2006325255 to Leo Laboratories Limited and Opposition thereto by Sandoz AG (14 pages).

(Continued)

*Primary Examiner* — Kathrien Cruz
(74) *Attorney, Agent, or Firm* — Fish & Richardson P.C.

(57) ABSTRACT

Ingenol angelate is a potent anticancer agent, and can be stabilized by dissolving it in an aprotic solvent in the presence of an acidic buffer.

24 Claims, 6 Drawing Sheets

(56) References Cited

OTHER PUBLICATIONS

Figure 1:
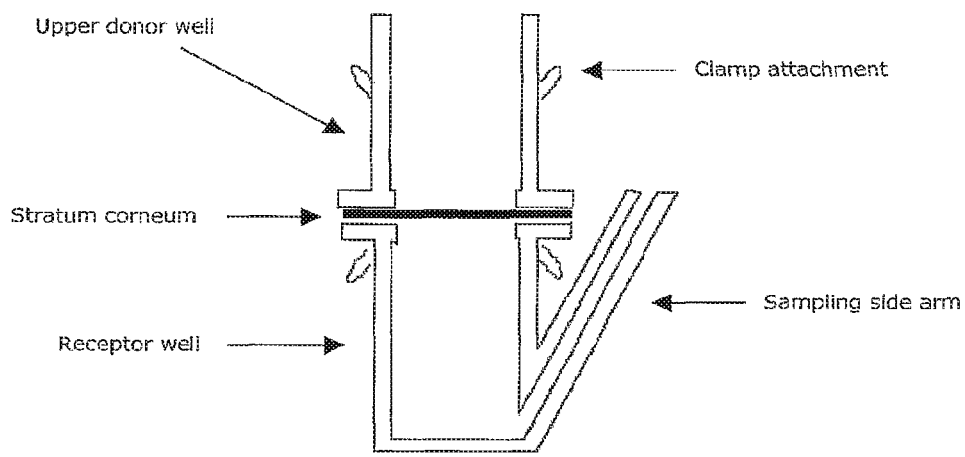

Declaration of Dr. Per-Ola Christian Arvidsson dated Apr. 11, 2014, in the matter of Australian Patent Application No. 2006325255 to Leo Laboratories Limited and Opposition thereto by Sandoz AG (129 pages).

Statutory Declaration of Doctor Jacqueline Waterkeyn, dated Apr. 11, 2014, in the matter of Australian Patent Application No. 2006325255 to Leo Laboratories Limited and Opposition thereto by Sandoz AG (32 pages).

Declaration of Dr. Michael Edward Donald Crothers, dated Apr. 30, 2014, in the matter of Australian Patent Application No. 2006325255 to Leo Laboratories Limited and Opposition thereto by Sandoz AG (18 pages).

Statutory Declaration of Carol Margaret Burnton dated May 5, 2014, in the matter of Australian Patent Application No. 2006325255 to Leo Laboratories Limited and Opposition thereto by Sandoz AG (180 pages).

Statutory Declaration of Philip Andrew Marshall, dated Jul. 1, 2014, in the matter of Australian Patent Application No. 2006325255 to Leo Laboratories Limited and Opposition thereto by Sandoz AG (1077 pages).

Second Declaration of Associate Professor Roberta Cavalli, dated Oct. 10, 2014, in the matter of Australian Patent Application No. 2006325255 to Leo Laboratories Limited and Opposition thereto by Sandoz AG (32 pages).

Second Declaration of Emma-Louise Moore, dated Oct. 29, 2014, in the matter of Australian Patent Application No. 2006325255 to Leo Laboratories Limited and Opposition thereto by Sandoz AG (13 pages).

Second Statutory Declaration of Kieran Williams, dated Oct. 30, 2014, in the matter of Australian Patent Application No. 2006325255 to Leo Laboratories Limited and Opposition thereto by Sandoz AG (114 pages).

Second Declaration of Professor Giovanni Appendino, dated Oct. 30, 2014, in the matter of Australian Patent Application No. 2006325255 to Leo Laboratories Limited and Opposition thereto by Sandoz AG (79 pages).

Opponent's Outline of Submissions, dated May 9, 2015, in the matter of Australian Patent Application No. 2006325255 to Leo Laboratories Limited and Opposition thereto by Sandoz AG (54 pages).

Applicant's Outline of Submissions, dated May 18, 2015, in the matter of Australian Patent Application No. 2006325255 to Leo Laboratories Limited and Opposition thereto by Sandoz AG (91 pages).

Ogbourne et al., "Antitumor activity of 3-ingenyl angelate: Plasma membrane and mitochondrial disruption and necrotic cell death", Cancer Research, 64(15):2833-2839 (2004).

Gillespie et al., "Ingenol 3-angelate induces dual modes of cell death and differentially regulates tumor necrosis factor-related apoptosis-inducing ligand-induced apoptosis in melanoma cells", Molecular Cancer Therapeutics, 3(12):1651-1658 (2004).

International Search Report for corresponding PCT Patent Application No. PCT/GB2006/004739, dated Sep. 4, 2007.

Gruijl, "Skin Cancer and Solar UV Radiation", European Journal of Cancer, vol. 35, No. 14, pp. 2003-2009 (1999).

US National Institutes of Health Clinical Trials.gov Archive NCT00107965 dated Dec. 8, 2005 (http://clinicaltrials.gov/archive/NCT00107965/2005_12_08).

US National Institutes of Health Clinical Trials.gov Archive NCT00108121 dated Dec. 8, 2005 (http://clinicaltrials.gov/archive/NCT00108121/2005_12_08).

US National Institutes of Health Clinical Trials.gov Archive NCT00239134 dated Dec. 8, 2005 (http://clinicaltrials.gov/archive/NCT00108134/2005_12_08).

Hampson et al., "Treatment of actinic keratoses acute myeloid leukemia therapy treatment of basal cell carcinoma protein kinase C activator", Drugs of the Future 30:1003-1005 (2005).

Lin et al., "The dermatitis-producing constituents of Euphorbia hermentiana latex", Journal of Natural Products, 46:723-731 (1983).

Sorg et al., "On the Chemistry of Ingenol, II [I] Esters of Ingenol and $\Delta^{7,8}$ Isoingenol", Z. Naturforsch, 37b:748-756 (1982).

Statement of Grounds and Particulars (Opposition) filed Sep. 30, 2013, in corresponding Australian Patent Application No. 2006325244.

Declaration of Emma-Louise Moore (including exhibits) filed Dec. 23, 2013, in Opposition Proceedings in corresponding Australian Patent Application No. 2006325244.

Declaration of Peter Hersey (including exhibits) filed Dec. 23, 2013, in Opposition Proceedings in corresponding Australian Patent Application No. 2006325244.

Declaration of Roberta Cavalli (including exhibits) filed Dec. 23, 2013, in Opposition Proceedings in corresponding Australian Patent Application No. 2006325244.

Declaration of Marco Fachini (including exhibits) filed Dec. 23, 2013, in Opposition Proceedings in corresponding Australian Patent Application No. 2006325244.

Declaration of Kieran Williams (including exhibits) filed Dec. 23, 2013, in Opposition Proceedings in corresponding Australian Patent Application No. 2006325244.

Declaration of Giovanni Appendino (including exhibits) filed Dec. 23, 2013, in Opposition Proceedings in corresponding Australian Patent Application No. 2006325244.

"3-Day Repeat Dose Dermal Tolerance/Irritation Study Comparing Ingenol-3-Anglate Formulations of Varying pH in Rats" D28 (3 pages) [Aug. 26, 2015].

"A Multi-Center, Open-Label Study to Evaluate the Safety and Efficacy of PEP005 (Ingenol Mebutate) Gel, 0. 05% in Patients with Actinic Keratoses on Non-Head Locations (Trunk and Extremities)", PEP005-020 Study Description on ClinicalTrials.gov Sep. 2009 (4 pages).

"Cancer Success", The Advertiser AU newspaper, Nov. 29, 2005 (2 pages).

"Danish Focus: Cancer, CNS, Metabolic, Inflammatory and Infectious Diseases", Life Science Clusters, (Spring 2010), 17-20.

"Peplin Results for the Quarter Ended Dec. 31, 2008", Business Wire, Feb. 17, 2009, available at http://www.businesswire.com/news/home/20090217006536/en/Peplin-Results-Quarter-Ended-31-December-2008.

"Phase III Region-I Study Shows PEP005 (Ingenol Mebutate) Gel 0.05% May Reduce Pre-Cancerous Skin Lesions in Patients with Actinic Keratosis", Data presented at the 68th Annual Meeting of the American Academy of Dermatology (Mar. 5, 2010).

"Positive Results for Leo Pharma's Phase Ill Actinic Keratosis Trials on the Face and Scalp", announcement, Dec. 21, 2009.

Abo and Evans, "Ingenol Esters from the Pro-inflammatory Fraction of Euphorbia Kamerunica", Phytochemistry, 21(3):725-726 (1982).

Adolf et al., *3-0-Angeloylingenol, the Toxic and Skin Irritant Factor from Latex of Euphorbia Anitiquorum L. (Euphorbiaceae) and from a Derived Thai Purgative and Anthelimintic (Vermifuge) drug*, J. Sci. Soc. Thailand, 9.81-88 (1983).

Ajikumar, "Terpenoids: Opportunities for Biosynthesis of Natural Product Drugs Using Engineered Microorganisms", Molecular Pharmaceutics, 5(2):167-190 (2008).

Aldridge, "Folk Lore Medicine: A Highly Relevant Approach to Drug Discovery", Clin Exp Pharmacol Physiol, 31(11):A216 (2004).

Alonso-Castro, "Mexican Medicinal Plants Used for Cancer Treatment: Pharmacological, Phytochemical and Ethnobotanical Studies", Journal of Ethnopharmacology, 133(3):945-972 (2011).

Alphora, "Ingenol 3-Angelate Formulation Stability Studies", Alphora Research Inc., Project: ZOY, Alphos Code: C214, Report # AS-13-0514-R, pp. 1-8 (Dec. 17, 2013).

Amini, "Nonsurgical Innovations in the Treatment of Nonmelanoma Skin Cancer", J Clin Aesthetic Dermatol 3(6):20-34 (2010).

Anderson, "Early Phase Clinical Development of PEP005 Topical Gel for Actinic Keratoses", Poster presented at the 21st World Congress of Dermatology, Oct. 1-5, 2007, P5702.

(56) References Cited

OTHER PUBLICATIONS

Anderson, "Efficacy and Tolerability of Ingenol Mebutate (PEP005) Gel, 0.025% and 0. 05%, for Scalp and Non-scalp Actinic Keratosis", Summer Academy 08, AAD meeting, Jul. 30-Aug. 3, 2008, Chicago, IL, P2008.
Anderson, "Maximum Tolerated Dose of PEP005 Topical Gel for the Treatment of Actinic Keratosis", Summer Academy 07, AAD Meeting, Aug. 1-5, 2007, New York, NY, P1503.
Anderson, "Multicenter, randomized, parallel-group, double-blind, vehicle-controlled phase III study to evaluate the efficacy and safety of PEP005 (ingenol mebutate) Gel, 0.05%, in patients with actinic keratoses on non-head locations", Poster session presented at the 22nd World Congress of Dermatology meeting, Seoul, May 2011, Abstract P2180.
Anderson, "Randomized, Double-Blind, Double-Dummy, Vehicle-Controlled Study of Ingenol Mebutate Gel 0.025% and 0.05% for Actinic Keratosis", J Am Acad Dermatol 60(6):934-43 (2009).
Anderson, "Safety and Efficacy of Ingenol Mebutate (PEP005) Gel, 0.025% and .05%,for Actinic Keratosis", Summer Academy 08, AAD meeting, Jul. 30-Aug. 3, 2008, Chicago, IL, P2009.
Appendino et al., *Synthesis of Modified Ingenol Esters*, Eur. J. Org. Chem, 3413-3420 (1999).
Banker et al., "E. Gels (Jellies)", Modern Pharmaceutics, Marcel Dekker, Inc., NY, (2002) 4th Ed., Revised and Expanded, 121:336-337, Version Date Jul. 26, 2013.
Bauer et al., "Konservierung and Mikrobielle Reinheit", Lehrbuch der Pharmazeutischen Technologie, Miteiner Einfuehri.Jng in die Biopharmazie, Wissenschaftliche Verlagsgesellschaft mbH Stuttgart, 2002, p. 157-159, 179-180, 287, 288, 458.
Beeby, Philip J. *Angeloyl Chloride: Synthesis and Utilisation in the Partial Synthesis of Lantadene A (Rehmannic Acid)*, Tetrahedron Letters, 38:3379-3382 (1977).
Benhadji, "Antiproliferative Activity of PEP005, a Novel Agent that Activates PKCδ and inhibits P KCα, Alone and in Combination with Cytotoxic Agents in Human Solid Tumor Cancer Cell Lines", Clin. Cancer Res 11.24 (2005) AbsA189.
Benhadji, "Antiproliferative Activity of PEP005, A Novel Ingenol Angelate That Modulates PKC Functions, Alone and in Combination With Cytotoxic Agents in Human Colon Cancer Cells", British Journal of Cancer, 99(11):1808-1815 (2008).
Berge et al. "Pharmaceutical Salts" J. Pharmaceutical Sciences, 66:1-19(1977).
Berman, "A multicenter, randomized, parallel-group, double-blind, vehicle-controlled evaluation of the efficacy and safety of PEP005 (ingenol mebutate) Gel, 0.015%, in patients with actinic keratoses on the head (face or scalp)", Poster session presented at the 22nd World Congress of Dermatology, Seoul, May 2011, Abstract P2179.
Berman, "Discovery and Development Timeline of a Novel Treatment for Actinic Keratosis: PEP005 (Ingenol Mebutate) Gel", Poster presented at the 2009 South Beach Symposium, Miami, Feb. 12-16, 2009.
Berman, "Pharmacotherapy of Actinic Keratosis", Expert Opin. Pharmacother, 10(18):3015-3031 (2009).
Block, Lawrence H., *Medicated Applications*, Remington (Ed.) The Science and Practice of Pharmacy, vol. II, Chapter 90, p. 1577-1597 (1885/1995).
Breccia, "NF-κB as a Potential Therapeutic Target in Myelodysplastic Syndromes and Acute Myeloid Leukemia", Expert Opin. Ther. Targets 14(11):1157-1176 (2010).
Bruserud, "Therapeutic Targeting of NF-κB in Myelodysplastic Syndromes and Acute Myeloid Leukaemia—The Biological Heterogeneity", Expert Opin. Ther. Targets 14(11):1139-1142 (2010).
Bundgaard et al., "Studies on the stability of corticosteroids VI. Kinetics of the rearrangement ofbetamethasone-17-valerate to the 21-valerate ester in aqueous solution", Int. J. Pharm. 7:197-203 (1981).
Challacombe, "Neutrophils Are a Key Component of the Antitumor Efficacy of Topical Chemotherapy with Ingenol-3-Angelate", The Journal of Immunology, 177(11):8123-8132 (2006).

Chamberlain, "Australian College of Dermatologists 4th Annual Scientific Meeting Report", Expert Rev. Dermatol. 3(4):433-436 (2008).
Chase and Shapiro, *Medical Applications of Radioisotopes*, Remington (Ed.) The Science and Practice of Pharmacy, vol. II, Chapter 51, p. 843 (1885/1995).
Chiao and Robinson, *Sustained-Release Drug Delivery Systems*, Remington (Ed.) The Science and Practice of Pharmacy, vol. II, Chapter 94, pp. 1660-1675 (1885/1995).
Clayden et al. "Nucleophilic substitution at the carbonyl (C=O) group", Organic Chemistry, Oxford University Press (2001) Chapter 12, p. 290 (3 pages).
Cozzi, "Induction of Senescence in Diterpene Ester-Treated Melanoma Cells via Protein Kinase C-Dependent Hyperactivation of the Mitogen-Activated Protein Kinase Pathway", Cancer Res 66(20):10083-10091 (Oct. 15, 2006).
De Vita et al., Cancer: Principles and Practice of Oncology. J.B. Lippincott Co., Philadelphia. PA, Chapter 30, "Cancers of the Skin", pp. 1094-1123 (1982).
Dictionary of Pharmacy, D.B. Worthen, Ed. in Chief, Pharmaceutical Products Press, p. 240 (2004).
Dukes, *General Considerations for Stability Testing of Topical Pharmaceutical Formulations*, Topical Drug Delivery Formulations, Chapter 10, Osborne and Amann (Eds.), pp. 197-211 (1990).
Emer, "Trends in the Treatment and Detection of Skin Cancer", Journal of Drugs in Dermatology, 10(1):16-18 (Jan. 2011).
EP0330094, Translation of Claims, Feb. 12, 2015 (2 pages).
EP0330094, Translation of Description, Feb. 12, 2015 (7 pages).
EPO Letter accompanying subsequently filed items on behalf of Sandoz AG against EP 1988877 (06 820 561.6), dated Oct. 29, 2015 (16 pages).
EPO Notice of Opposition on behalf of Actavis Group PTC ehf against EP 1988877 (06 820 561.6), dated Nov. 12, 2014 (16 pages).
EPO Notice of Opposition on behalf of Galenicum Health S.L. against EP 1988877 (06 820 561.6), dated Nov. 12, 2014 (16 pages).
EPO Response to Notice of Opposition on behalf of Leo Laboratories Limited for EP 1988877 (06 820 561.6), dated Aug. 26, 2015 (42 pages).
EPO, Notice of Opposition on behalf of Sandoz AG against EP 1988877 (06 820 561.6), dated Nov. 11, 2014 (36 pages).
Ersvaer, "Circulating T Cells in Patients with Untreated Acute Myelogenous Leukemia are Heterogeneous and Can Be Activated Through the CD3/TCR Complex", Hematology, 12(3):199-207 (2007).
Ersvaer, "T Cells Remaining After Intensive Chemotherapy for Acute Myelogenous Leukemia Show a Broad Cytokine Release Profile Including High Levels of Interferon-γ That Can Be Further Increased by a Novel Protein Kinase C Agonish PEP005", Cancer Immunol Immunother, 56(6):913-925 (2007).
Ersvaer, "The Protein Kinase C Agonist PEP005 (Ingenol 3-Angelate) in the Treatment of Human Cancer: A Balance between Efficacy and Toxicity", Toxins, 2(1):174-194 (2010).
European Medicines Agency (EMA/650464/2012), Assessment Report "Picato", pp. 9-14, (Sep. 20, 2012).
Evans and Taylor, "Pro-Inflammatory, Tumour-Promoting and Anti-Tumour Diterpenes of the Plant Families Euphorbiaceae and Thymelaeaceae", in Progress in the Chemistry of Organic Natural Products, 44, Founded by L. Zechmeister, Edited by W. Herz, H. Grisebach, and G.W. Kirby, Springer Verlag, New York, pp. 1-98 (1983).
Evans et al., "An assay procedure for the comparative irritancy testing of esters in the tigliane and daphnane series" Inflammation, 3(3):215-223 (1979).
Ewald, "Therapy-Induced Senescence in Cancer", JNCI, 102(20):1536-1546 (Oct. 20, 2010).
Feltkamp et al., "Pharmazeutische Qualitatskontrolle", Georg Thieme Verlag Stuttgart New York, pp. 502-504 (1983).
Fenske, "Actinic Keratoses: Past, Present and Future, Journal of Drugs in Dermatology", 9(5):45-49 (May 2010).
Florence et al., "Factors Influencing Drug Stability", Physiochemical Principles of Pharmacy, Macmillan Press Ltd., 3rd ed., p. 135, 1998.

(56) References Cited

OTHER PUBLICATIONS

Foss, "Connexin-Based Signaling in Acute Myelogenous Leukemia (AML)", Biochimica et Biophysica Acta 1798(1):1-8 (2010).
Frankel, "What's New in the Treatment of Actinic Keratoses", Cutis, 87(2):62-64 (2011).
Fredly, "The Combination of Conventional Chemotherapy with New Targeted Therapy in Hematologic Malignancies: The Safety and Efficiency of Low Dose Cytarabine Supports its Combination with New Therapeutic Agents in Early Clinical Trials", Current Cancer Therapy Reviews, 5(4):243-255 (2009).
Freeman, "Study to Determine the Optimal Tolerated Regimen of Ingenol Mebutate (PEP005) Gel For Actinic Keratosis of the Face or Face and Scalp", Summer Academy 08, AAD meeting, Jul. 30-Aug. 3, 2008, Chicago, IL, P2010.
Galiczynski, "Nonsurgical Treatment of Nonmelanoma Skin Cancer", Dermatol Clin, 29(2):297-309 (2011).
Ghoul, "Epithelial-to-Mesenchymal Transition and Resistance to Ingenol 3-Angelate, a Novel Protein Kinase C Modulator, in Colon Cancer Cells", Cancer Res 69(10):4260-4269 (May 15, 2009).
Ghoul, "PEP005, A Novel Agent That Activates PKCδ Inhibits PKCα, Displays Antiproliferative Activity Alone and in Combination with Cytotoxic Agents in Human Cancer Cell Lines", Proc Am Assoc Cancer Res, 47:518-519 (2006)
Ghoul, "PEP005, A Novel Ingenol Angelate Mediates Apoptosis in Human Cancer Cell Lines by Activation of p38 and MAPK Pathways, via a PKC-dependent Mechanism", Clin Cancer Res 11(24)Pt 2:9010 (2005).
Giuliano, "Advances in Melanoma Senescence and Potential Clinical Application", Pigment Cell Melanoma Res, (Dec. 11, 2010), 1-14.
Gotta et al., "On the Active Principles of the Euphorbiaceae, IX$^a$ Ingenane Type Diterpene Esters from Five *Euphorbia* Species", Z. Naturforsch. 39b, 683-694 (1984).
Green and Beardmore, "Home Treatment of Skin Cancer and Solar Keratoses", Australas J. Dermatol. 29:127-130 (1988).
Gross, "Maximum Tolerated Dose and Safety of PEP005 (Ingenol Mebutate) Gel for Topical Treatment of Superficial Basal Cell Carcinoma", Summer Academy 09, AAD meeting, Jul. 31, 2009, Boston MA, Poster 1902.
Gross, "Safety and Efficacy of Ingenol Mebutate (PEP005) Gel for Topical Treatment of Superficial Basal Cell Carcinoma", J Am Acad Dermatol 60(3) Suppl 1:AB141 (2009).
Grossberg, "Topical Antineoplastic Agents in the Treatment of Mucocutaneous Diseases", Curr Probl Dermatol, 40:71-82 (2011).
Hampson "The Diterpene Ester 3 Ingenyl Angelate Has Potent Anti-Leukemic Activity Mediated via PKC-delta as well as p38 and p42/44 MAP Kinases", Proc Amer Assoc Cancer Res, 46:1262-1263 (2005).
Hampson, "Kinetics of ERK1/2 Activation Determine Sensitivity of Acute Myeloid Leukaemia Cells to the Induction of Apoptosis by the Novel Small Molecule Ingenol 3-Angelate (PEP005)", (May 14, 2010).
Hampson, "PEP005, A Selective Small-Molecule Activator of Protein Kinase C, Has Potent Antileukemic Activity Mediated via the delta Isoform of PKC", Blood, 106(4):1362-1368 (Aug. 15, 2005).
Hampson, "The Anti-Tumor Agent, Ingenol-3-Angelate (PEP005), Promotes the Recruitment of Cytotoxic Neutrophils by Activation of Vascular Endothelial Cells in a PKC-δ Dependent Manner", Cancer Immunol Immunother, 57:8 (2008), 1241-1251.
Hampson, "Treatment of Actinic Keratoses Acute Myeloid Leukemia Therapy Treatment of Basal Cell Carcinoma Protein Kinase C Activator", Drugs of the Future, 30(10):1003-1005 (2005).
Hampson et al., "PEP-005", Drugs of the Future, 30:1003-1005 (2005).
Hoepfner et al., "Eth, Fiedler, Lexikon der Hilfsstoffe fur Pharmazie, Kosmetik und angrenzende Gebiete", Editio Cantor Verlag Aulendorf, Band 9: Der Pharmazeutische Betrieb, 5th Ed. p. 658 (2002).
Hohmann, "Diterpenoids from Euphorbia peplus", Planta Med., 66:291-294 (2000).

Hoover (Ed.) Dispensing of Medication, A practical manual on the formulation and dispensing of pharmaceutical products, *Pharmaceutical Factors*, p. 70; *Tablets*, p. 122-156; *Dermatologicals* pp. 147-156 (Mack Publishing Company, Easton, Pennsylvania) (1976).
Hruza, "Ingenol Mebutate for Actinic Keratoses", Journal Watch Dermatology, (Jun. 26, 2009).
Jenway, "pH Meters", from www.jenway.com, Nov. 11, 2014 (2 pages).
Jerant et al., "Early Detection and Treatment of Skin Cancer", Amer. Fam. Phys., 62(2):357-368, (2000).
Kane-Maguire, "Modulation of Fibroblast Phenotype and Extracellular Matrix Composition by 3-Ingenyl Angelate Induces Improved Dermal Cosmesis", Wound Rep Reg, 18(6):A85 (2010).
Kedei, "Characterization of Cytokine Response Induced by Ingenol 3-Angelate in WEHI-231 Cells", Proc Amer Assoc Cancer Res, 46:724 (2005).
Kedei, "Characterization of the Interaction of Ingenol 3-Angelate with Protein Kinace C", Cancer Research 64:3243-3255 (May 1, 2004).
Kirby, "Cloning of Casbene and Neocembrene Synthases From Euphorbiaceae Plants and Expression in *Saccharomyces cerevisiae*", Phytochemistry, 71(13) 1466-1473 (2010).
Kondratieva, Technology of the drug forms, Moscow, "Medicine" 1991, vol. 1, p. 84, lines 42-43, p. 86, lines 13-23, p. 95, lines 25-27, p. 96, line 39 through p. 100, line 1 and its English translation.
Kostenbauder and Bogardus, (1885/1995) *Reaction Kinetics*, Remington (Ed.) The Science and Practice of Pharmacy, vol. I, Chapter 18, pp. 231-240.
Kupchan et al., "Antileukemic principles isolated from Euphorbiaceae plants", Science 191:571-572 (1976).
Lachman et al., "Stability Analysis", The Theory and Practice of Industrial Pharmacy, Varghese Publishing House, Bombay, 3d edition, pp. 190-193, 764 (1987).
Le, "Immunostimulatory Cancer Chemotherapy Using Local Ingenol-3-Angelate and Synergy with Immunotherapies", Vaccine 27(23):3053-3062 (2009).
Le, "Immunostimulatory Chemotherapy with PEP005", Tissue Antigens, 66(5):554 (2005).
Lebwohl M. "A randomized, parallel-group, double-blind, vehicle-controlled, multicenter study of the efficacy and safety of PEP005 (ingenol mebutate) gel, 0.015%, in patients with actinic keratoses on the head", Poster session presented at the 22nd World Congress of Dermatology meeting, Seoul, May 2011, Abstract P2181.
Lee, "Novel Anti-Leukemic Compound Ingenol 3-Angelate Inhibits T Cell Apoptosis by Activating PKC Theta", JBC Papers in Press Manuscript M1099.041962, (May 14, 2010), 1-17.
Li, "The Skin Cancer Chemotherapeutic Agent Ingenol-3-Angelate (PEP005) is a Substrate for the Epidermal Multidrug Transporter (ABCB1) and Targets Tumor Vasculature", Cancer Res 70(11):4509-4519 (Jun. 1, 2010) (additional 7 pages of supplementary material).
Li, "The Skin Cancer Chemotherapeutic Agent PEP005 is a Substrate for the Epidermal Multidrug Transporter (ABCB1) and Targets Tumor Vasculature", Proc Am Assoc Cancer Res, 51:429 (2010).
Li, "The Skin Tumor Chemotherapeutic Agent PEP005 is a Substrate for the Multidrug Resistance Protein MDRI and Damages Tumor Vascularity", J Invest Dermatol 128(Suppl 1):S74 (2008).
Lowrie, "Species Strain and Tissue Variation in the Metabolism of [3H]-PEP005 II Metabolite Identification", Drug Metab Rev, 38 (Suppl. 1):162-163 (2006).
Madan, "Non-Melanoma Skin Cancer", Lancet, 375(9715):673-85 (2010).
Madden, "Species, Strain, and Tissue Variation in the Metabolism of [$^3$H]-PEP005 I: Metabolite Profiling", Drug Metab Rev, 38(Suppl. 1):137 (2006).
Maier, "Preclinical Evaluation of the Novel Diterpene Ester Ingenol 3-Angelate to Support the Selection of Tumor Indications for Clinical Studies", Proc Am Assoc Cancer Res, 48:1323 (2007).
Marco, "Ingenane and lathyrane diterpenes from the latex of Euphorbia canariensis", Phytochemistry, 45(3):563-570 (Jun. 1, 1997).

(56) References Cited

OTHER PUBLICATIONS

Mason, "The Induction of Senescence-Like Growth Arrest by Protein Kinase C-Activating Diterpene Esters in Solid Tumor Cells", Invest New Drugs, Jul. 28, 2009.
Mischiati, "Potential Role of PKC Inhibitors in the Treatment of Hematological Malignancies", Current Pharmaceutical Design, 14(21):2075-2084 (2008).
Murdan, Sudaxshina, *Drug delivery to the nail following topical application*, Intl. J. Pharmaceutics, 236:1-26 (2002).
Narin, J.G. *Solutions, Emulsions, Suspensions, and Extracts*, Remington (Ed.) The Science and Practice of Pharmacy, vol. II, Chapter 86, p. 1495-1523 (1885/1995).
Ogbourne, "Mechanism of Action of PEP005 for Topical Applications", Summer Academy 07, AAD Meeting, Aug. 1-5, 2007, New York, NY, P1500.
Ogbourne, "Novel Mechanism of Action Predicts Short Course of Therapy of PEP005.for Topical Applications", Poster presented at the 21st World Congress of Dermatology, Oct. 1-5, 2007, P6698.
Ogbourne, "Proceedings of the First International Conference on PEP005", Anti-Cancer Drugs, 18:357-362 (2007).
Olsnes, "The Protein Kinase C Activator PEP005 Increases the Chemokene Release in Native Acute Myelogenous Leukemia (AML) Blasts", ISEH 36th Annual Scientific Meeting / Experimental Hematology, 35(9):Suppl 1:87 (2007).
Olsnes, "The Protein Kinase C Agonist PEP005 Increases NF-κB Expression, Induces Differentiation and Increases Constitutive Chemokine Release by Primary Acute Myeloid Leukaemia Cells", British Journal of Haematology, 145(6):761-774 (2009).
Opferkuch et al., *Zur Chemie des Ingenols, I Ingenol und einige seiner Derivate [On the Chemistry of Ingenol, I Ingenol and Some of its Derivatives]*, Z. Naturforsch., 36b:878-887 [With English Abstract] (19810.
Osol, Arthur, "Stability of Pharmaceutical Products", Remington's Pharmaceutical Sciences, Mack Publishing Co., $16^{th}$ Ed., p. 1429, (1980).
Patel, "An Update on Nonmelanoma Skin Cancer", The Journal of Clinical and Aesthetic Dermatology, 4(2):20-27 (Feb. 2011).
Radebaugh and Ravin, *Preformulation*, Remington (Ed.) The Science and Practice of Pharmacy, vol. II, Chapter 83, p. 843 (1885/1995).
Ramsay, "The Sap from Euphorbia Peplus is Effective Against Human Nonmelanoma Skin Cancers", British Journal of Dermatology, 164(3):633-636 (2011).
Reikvam, "Primary Human Acute Myelogenous Leukemia Cells Release Matrix Metalloproteases and their Inhibitors: Release Profile and Pharmacological Modulation", European Journal of Haematology, 84(3):239-251 (Nov. 15, 2009).
Reilly, William J., "Pharmaceutical Necessities", Remington: The Science and Practice of Pharmacy, $21^{st}$ Ed., Philadelphia College of Pharmacy and Science (2005) pp. 1058-1060.
Reuter, "Botanicals in Dermatology", Am J Clin Dermatol, 11(4):247-267 (2010).
Reuter, "Which Plant for Which Skin Disease? Part 2: Dermatophytes, Chronic Venous Insufficiency, Photoprotection, Actinic Keratoses, Vitiligo, Hair Loss, Cosmetic Indications", JDDG, 8(11):866-874 (2010).
Rosen, "Early Phase Clinical Development of PEP005 Topical Gel for Basal Cell Carcinoma", Poster presented at the 21st World Congress of Dermatology, Oct. 1-5, 2007, P5755.
Rosen, "Safety and Efficacy of PEP005 Topical Gel for the Treatment of Nodular and Superficial Forms of Basal Cell Carcinoma", Summer Academy 07, AAD Meeting, Aug. 1-5, 2007, New York, NY, P1502.
Rosen, "Safety and Efficacy of PEP005 Topical Gel for the Treatment of Squamous Cell Carcinoma In Situ", Poster presented at the 21st World Congress of Dermatology, Oct. 1-5, 2007, P5703.
Rudnic and Schwartz, *Oral Solid Dosage Forms*, Remington (Ed.) The Science and Practice of Pharmacy, vol. I, Chapter 92, pp. 1615-1649 (1885/1995).
Sablin, "Characterization of Epithelial-Mesenchymal Transition Associated with Resistance to PKC Modulators", Poster Session G from 6th International Symposium on Targeted Anticancer Therapies (TAT 2008) Mar. 20-22, 2008: Bethesda, MD.
Saklani, Plant-Derived Compounds in Clinical Trials, Drug Discovery Today, 13(3-4):161-171, (Feb. 2008).
Salm, "The Measurement of PEP005 in Human Whole Blood by HPLC-Electrospray-Tandem Mass Spectrometry", The Drug Monit., 25(4):500 (2003).
Sanchez-Duffhues, "Activation of Latent HIV-1 Expression by Protein Kinase C Agonists. A Novel Therapeutic Approach to Eradicate HIV-1 Reservoirs", Current Drug Targets, 12(3):348-356 (2011).
Schmieder, "Multicenter, Open-Label, Dose-Area Escalation, Cohort Study to Evaluate the Safety and Tolerability of PEP005 (Ingenol Mebutate) Gel 0. 05% Applied for Two Consecutive Days to Treatment Area(s) Of Up To A Total of $100cm^2$ In Patients With Actinic Keratoses", J Am Acad Dermatol, 62(3):Suppl 1 (2010), AB 106 (21 p poster included).
Schmieder, "Safety and Tolerability of PEP005 (Ingenol Mebutate) Gel, 0. 05% Applied for 2 Consecutive Days to Areas Up to 100 $cm^2$ for Actinic Keratosis on the Extensor Forearm", Summer Academy 09, AAD meeting, Jul. 31, 2009, Boston MA, Poster 1903.
Schuller, "Positive results for Peplin phase IIa 'sun spot' trial", Nov. 28, 2005, http://www.labonline.com/au/content/life-scientist/news/positive-results-for-pepliu-phase-iia-sun-spot-trial--941853623#ixzz4OnC8OynB [Retrieved online: Nov. 1, 2016].
Sciarra, John J., *Aerosols*, Remington (Ed.) The Science and Practice of Pharmacy, vol. II, Chapter 95, pp. 1676-1692 (1885/1995).
Serova, "Effects of Protein Kinase C Modulation by PEP005, a Nobel Ingenol Angelate, On Mitogen-Activated Protein Kinase and Phosphatidylinositol 3-Kinase Signaling in Cancer Cells", Mol Cancer Ther 7(4):915-922 (Apr. 2008).
Serova, "PEP005 Targets Cell Survival and Invasion by PKCs/Ras/MAPK/p38 Activation and AKT/PKB Inhibition", Proc Am Assoc Cancer Res, 47:518 (2006).
Siller, "Discovery and Development Timeline of a Novel Treatment for Actinic Keratosis: PEP005 (Ingenol Mebutate) Gel", J Invest Dermatol 129(12):2918 (2009).
Siller, "PEP005 (Ingenol Mebutate) Gel for the Topical Treatment of Superficial Basal Cell Carcinoma: Results of a Randomized Phase IIa Trial", Australasian Journal of Dermatology, 51:2(2010) 99-105.
Siller, "PEP005 (Ingenol Mebutate) Gel, A Novel Agent for the Treatment of Actinic Keratosis: Results of a Randomized, Double-Blind, Vehicle-Controlled, Multicentre, Phase IIa Study", Australasian Journal of Dermatology, 50(1):16-22 (2009).
Siller, "Treatment of Actinic Keratosis with PEP005 Topical Gel", Conference poster from Summer Academy of Dermatology meeting, San Diego, CA, 2006, P1900.
Simon and Maibach, "Relevance of Hairless Mouse as an Experimental Model of Percutaneous Penetration in Man", Skin Pharmacol Appl Skin Physiol, 11(2):80-6 (1998).
Simpson, "Direct Small-Molecule Kinase Activation: Novel Approaches for a New Era of Drug Discovery", Current Opinion in Drug Discovery & Development, 12(5):585-596 (2009).
Sokoloski, Theodore D. *Solutions and Phase Equilibria*, Remington (Ed.) The Science and Practice of Pharmacy, vol. I, Chapter 16, pp. 194-212 (1885/19950).
Sorg and Hecker, *On the Chemistry of Ingenol, II [1] Esters of Ingenol and $\Delta^{7-8}$ -Isoingenol*, Z. Naturforsch. [Journal of Natural Science], 37b:748-756 (1982).
Sorg and Hecker, *On the Chemistry of Ingenol, III [1] Synthesis of 3-Deoxy-3-oxoingenol, Some 5-Esters and of Ethers and Acetals of Ingenol*, Z. Naturforsch, 37b:1640-1647 (1982).
Spencer, "Multicenter, Randomized, Double-Blind, Vehicle-Controlled, Dose-Ranging Study to Evaluate the Efficacy and Safety of PEP005 (Ingenol Mebutate) Gel 0. 005%, 0. 01 %, and 0. 015% When Used to Treat Actinic Keratoses On The Head", J Am Acad Dermatol, 62(3):Suppl 1 (2010), AB105 (25p poster included).

(56) References Cited

OTHER PUBLICATIONS

Spencer, "Safety and Efficacy of PEP005 (Ingenol Mebutate) Gel, 0,005%, 0,01%, and 0,015%,for Actinic Keratosis on the Head (Face or Scalp)", Summer Academy 09, AAD meeting, Jul. 31, 2009, Boston, MA, Poster 1900.
Sucker et al., "Spezielle Haltbarkeitsversuche", Pharmazeutische Qua litaetskontrolle, Bd.3: Arbeitstechniken der Pharmazeutischen Industrie, Chap.4, 7:502-504 (1983).
Swanson N. "A multicenter, randomized, parallel-group, double-blind, vehicle-controlled study to evaluate the efficacy and safety of PEP005 (ingenol mebutate) gel, 0.05% in patients with actinic keratoses on non-head locations", Poster session presented at the 22nd World Congress of Dermatology meeting, Seoul, May 2011, Abstract P2182.
Swanson, "Multicenter, Randomized, Parallel-Group, Double-Blind, Vehicle-Controlled Study to Evaluate the Efficacy and Safety of PEP005 (Ingenol Mebutate) Gel, 0.05% In Patients with Actinic Keratoses on Nonhead Locations", J Am Acad Dermatol, 62(3):Suppl 1 (2010), AB2 (28p poster included).
Teng, "Biotransformation of Ingenol-3-Angelate in Four Plant Cell Suspension Cultures", Biocatalysts and Biotransformation, 27(3):186-194 (May-Jun. 2009).
Teng, "Regioselective Acylation of 3-O-Angeloylingenol by Candida Antarctica Lipase B", Fitoterapia 80(4):233-236 (2009).
Ulrich, "Emerging Drugs for Actinic Keratosis", Expert Opin. Emerging Drugs, 15(4):545-555 (2010).
US Pharmacopeia "General Information", The United States Pharmacopeia, The National Formulary, United States Pharmacopeia Convention Meeting, Washington, D.C. , USA, Apr. 12-16, 2000, USP 28(1191): 2727-2728, Jan. 1, 2005.
USPTO Final Office Action in co-pending U.S. Appl. No. 14/269,055, dated Aug. 10, 2016 (14 pages).
USPTO Non-Final Office Action in co-pending U.S. Appl. No. 14/269,055, dated Jan. 25, 2016 (7 pages).
USPTO Non-Final Office Action in co-pending U.S. Appl. No. 15/163,454, dated Aug. 10, 2016, 2016 (15 pages).
USPTO Non-Final Office Action in co-pending U.S. Appl. No. 15/163,295, dated Aug. 11, 2016 (15 pages).
USPTO Non-Final Office Action in co-pending U.S. Appl. No. 15/163,390, dated Aug. 9, 2016 (14 pages).
USPTO Report on the Filing or Determination of an Action Regarding a Patent or Trademark, in the Case of *Leo Pharma A/S et al.*, v. *Actavis Laboratories UT, Inc., et al.*, Case No. 1:16-cv-00333-UNA, dated May 6, 2016 (2 pages).
Vadas, Elizabeth B. (1885/1995) *Stability of Pharmaceutical Products*, Remington (Ed.) The Science and Practice of Pharmacy, vol. I, Chapter 38, pp. 639-647.
Wade and Weller (Eds.), (1994) Handbook of Pharmaceutical Excipients, Second Edition, *Benzoic Acid*, p. 32-34; *Benzyl Alcohol*, pp. 35-37; *Benzyl Benzoate*, pp. 38-39; *Citric Acid Monohydrate*, pp. 123-125; *Sodium Citrate Dihydrate*, pp. 443-445; (American Pharmaceutical Association, Washington).
Waning, "Controlling the Mdm2-Mdmx-p53 Circuit", Pharmaceuticals, 3(5):1576-1593 (2010).
Warrilow, "HIV Type 1 Inhibition by Protein Kinase C Modulatory Compounds", AIDS Research and Human Retroviruses, 22(9):854-864 (2006).
Weedon et al., "Home treatment of basal cell carcinoma" Med. J Aust., 1:928 (1976).
Weiss, "Study to Determine the Safety, Tolerability, and Efficacy of PEP005 (Ingenol Mebutate) Gel for Actinic Keratosis of the Dorsum of the Hand", Summer Academy 09, AAD meeting, Jul. 31, 2009, Boston MA, Poster 1901.
Welburn, "Skin Sensitization Potential of PEP005 Topical Gel", Summer Academy 07, AAD Meeting, Aug. 1-5, 2007, New York, NY, P1504.
Wikipedia: "pH-Wert" (http://de.wikipedia.org/wiki/PH-Wert) (2 pages).
Wiriyachitra, "Investigations of Medicinal Plants of Euphorbiaceae and Thymelaeaceae Occurring and Used in Thailand; II. Cryptic Irritants of the Diterpene Ester Type from Three *Excoecaria* species", Planta Med, 51(5):368-71 (Oct. 1985).
Wolfe, "Oncology Watch: Update on New Directions in AK Treatment", Practical Dermatology, (Jan. 2010), 27.
Zayed, "Dietary Cancer Risk Conditional Cancerogens in Produce of Livestock Fed on Species of Spurge (*Euphorbiaceae*)", J. Cancer Res. Clin Oncol, 124:131-140 (1998).
U.S. Appl. No. 15/163,454, filed May 24, 2016, Brown et al.
Adolf and Hecker, *On the Active Principles of the Spurge Family III. * Skin Irritant and Cocarcinogenic Factors from the Caper Spurge*, Z. Krebsforsch. 84:325-344 (1975) [With English translation of the Summary—see title page].
Aulton, M.E. (Editor), *Pharmaceutics The Science of Dosage Form Design*, $2^{nd}$ Edition, Churchill Livingstone Press, Spain (2002) (682 pages).
Carstensen and Rhodes (Editor), *Drug Stability Principles and Practices*, Chapter 3: *Kinetic pH Profiles*, Third Edition, Marcel Dekker, Inc., New York, (2000) (64 pages).
Connors et al., (Editor), *Chemical Stability of Pharmaceuticals a Handbook for Pharmacists*, John Wiley & Sons, Inc., (1986), pp. 76-77.
Gennaro, Alfonso R. (Editor) *Remington: The Science and Practice of Pharmacy*, vol. I, $19^{th}$ Ed., Mack Publishing Company, (1995) (pp. 204-206; 237; 639-643; 1462; 1496; 1509; 1517-1518; 1585; 1596; 1648; 1672; and 1687).
Gundidza et al., *A skin irritant principle from Euphorbia matabelensis Pax*, J. Ethnopharmacology, 39:209-212 (1993).
Hartwell, Jonathan L., *Plants Used Against Cancer. A Survey*, Lloydia, 32(2):153-205 (1969).
Hughes et al., *Cellular Proliferation In The Mouse As Revealed by Autoradiography With Tritiated Thymidine*, Physiol. and Bacteriol. Proc. N.A.S., 44:476-483 (1958).
Jones, MB BS (QLD), Brad, *Efficacy and Action of Topical Diterpenes from Euphorbia Peplus in Non-Melanoma Skin Cancer*, A thesis presented for the degree of Master of Philosophy, University of Queensland, School of Medicine, Central Clinical Division, Brisbane, Queensland, Nov. 2002 (159 pages).
Khan et al., *Kinetic Analysis by HPLC-Electrospray Mass Spectrometry of the pH-Dependent Acyl Migration and Solvolysis as the Decomposition Pathways of Ifetroban 1-O-Acyl Glucuronide*, Anal. Chem. 70:1622-1628 (1998).
Lea et al., *Comparative Biochemistry of Hepatomas VI. Thymidine Incorporation into DNA as a Measure of Hepatoma Growth Rate* Cancer Research 26 Part 1:466-469 (1966).
Marcus, Yzhak, (Editor), *The Properties of Solvents*, Wiley Series in Solution Chemistry, vol. 4, John Wiley & Sons, Chichester, (1998), pp. 143-163.
Sayed et al., *Constituents of Egyptian Euphorbiaceae. IX. Irritant and cytotoxic ingenane esters from Euphorbia paralias L.*, Experientia, 36(10:1206-1207 (Oct. 1980) [With English Abstract—see p. 3].
U.S. Department of Health and Human Services Food and Drug Administration, (CDER) (CBER), *Guidance for Industry Q1A(R2) Stability Testing of New Drug Substances and Products* Revision 2, Nov. 2003 (25 pages).
USPTO Non-Final Office Action for U.S. Appl. No. 14/269,055 dated Feb. 28, 2017 (24 pages).
USPTO. Final Office Action for U.S. Appl. No. 15/163,390 dated Feb. 22, 2017 (27 pages).
USPTO Final Office Action for U.S. Appl. No. 15/163,454, dated Feb. 22, 2017 (25 pages).
Yoshioka and Stella (Editor), *Stability of Drugs and Dosage Forms*, Kluwer Academic Publishers, New York (2002), (274 pages).
Schmidt, Richard J., *The Ingenane Polyol Esters*, Chapter 9, *Naturally Occurring Phorbol Esters*, Ed. Fred J. Evans, Ph.D., M.P.S., F.L.S., School of Pharmacy, University of London, CRC Press, Inc. Florida, (1986), pp. 245-269.
U.S. Appl. No. 14/269,055, filed May 2, 2014, Brown et al.
U.S. Appl. No. 15/163,390, filed May 24, 2016, Brown et al.
U.S. Appl. No. 15/163,410, filed May 24, 2016, Brown et al.
U.S. Appl. No. 15/163,454, filed May 24, 2016 Brown et al.
EPO Examination Report for EP App. No. 11171538.9, dated Mar. 28, 2017 (6 pages).
Kibbe, A.H., "Benzyl Alcohol", Handbook of Pharmaceutical Excipients, Ed. 3, American Pharmaceutical Association et al, USA, pp. 41, 191-220, 372, and 442 (Jan. 1, 2000) (12 pages).

THERAPEUTIC COMPOSITIONS

This application is a continuation, and claims priority, of co-pending U.S. application Ser. No. 14/269,055, filed May 2, 2014, which is a continuation of U.S. application Ser. No. 13/769,809, filed Feb. 18, 2013, now U.S. Pat. No. 8,536,163, issued Sep. 17, 2013, which is a continuation of U.S. application Ser. No. 13/563,698, filed Jul. 31, 2012, now U.S. Pat. No. 8,377,919, issued Feb. 19, 2013, which is a continuation of Ser. No. 12/097,258, having a 371 completion date of Jan. 21, 2009, now U.S. Pat. No. 8,278,292, issued Oct. 2, 2012, which is a U.S. National Stage application, and claims priority of International Application No. PCT/GB2006/004739, filed Dec. 18, 2006, which claims priority of United Kingdom Application No. 0525680.5, filed Dec. 16, 2005.

The contents of all of the prior applications are incorporated herein by reference in their entirety.

The present invention relates to compositions of compounds obtainable from *Euphorbia* species and which are useful in the treatment of skin cancers.

The compound ingenol angelate can be isolated from various *Euphorbia* species, and particularly from *Euphorbia peplus* and *Euphorbia drummondii*. Ingenol angelate exists in three isoforms; ingenol-3-angelate (isoform 'b'), ingenol-5-angelate (isoform 'a') and ingenol-20-angelate (isoform 'c'). The first of these is also referred to herein as I3A and has the following structure:

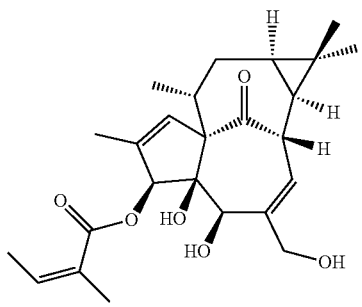

Ingenol angelate has been found to be highly toxic for skin cancer cells via rapid mitochondrial disruption and cell death by primary necrosis, while leaving healthy cells unaffected.

U.S. Pat. No. 6,432,452 discloses compounds present in an active principle derived from plants of the species *Euphorbia peplus, Euphorbia hirta* and *Euphorbia drummondii*, which show selective cytotoxicity against several different cancer cell lines. The compounds are useful in effective treatment of cancers, particularly malignant melanomas and squamous cell carcinomas (SCCs). The compounds are selected, from jatrophanes, pepluanes, paralianes and ingenanes. The preferred compound is an angeloyl-substituted ingenane obtained from the sap of *Euphorbia peplus*.

Microgram quantities of ingenol angelate are typically therapeutically effective. However, the tendency for isoform 'b' to undergo rearrangement to isoform 'a' and subsequently to isoform 'c' presents a formulation problem, where it is desired to restrict the formulation to either a specific isoform or to a ratio of isoforms. This is particularly a problem with I3A, as the different isoforms have different solubilities.

There is a need for an effective, topical treatment for skin cancer, as systemic treatments involving other drugs necessarily result in exposure of susceptible healthy cells, in non-target parts of the body, to cytotoxic chemicals. In addition, systemic anti-cancer treatments, whether administered orally or by injection, have lower patient acceptance.

There is a need to provide a stable formulation of ingenol angelate, preferably for topical administration.

It has now, surprisingly, been found that ingenol angelate can be solubilised, substantially without rearrangement between isoforms, in an acceptable, aprotic solvent in the presence of an acceptable, miscible acidic buffer.

Thus, in a first aspect, the present invention provides a formulation of ingenol angelate for use in therapy, wherein the ingenol angelate has been dissolved in a pharmaceutically acceptable, aprotic solvent, said formulation further comprising a pharmaceutically acceptable acidifying agent which is at least partially compatible with the solvent and which provides the formulation with an apparent pH of no greater than 4.5.

The present invention envisages formulations of any of the isoforms of ingenol angelate, or mixtures thereof. At present, the preferred isoform is isoform 'b', also referred to herein as I3A. It will be understood that references to 'ingenol angelate' and 'I3A' include reference to other isoforms and mixtures thereof, unless otherwise apparent.

Ingenol angelate can be dissolved in many solvents, and various solvents are illustrated in accompanying Example 1. However, ingenol angelate is generally susceptible to rearrangement in protic solvents, and any substantial degree of rearrangement, typically beyond about 1% for plant derived products, but more preferably about 0.5%, is undesirable in a pharmaceutical formulation.

In aprotic solvents, which are generally solvents that do not contribute protons to a solution, such as polyethylene glycol, dissolution can take some considerable time and this, together with the temperatures required, can also lead to rearrangement to an extent above acceptable levels.

Substances such as acetone and acetonitrile are capable of dissolving I3A, but are not generally pharmaceutically acceptable, and may not be suitable for long term storage. More acceptable may be substances such as methyl ethyl ketone, ethyl acetates, or diethyl ether, but benzyl alcohol is generally most preferred.

A number of substances are suitable to dissolve I3A, but stability is not guaranteed, and generally unacceptable rearrangement levels may be observed after periods ranging between as little as 12 hours and as much as six months or a year.

In the absence of water, or other protic solvent, them will not be a measurable pH. Under such conditions, and especially at elevated temperatures, rearrangement is likely. Thus, it has been found that it is generally possible to inhibit rearrangement by the presence of a suitable acid.

Suitable acids are generally organic acids, as it has been established that I3A can decompose much below about a pH of 3, while rearrangement is likely to occur at above a pH of about 4.5. Where it is intended to store the formulation for periods of any length, such as a month or more, than it is preferred that the acid be in the form of a buffer. Suitable buffers include citrate buffer, phosphate buffer, acetate buffer and citrate-phosphate buffer, although other buffers will be apparent to those skilled in the art. In particular, it is preferred that the buffer provides an apparent pH to the formulation of no greater than 4.5 and no less than 2.5. A formulation pH of less than 4 is more preferred, and it is particularly preferred that the apparent formulation pH be 3.8 or less, preferably around 3.5, or less. An apparent pH of around 3 is useful. A buffer having as pH of 2.75 has been found to be particularly advantageous, conferring an apparent pH of about pH 3.5 to the final formulation when used in quantities as illustrated in the accompanying Examples. A preferred pH range of the buffer is between 2.6 and 2.85, preferably pH 2.7-pH 2.8, and is preferably a citrate buffer. It will be appreciated that the acid will generally be in the form of an aqueous solution, preferably in deionised water, unless otherwise indicated. Citrate buffer is preferred. Where acetate buffer is used, this may typically have a pH range of 3.5 to 5.5, while citrate-phosphate buffer may typically have a pH range of 2.75 to 7.0.

It will be understood that a solution in which the solvent is aprotic cannot have a pH, as this is a measurement of the $H^+$ ion. However, where such a solution is at least partially miscible with an acid, or acidic buffer, and such is present, then attempts to measure the pH will yield a result. Preferred formulations of the invention are made up as topical administration forms, and will generally comprise a majority of buffer, or ionic solution, but will always comprise aprotic solvent, so that only an apparent, rather than an absolute, pH can be measured, as the measured pH relates only to the ionic component. A suitable means for measuring apparent pH is with the Jenway 3320 pH meter. Accordingly, the result may not have the meaning normally ascribed to an ionic solution, especially where the amount of acid or buffer is small, but the significance is that, insofar as any ionic environment is present, that environment is acidic. As the amount of acid increases, so the apparent pH becomes more equivalent to pH. While not being bound by theory, it is likely that ingenol angelate is primarily dissolved in the aprotic solvent, as it has very low solubility in water. Subsequent addition of the ingenol angelate solution in solvent to an acidified ionic solution allows a suitable, optionally aqueous, ionic solution of ingenol angelate to be prepared, thereby avoiding dissolution of ingenol angelate directly in a protic solvent, which is when the greatest amount of rearrangement appears to take place. Thus, contact with a protic solvent can immediately result in the formation of the other isoforms but this can be minimised if a small amount of acid or acidic buffer, which terms are used synonymously herein unless otherwise apparent, is added. Even the act of dissolution in prude solvents, given the length of time and conditions necessary, can lead to undesirably high levels of isoforms forming, such is the susceptibility of ingenol angelate to rearrangement.

The aprotic solvent and the acid are at least partially compatible, in that a stable preparation of the two can be formed. The acid and solvent are preferably miscible, and are preferably miscible at all ratios. In particular, it is generally preferred to add a small amount of buffer to the solvent during, or shortly after, solubilisation of the ingenol angelate, in order to keep the apparent pH at a relatively low level. Subsequently, it may be desirable to make up the solubilised ingenol angelate in an excess of the buffer that was used during the initial solubilisation. Stable preparations made up with an excess of buffer are illustrated in Example 9, below.

It will be appreciated that it is preferred that the acid and solvent be sufficiently miscible to be able to form a single phase, although immiscible, or less miscible, solvents and acids may be prepared in the form of emulsions or microemulsions. Such emulsions can be stable, but the provision of a mixture of solvent and acid as a single phase generally further minimises any risk of angelate rearrangement.

Solvents that are particularly useful in the present invention are those which exhibit both hydrophilic and lipophilic traits, such as ring systems which are preferably homocyclic, and which have hydroxy groups substituted thereon but separated by at least one carbon atom from the ring structure. A particularly preferred example of such a solvent is benzyl alcohol.

Although it is possible to use an acid rather than a buffer, it is generally preferred to use an acidic buffer to minimise the fluctuation in pH. As such, it will be appreciated that, whilst the term 'buffer' will generally be used herein, this term also encompasses acids and acid preparations, where appropriate. A particularly preferred buffer is citrate buffer, pH 3 or lower, preferably pH 2.75. In benzyl alcohol, a 2.5% w/w quantity of pH 2.5 citrate buffer will generally yield an unmeasurable apparent pH but, at higher quantities, yields a pH of around pH 3. The relationship between pH of buffer and apparent pH is explored in the accompanying Examples. At low quantities of buffer when dissolving I3A in the solvent it is simply preferred to keep the environment acidic, and the nature of the preferred buffer at these levels is similar to the nature of the preferred buffer when subsequently diluting the formulation for use. It is generally preferred to acidify the solvent, preferably benzyl alcohol, with an amount of acidic buffer, preferably between 1 and 10% by weight, more preferably between 2 and 5%, prior to addition of I3A.

While the formulation does not have to be diluted for use, it is generally the case that I3A is a potent substance, and stock solutions of I3A in solvent, preferably benzyl alcohol, may be made up for storage, preferably at 8° C. or below. Such stock solutions may then be diluted, preferably with buffer, as desired, when making up any final formulation or preparation.

The amount of buffer used when solubilising the ingenol angelate can vary between about 0 and 100%. When the amount is 0, it is preferred to add a quantity of buffer shortly after adding the ingenol angelate to the solvent, in order to minimise the likelihood of any rearrangement taking place. It is generally preferred to avoid using amounts of buffer greater than 100% by weight of the solvent, as dissolution directly into the buffer is generally not readily achievable. It is preferred to employ the buffer as a means to keep the apparent pH of the solvent at a low level, without providing any substantial amount of protic solvent during dissolution of the ingenol angelate. Once the ingenol angelate has been substantially dissolved, then it is possible, and may even be desirable, to make up the formulation with an excess of buffer comprising, if desired, other optionally protic constituents, such as antibiotics, for example. Preferred levels of buffer are in the region of 0.5%-10%, and preferably between 1% and 5%, with about 2-3% being most preferred during the dissolution phase. The dissolution phase comprises dissolving at least a majority of the ingenol angelate in the solvent, and preferably at least 95% w/w ingenol angelate in the solvent, more preferably at least 99% w/w.

Formulations of the present invention may be used directly, or may be stored for future use. In addition, formulations of the present invention may provide a base formulation which can then be further modified prior to use. For example, as described above, the formulation may be made up in an excess of buffer or may be formulated into a gel, for example.

It has also been found that formulations of the present invention are generally more stable at lower temperatures. Particularly preferred formulations of the present invention, such as those comprising benzyl alcohol and citrate buffer, may exhibit substantial stability at temperatures as high as 40° C. but in general, increasing stability is observed at temperatures below room temperature and pressure (RTP), and the greatest stability is observed at temperatures below about 8° C. Freezing does not appear to enhance stability so that, in general, the greatest stability is achieved simply by placing formulations of the invention in a conventional refrigerator at a temperature of between about 2° C. and 8° C.

The present invention further provides a process for preparing a solution of ingenol angelate, comprising dissolving the ingenol angelate in a pharmaceutically acceptable, aprotic solvent, said formulation further comprising a pharmaceutically acceptable acidifying agent which is a least partially compatible with the solvent and which provides the formulation with an apparent pH of no greater than 4.5, said acid being added with, before, or after the ingenol angelate.

In an alternative, the present invention provides a process for preparing a solution of ingenol angelate, comprising dissolving the ingenol angelate in a pharmaceutically acceptable, aprotic solvent, said process comprising the addition of a pharmaceutically acceptable acidifying agent which is at least partially compatible with the solvent and which provides the formulation with an apparent pH of no greater than 4.5, said acidifying agent being added with, before, or after the ingenol angelate. The acidifying agent is preferably a buffer.

It is preferred to add the acid, or buffer, sufficiently soon after addition of the I3A to ensure that no more than about 1%, and preferably no more than about 0.5%, of the 'b' isoform rearranges into the 'a' isoform. Preferably, the acid or buffer is added to the solvent before adding the I3A, although all three ingredients may be combined at the same time. This latter is the least preferred option.

This process may also be used for the preparation of ingenol angelate formulations using other compounds and solvents, such as polyethylene glycol, where direct solubilisation may be associated with an unacceptable level of rearrangement. Although I3A can dissolve in PEG, it takes in the region of an hour at elevated temperature, which generally leads to the generation of unacceptable levels of the 'a' isoform. If the I3A is dissolved in buffered benzyl alcohol first, this can then be introduced directly into the PEG, without the prolonged exposure to heat. As only enough benzyl alcohol is needed to solubilise the I3A, then the total amount of benzyl alcohol in the final PEG formulation need only be in the region of 1% w/w or less.

These formulations may be kept for sustained periods, especially when kept at temperatures of 8° C. or lower. Preferred compositions see no more than about 1%, and preferably no more than about 0.5%, rearrangement of the 'b' isoform to the 'a' isoform after 3 months, more preferably 6 months.

There is further provided the use of a formulation of the invention in the treatment of a skin cancer.

The invention also provides the use of ingenol angelate in the manufacture of a medicament for the treatment or prevention of a skin cancer, wherein the ingenol angelate is dissolved in a pharmaceutically acceptable, aprotic solvent, said formulation further comprising a pharmaceutically acceptable acidifying agent which is at least partially compatible with the solvent and which provides the formulation with an apparent pH of no greater than 4.5.

Suitable cancers for treatment in accordance with the present invention include squamous and basal cell cancers.

It will be appreciated that 'treatment', as used herein, includes both therapy and prophylaxis.

The present invention also provides a method of treating a subject suffering from a cancerous skin condition, comprising the topical application of a therapeutically effective amount of a composition of the invention to the area of the cancerous condition.

Suitable subjects for treatment are mammals, including humans, primates, livestock animals (including cows, horses, sheep, pigs and goats), companion animals (including dogs, cats, rabbits, guinea pigs), captive wild animals, and laboratory animals, such as rabbits, mice, rats, guinea pigs and hamsters. The compositions of the present invention are particularly suitable for the treatment of human skin cancers.

It will be appreciated that the formulations of the present invention may be used in any suitable cancer prophylaxis or treatment. Administration forms may be any suitable, and include creams, gels, ointments, lotions, sprays, lacquers and paints for topical application, powders, solutions and suspensions for the airways, solutions and emulsions for injection, capsules, syrups and elixirs for oral administration, and pessaries and suppositories. Other suitable administration forms will be readily apparent to those skilled in the art, and may include transdermal patches, for example. In a preferred embodiment of the present invention, the ingenol angelate formulations are formulated for topical administration.

In all cases, the initial formulation is as a formulation of the invention. The formulation may be made up into the final form either just before use as soon as desired after preparation of the formulation, but will usually remain a formulation of the invention at all times.

Formulations may comprise additional ingredients, as discussed below. It is particularly preferred to employ antioxidants, as these appear to provide enhanced stability to the formulations. Suitable examples of antioxidants include retinol, ascorbic acid, lycopene, butylated hydroxytoluene, and tocopherol.

The amount of ingenol angelate required for pharmaceutical efficacy will be apparent to those skilled in the art, and may be adapted according to physiological parameter, such as age, weight and sex of the patient, as well as the size of any lesion. In general, an amount of ingenol angelate suitable to provide between about 0.01 μg $cm^{-2}$ to about 1 mg $cm^{-2}$ may be employed, with a range of 0.1 mg $cm^{-2}$ to about 100 μg $cm^{-2}$ being more preferred. In the accompanying Examples, a formulation providing 15 μg $cm^{-2}$ was used, but formulations of 1 μg $cm^{-2}$, or less, have been found to be effective. In the alternative, formulations of the invention may contain I3A in an amount of from 0.001% (w/w) to 0.15% (w/w), more preferably up to about 0.1-0.12% (w/w).

Topical formulations are a preferred embodiment of the present invention. In this regard, a heretofore unrecognised property of the ingenol angelates is particularly useful, in that it has been found that they have vasoconstrictive properties. Accordingly, systemic distribution of the active ingredient is minimised, owing to the reduced blood flow in the vicinity of treatment.

It will be appreciated that the nature of the formulation will determine the rate of permeation across the skin. As such, it is generally preferred that the formulation be prepared such that a rate of permeation of at least about 11 ng $cm^{-2}$ $h^{-1}$ is achieved. There is no special upper limit, although it is generally preferred that this not exceed around 1 μg $cm^{-2}$ $h^{-1}$.

Topical formulations may take any suitable form. In general, it is preferred that they exhibit some level of viscosity, in order that they can be targeted at the desired area without running off. Accordingly, it is generally preferred to formulate ingenol angelate as creams, gels, ointments, and paints. Given the potency of ingenol angelate, paints may be employed, as they may be applied sparingly, depending on levels of the active ingredient.

Poloxamers may be used in preferred formulations of the present invention. They are co-polymers which consist of a hydrophobic polypropylene (POP) molecule sandwiched between two hydrophilic molecules of poloxyethylene (POE). Thus, they have the ability to solubilise lipophilic drugs within the hydrophobic core. Furthermore, poloxamer based aqueous gel formulations exhibit thermo-rheological properties, which may be advantageous for localised, sustained delivery of drugs. Above a certain temperature, known as the critical micelle temperature (cmt), the viscosity of the poloxamer gel increases dramatically. An increase in viscosity leads to a decrease in the diffusion of any drugs dissolved in the gel which slows down the release of drug from the gel and leads to sustained delivery. The increase in viscosity may also provide a prolonged, localised 'depot' at the site of action.

The cmt is dependent on a number of variables such as concentration of poloxamer and other additives such as propylene glycol. Ideally, the cmt should be at a temperature such that the formulation can be injected into the lesion as a liquid (ease of administration) and upon contact with body temperature a gel is formed with the aim of achieving a localised, sustained delivery of the drug. Five poloxamers are listed in the USP, and include poloxamer 188 and poloxamer 407. Poloxamer 188 has been approved as an excipient for IV formulations (http://www.accessdata.fda.gov).

Poloxamer gels have been used for subcutaneous delivery of insulin (Barichello et al., 1999) and other drug delivery systems for percutaneous use (Tobiyama et al., 1994). One particular copolymer, poloxamer 407 has been administered subcutaneously for the slow release of peptides and therapeutics proteins, which included interleukin-2 and human growth hormone (Morikawa et al., 1987; Katakama et al., 1997). Following administration, the gels slowly released the entrapped protein molecules over a period of 1-2 days. Furthermore, a substantial fraction of this poloxamer eventually underwent renal excretion.

Poloxamers are generally regarded as non-toxic and non-irritant materials. Animal toxicity studies, with dogs and rabbits, have shown poloxamers to be non-irritant and non-sensitising when applied, in 5% w/v and 10% w/v concentration, to the eyes, gums and skin. In a 14-day study of intravenous administration to rabbits, at concentrations up to 0.5 g/kg/day, no overt adverse effects were noted. A similar study with dogs also showed no adverse effects at dosage levels up to 0.5 g/kg/day. Furthermore, no haemolysis of human blood cells was observed over 18 hours at 25° C., with 0.001-10% w/v poloxamer solutions (Wade and Weller, 1994). However, hyperlipidemia in rats has been reported when an intraperitoneal (IP) injection (1.0 g/kg) of poloxamer 407 was introduced (Wasan et al., 2003).

Oils may also be used in the present invention. The use of an emulsion based intralesional formulation has been reported for the treatment of psoriasis (Ho et al., 1990). Prior to administration, a vehicle, such as polyoxyethylated castor oil, is normally diluted with saline to form the emulsion. However, our studies have shown that dilution of I3A with normal saline increases the conversion of isoform 'b' to 'a'. This conversion may be minimised if the administration time of the formulation is short.

There are a number of lipophilic products that are formulated as oily solutions for intramuscular administrations (IM), for example Prolixin Enanthate (Bristol Myers Squibb). The vehicle (oil) used varies widely from vegetable oils such as arachis oil (used with benzyl benzoate in Dimercaprol injection B.P.) and sesame oil (used in depot injections of Fluphenazine Enanthate injection B.P). The use of oleaginous vehicles may slow absorption due to delayed partitioning of the drug from the oil to the aqueous body fluids (Ford, 1987). When injected into an aqueous environment (such as muscle tissue) a relatively lipophilic drug such as I3A, dissolved in an oil phase, will have a tendency not to leave the oil and 'instantaneously' partition into the aqueous phase. In this way a sustained release effect can be achieved.

Buccal formulations may also be employed. Transmucosal delivery of therapeutic agents is a popular administration form, because mucous membranes are relatively permeable, allowing for the rapid uptake of a drug into the systemic circulation and avoiding first pass metabolism. Transmucosal products can be designed to be administered via the nasal route and oral/buccal route using mucoadhesives. In the development of these drug delivery systems, mucoadhesion of the device/formulation is a key element. The term 'mucoadhesive' is commonly used for materials that adhere to the mucin layer of a biological membrane. Mucoadhesive polymers have been utilised in many different dosage forms in efforts to achieve systemic and localised delivery of drugs through the different mucosae. These dosage forms include tablets, patches, tapes, films, semisolids and powders.

To serve as mucoadhesive polymers, the polymers should possess physicochemical features such as being predominantly anionic with numerous hydrogen bond-forming groups, suitable surface properties for wetting mucus/mucosal tissue surfaces and sufficient flexibility and length (molecular weight) to penetrate the mucus network or tissue crevices. Diverse classes of polymers have been reported as potential mucoadhesives such as carbomers (polyacrylic acids), hydroxypropyl methylcellulose (HPMC) as well as naturally occurring polymers, such as hyaluronic acid and chitosan.

Preparation of suitable formulations is within the skill of those in the art, and suitable excipients for inclusion in an such formulation include, for example, gellants, viscosifiers, penetration enhancers, preservatives, such as antibiotics and antifungals, and cosmetic ingredients, such as scents and colourings.

Suitable gelling agents include: water soluble cellulose derived polymers, such as hydroxyalkyl cellulose polymers (e.g. hydroxymethylcellulose, hydroxyethylcellulose, hydroxypropylcellulose and hydroxypropylmethylcellulose), carboxymethyl cellulose, methylhydroxyethyl cellulose and methyl cellulose, carbomer (e.g. carbopol); and carrageenans. The gelling agent may be added in any suitable amount, such as 1-5% (w/w). Preferred gelling agents are cellulose derived, most preferably hydroxyalkylcellulose, particularly hydroxyethylcellulose.

Suitable preservatives will be apparent to those skilled in the art, and include the parabens (methyl, ethyl, propyl and butyl), benzoic acid and benzyl alcohol. Preservatives employed solely for that purpose will generally form 1% (w/w) or less of the final topical formulation.

Suitable penetration enhancers include isopropyl alcohol, sulphoxides (such as dimethylsulphoxide, DMSO), Azones (e.g. laurocapram), pyrrolidones (for example 2-pyrrolidone), alkanols (e.g. decanol), and glycols (for example propylene glycol).

Preferred compositions of the invention comprise:
a) I3A;
b) penetration enhancer;
c) preservative;
d) getting agent; and
e) buffer;
wherein the composition has an apparent pH of between 3 and 4, inclusive.

A particularly preferred composition comprises:
a) 0.1% (w/w) I3A;
b) 30% (w/w) isopropyl alcohol;
c) 0.9% (w/w) benzyl alcohol;
d) 1.5% (w/w) hydroxy ethyl cellulose; and
e) 67.5% (w/w) citrate buffer pH 3, preferably pH 2.75.

The invention will now be described with reference to the accompanying Figures, wherein:

FIG. 1: shows a schematic representation of a Franz cell.

Figure 2:
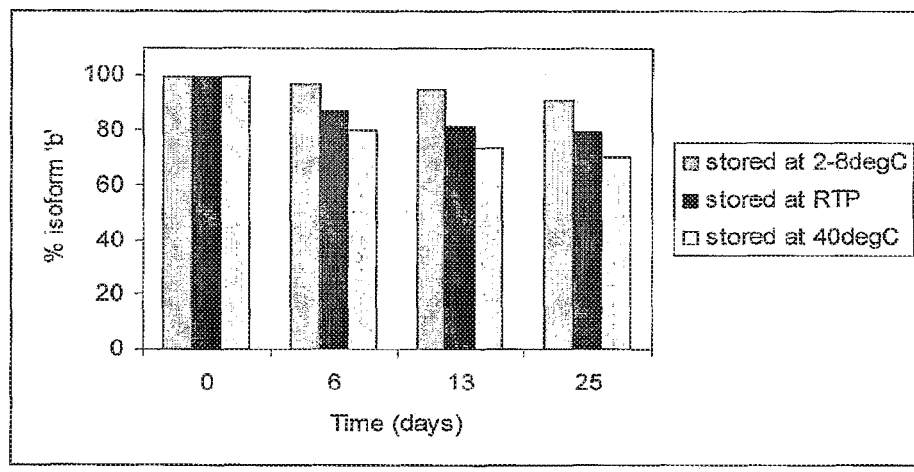

FIG. 2: Percentage of isoform 'b' isopropanol gel (pH 6.5).

Figure 3:
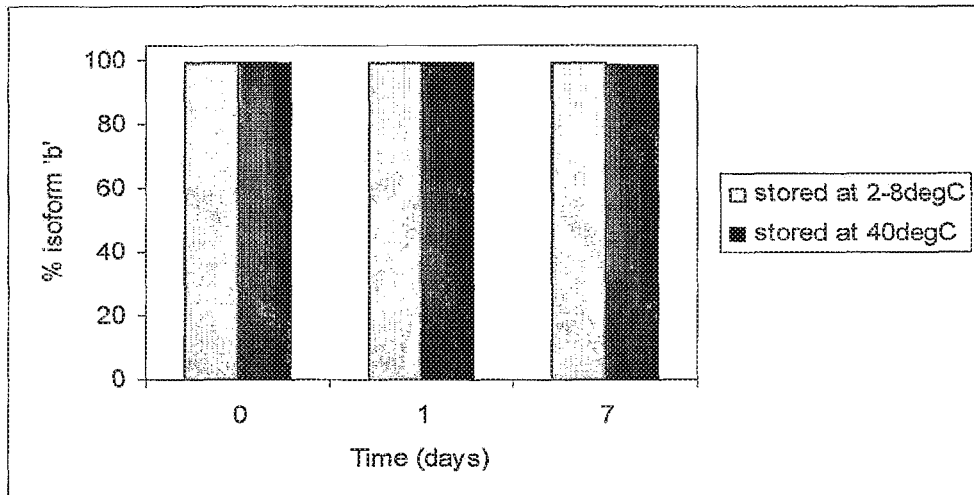

FIG. 3: Percentage of I3A 'b' in 30% IPA/citrate buffer (pH 3).

Figure 4:
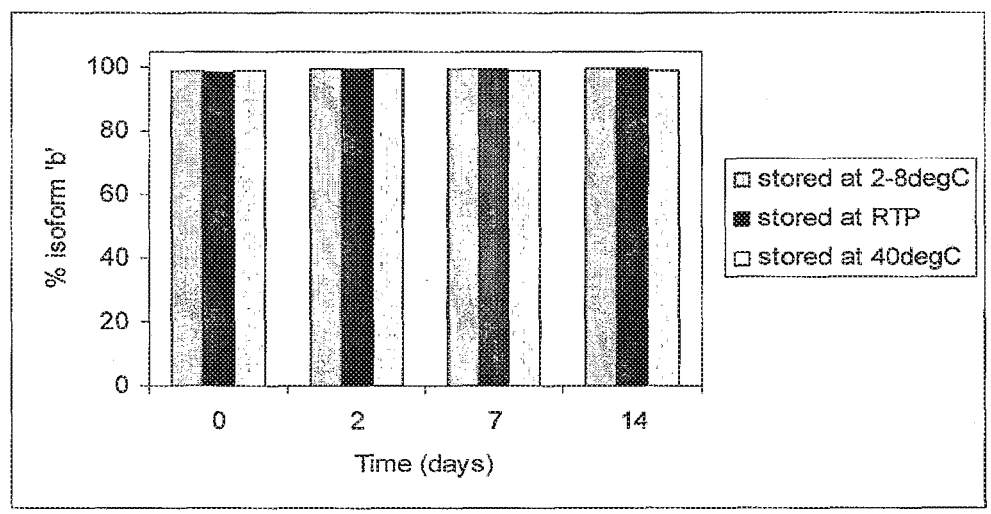

FIG. 4: Percentage I3A 'b' in 100% benzyl alcohol at 2-8° C., RTP and 40° C.

Figure 5:
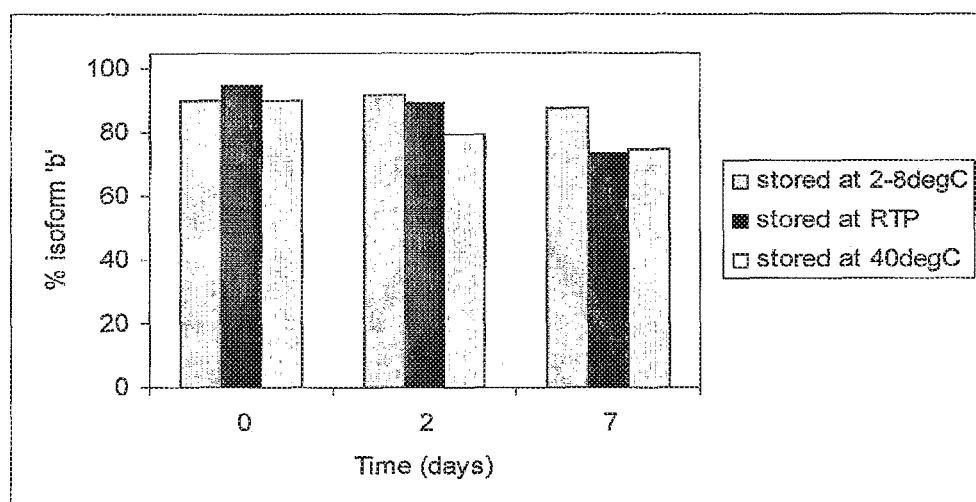

FIG. 5: Percentage I3A 'b' in 100% phenoxythanol at 2-8° C., RTP and 40° C.

Figure 6:
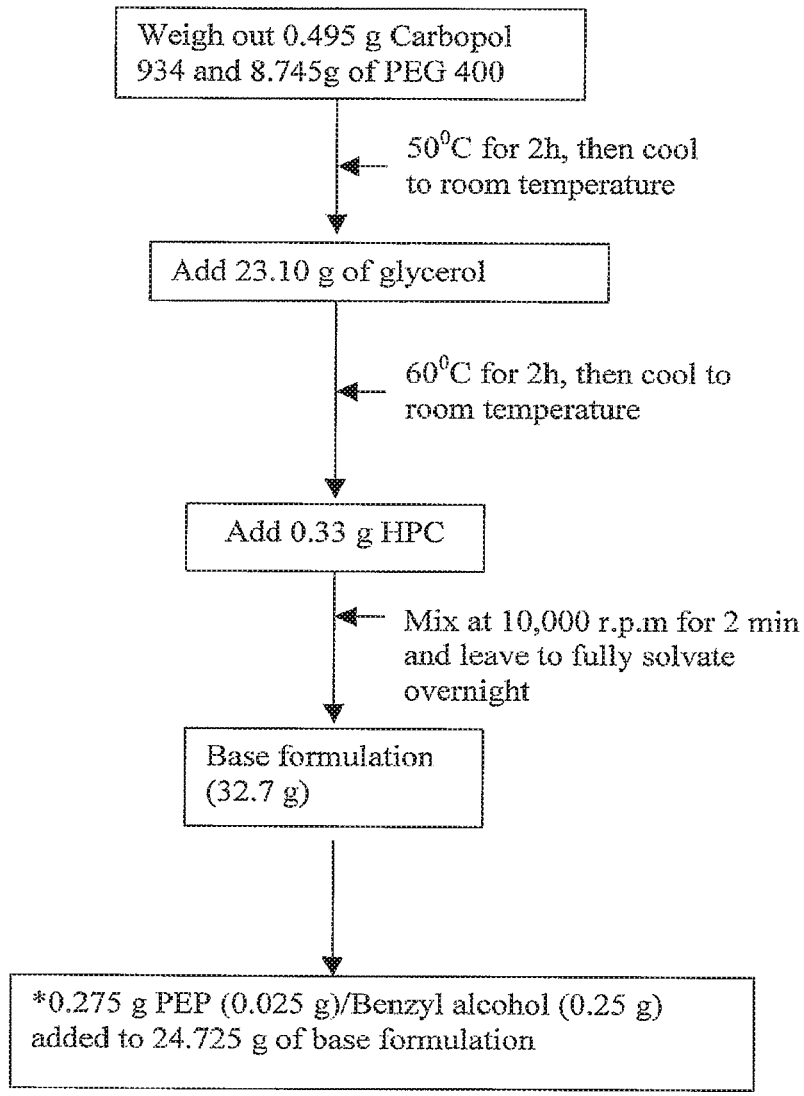

FIG. 6: shows a flow chart for the preparation of 0.1% w/w I3A Formulation 16 and the respective placebo. *For the placebo formulation 0.25 g of benzyl alcohol was added to 24.75 g of base formulation.

Figure 7:
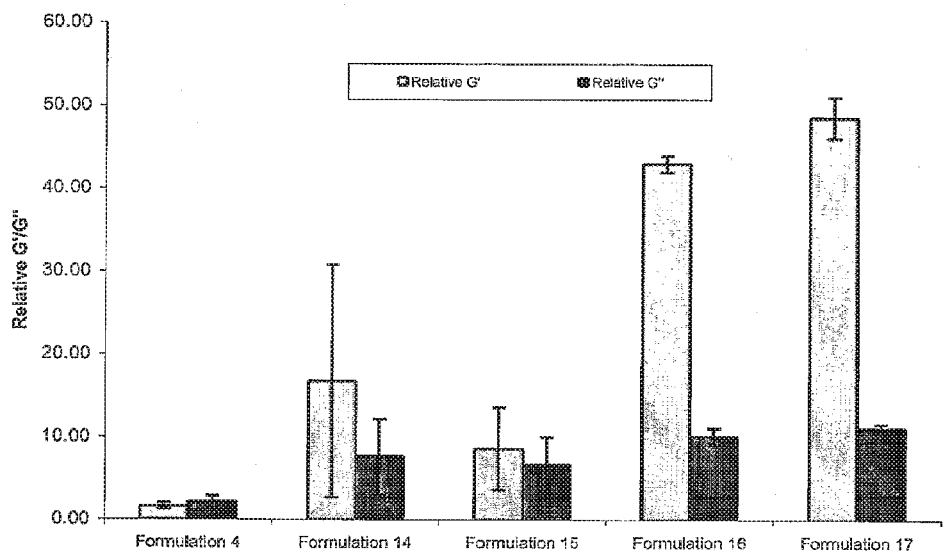

FIG. 7: Relative G' and G" values for Formulations 4, 14, 15, 16 and 17 (n=5±SD).

Figure 8:
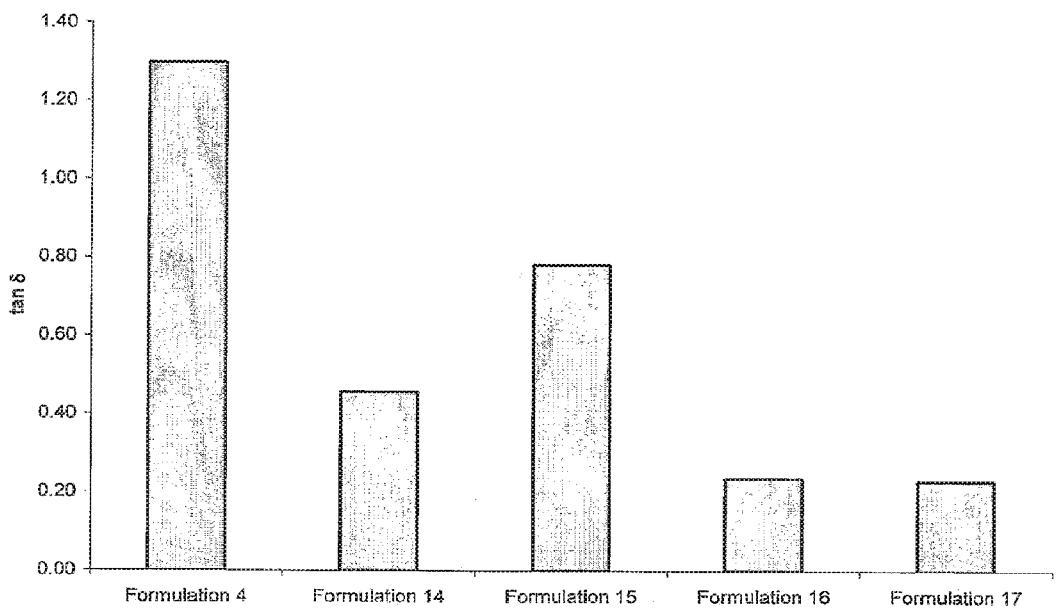

FIG. 8: Corresponding tan d values for Formulations 4, 14, 15, 16 and 17

Figure 9:
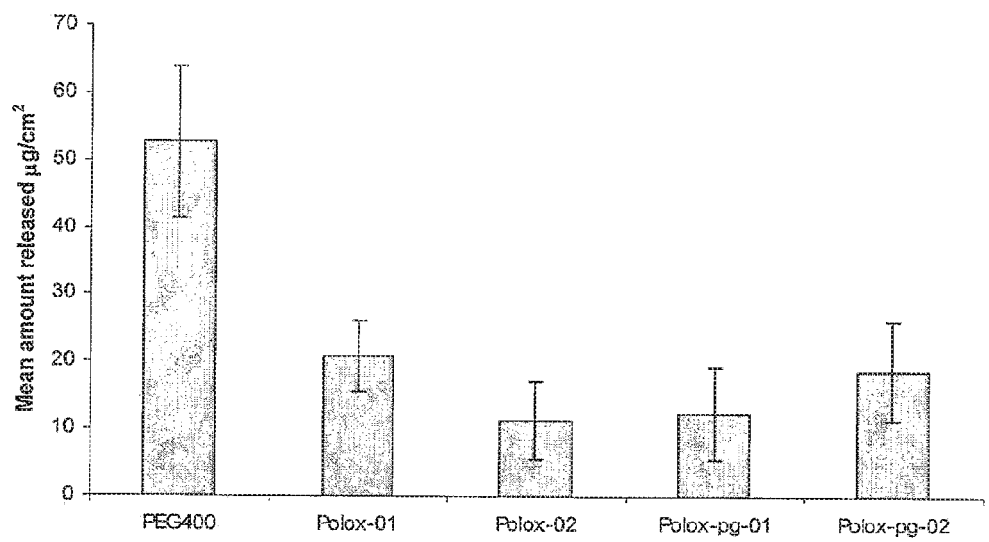

FIG. 9: Plot of mean amount released after 26 h ($\mu g/cm^2$) of I3A 'b' from 0.1% w/w poloxamer gel and PEG 400 formulations, (n=3±SE).

Figure 10:
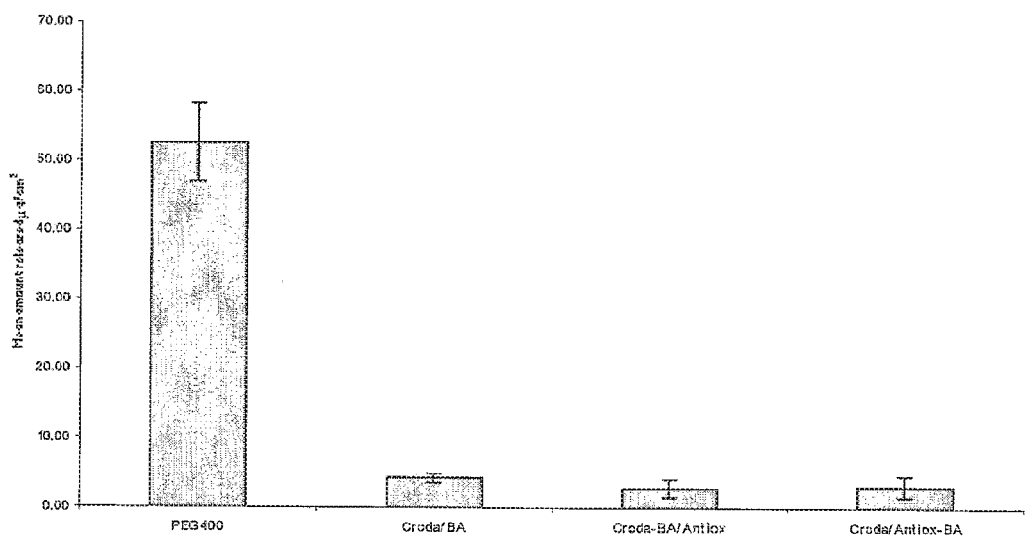

FIG. 10: Plot of mean amount released after 26 h ($\mu g/cm^2$) of I3A 'b' from 0.1% w/w oil and PEG 400 formulations, (n=3±SE).

The present invention will be further illustrated with regard to the following, non-limiting Examples.

EXAMPLE 1

The stability of I3A was investigated in various solvent systems, including acetone, acetonitrile, methanol/water, water, DMSO, phosphate buffers (pH range 4.5 to 7) and ammonium buffer (pH 4.5) and was shown to be stable in acetone, acetonitrile, DMSO, phosphate buffer pH 4.5 and ammonium buffer (pH 4.5). The rearrangement of the ingenol angelate appeared to occur in the order of isomer 'b' rearranging to isomer 'a' and then to isomer 'c'. Owing to the small quantities of active substance used, the measure of stability of the compound was calculated as the ratio of the area of peak 'b' to the area of peak 'a'.

Materials

TABLE 1

Suppliers of materials used in this Example

| Materials | Supplier |
| --- | --- |
| I3A (ingenol angelate) Batch No. 080402 and Batch No. 300502 | Supplied by Peplin Limited, Australia |
| β-Cyclodextrin sulphobutyl ether, 7 sodium salt (Captisol ®) Lot No. CY-03A-010244 | Cydex Incorporated, USA |
| 2-Hydroxypropyl-β-cyclodextrin (Cavasol ® W7 HP) Batch No. 74BO08 | Wacker-Chemie GmbH & Co., Germany |
| Miglyol 810N Lot No. 980403 Propylene Glycol Batch No. 286991 Mineral oil Lot No. 128H0136 Oleic acid Batch No. 9736588428 Span 80 Lot. No. 120H0454 Tween 80 Lot No. 44H0121 Polyethylene glycol 300 Lot No. 60H0463 DMSO | Sigma Chemical Co., UK |
| Sodium Hyaluronate (HA) Batch No. KX00282 | Kyowa Hakko Pharmaceuticals Japan |
| Monopotassium phosphate Batch No. 14286 | Aldrich Chemical Co., UK |
| Ammonium acetate Lot No. A147753001 Glacial acetic acid | BDH Laboratory Supplies, UK |
| Acetone-HPLC grade Acetonitrile-HPLC grade Methanol-HPLC grade | Rathburn Chemicals Ltd, UK |
| Deionised water (Elgastat Option 3A) | Elga Ltd., UK |
| Parafilm ® | American National Cam ™, USA |

All excipients used in the final formulation of I3A of compendial grade.

Methods

Stability Study of I3A in Solvents/Excipients

A stability study of I3A in the following solvent/excipients/excipient combinations was performed over 14 days (except where otherwise stated) at room temperature:

Acetone
Acetonitrile
Methanol
Methanol/water (70/30)
Water
Phosphate buffer pH 4.5, pH 5.5, pH 6.5, pH 7.0
DMSO*
Mineral oil
Miglyol 810
Polyethylene glycol 300
Propylene glycol
Oleic acid
2-Hydroxypropyl-β-cyclodextrin (Cavasol®/H$_2$O)
2-Hydroxypropyl-β-cyclodextrin (Cavasol®/PO$_4$ pH 4.5)
Tween 80/Span 80/H$_2$O
Tween 80/Span 80/PO$_4$ pH 4.5
β-cyclodextrin sulphobutyl ether (Captisol®)/H$_2$O**
β-cyclodextrin sulphobutyl ether (Captisol®)/PO$_4$ pH 4.5**
Sodium hyaluronate (HA)/PO$_4$ pH 4.5***
Sodium hyaluronate (HA)/H$_2$O pH 4.5***

*10 days study 7 days study *2 days study

A 0.5 mg/ml stock solution of I3A in acetonitrile was prepared. Aliquots of 1.0 ml were transferred to individual glass sample vials by a burette; the solutions were dried by air jet and then 1.0 g of the respective solvent/excipient/excipient combination was added to the vials. On Day 0, Day 5 and Day 14, aliquots of the stability samples were removed for HPLC analysis using the chromatographic conditions described under "Stability in DMSO", below. Stability was expressed as the ratio of peak 'b' to peak 'a' (and peak 'c' if present), with a high ratio indicating stability in a particular excipient.

HPLC Analysis for the Stability of I3A in Excipients Study

An alternate HPLC method was developed in order to separate out a "shoulder" appearing on peak 'b' that was seen with some preparations of I3A.

The chromatographic conditions employed for the excipients stability study were as follows:
Column: Hypercarb (ThermoQuest, Phenomenex) (S/no. 3.34070)
Column length: 100×4.60 mm
Column temperature: 25° C.
Guard column: $C_{18}$ Columbus (Phenomenex) (S/no. 202678)
Guard column length: 50×4.60 mm
Mobile phase: 50% v/v phosphate buffer pH 4.5/50% v/v acetonitrile
Flow rate: 1.0 ml/min
UV wavelength: 230 nm
Injection volume: 10 μl
Run time: 35 mins Preliminary In Vitro Diffusion Study Once the stability of I3A in the excipients and penetration enhancers had been established, a preliminary in vitro diffusion experiment could be conducted to determine the permeation of stratum corneum by I3A from some simple formulations. The Franz diffusion cell is designed to mimic the physiological and anatomical conditions of skin in situ. It is an air/fluid phase static cell, which comprises a donor compartment, receptor compartment and a side arm sampling port (see FIG. 1). Surgically excised skin is positioned between the two halves with the stratum corneum facing the donor compartment to allow for drug application.

An initial in vitro diffusion experiment using a simple formulation of I3A in miglyol was performed. There was no flux of the drug at all across the stratum corneum suggesting that the I3A as not formulated at its maximum thermodynamic activity in the miglyol. This formulation was used in later diffusion cell experiments as a negative control and also served to confirm the integrity of the stratum corneum, as if there is no diffusion of drug from this formulation, it can be assumed that the stratum corneum remains intact.

Manufacture of Formations

A formulation of I3A was prepared in phosphate buffer (pH 4.5) with β-cyclodextrins (Captisol®) added with a view to increasing the solubility and stability of I3A, and the flux of the drug. A second formulation in DMSO, a known penetration enhancer, was also prepared for comparative purposes, as well as a formulation in miglyol, which served as a negative control. The diffusion of I3A across the stratum corneum from these formulations was investigated.

The following formulations were prepared:

| Formulation | Description |
| --- | --- |
| 1 | I3A/Captisol ® (30 mM)/phosphate buffer pH 4.5 |
| 2 | Captisol ®(30 mM)/phosphate buffer pH 4.5 control |
| 3 | I3A/Miglyol |
| 4 | Miglyol control |
| 5 | I3A/DMSO/phosphate buffer pH 4.5 |
| 6 | DMSO/phosphate buffer pH 4.5 control |

Table 2 shows the % w/w of each of the ingredients present in the formulations. The ingredients were accurately weighed out into sealable glass vials and stirred vigorously with a magnetic stirrer bar for several hours at room temperature.

TABLE 2

Formulation of I3A for in vitro diffusion study

| Formulation | I3A (300502) | | Captisol ® (30 mM) | | $PO_4$ buffer | | Miglyol | | DMSO | | Total | |
| --- | --- | --- | --- | --- | --- | --- | --- | --- | --- | --- | --- | --- |
| | Mass (g) | % w/w | Mass (g) | % w/w | Mass (g) | % w/w | Mass (g) | % w/w | Mass (g) | % w/w | Mass (g) | % w/w |
| 1 | 0.0016 | 0.08 | 0.1299 | 6.54 | 1.8956 | 95.38 | — | — | — | — | 1.9875 | 100.00 |
| 2 | — | — | 0.1301 | 6.05 | 2.0203 | 93.95 | — | — | — | — | 2.1504 | 100.00 |
| 3 | 0.0016 | 0.08 | — | — | — | — | 2.0128 | 99.92 | — | — | 2.0144 | 100.00 |
| 4 | — | — | — | — | — | — | 2.0000 | 100.00 | — | — | 2.0000 | 100.00 |
| 5 | 0.0017 | 0.08 | — | — | 0.4035 | 20.04 | — | — | 1.6080 | 79.87 | 2.0132 | 100.00 |
| 6 | — | — | — | — | 0.4112 | 20.13 | — | — | 1.6320 | 79.87 | 2.0432 | 100.00 |

Choice of Receiver Fluid

2-Hydroxypropyl-β-cyclodextrin (Cavasol®, 1.38 mM) in $PO_4$ buffer (pH 4.5) was the receiver fluid used in this study in order to try to maintain sink conditions. A restriction on other reservoir fluids such as ethanol/water systems was imposed since 'back diffusion' of ethanol through the stratum corneum might have degraded the I3A present in the formulations.

Skin Preparation

A fresh, surgically excised sample of human skin was obtained directly after an abdominoplasty. The donor was a 56-year-old non-smoking female White Europid. Subcutaneous fat as carefully removed from the skin sample using forceps and a scalpel, and then the portion of skin was immersed in water at 60° C., for 45 s. The skin was then pinned, dermis side down, on a cork hoard and the epidermis (comprising stratum corneum and viable epidermis) gently removed from the underlying dermis. The dermis was discarded and the epidermal membrane floated onto the surface of water and taken up onto Whatman no. 1 filter paper. The resultant epidermal sheet was thoroughly dried and stored flat in aluminium foil at −20° C. until use.

A section of the epidermal sheet (with filter paper side up) was clamped and incubated for 4 h at 4° C. immersed in 0.1% w/v trypsin solution. The skin was then further incubated for 1 h at 37° C. The stratum corneum was physically removed by gently shaking the clamp with lateral movements. The resultant stratum corneum layer was washed twice with deionised water followed by 0.1% w/v antitrypsin solution to block enzyme activity and further washed twice with deionised water. The stratum corneum was dried and stored flat in aluminium foil at −20° C. until use.

Franz Cell Diffusion Study

Individually calibrated Franz diffusion cells with an average diffusional surface area of 0.56±0.05 cm² and an average receiver volume of 1.79±0.06 ml were used to conduct the diffusion experiments. The stratum corneum (prepared as described above) was washed with phosphate buffer (pH 4.5), cut with a 10" borer and mounted onto the Franz cells (illustrated in FIG. 1). The receiver fluid employed was 2-hydroxypropyl-β-cyclodextrin (Cavasol®)/phosphate buffer (pH 4.5) and this was incorporated into the Franz cell, stirred constantly with a magnetic stirrer and maintained at 37° C. The membranes were allowed to equilibrate with the receiver phase for 30 mins before applying the formulations. An infinite dose of each formulation was applied onto the membrane surface using a positive displacement Finpipette® and the donor chambers were protected with Parafilm®. Five sampling times were investigated (1, 2, 4, 6 and 24 h) whereby 200 µl of the receiver fluid was carefully withdrawn from the arm of the Franz cell; each sample removed was replaced by an equal volume of fresh (37° C.) receiver fluid. Throughout the experiment, any losses in receiver fluid due to evaporation from the Franz cell were replaced to maintain a constant volume. Samples were analysed via HPLC (supra).

HPLC Analysis for In Vivo Diffusion Study

The chromatographic conditions employed were as follows:
Column: Hypercarb (ThermoQuest, Phenomenex) (S/no. 3-34070)
Column length: 100×4.60 mm
Column temperature: 25° C.
Guard column: $C_{18}$ Columbus (Phenomenex) (S/no. 202678)
Guard column length: 50×4.60 mm
Mobile phase: 50% v/v ammonium buffer pH 4.5/50% v/v acetonitrile
Flow rate: 1.0 ml/min
UV wavelength: 230 nm
Injection volume: 10 µl
Run time: 35 mins Results Stability of I3A in Solvents and Excipients Table 3, below, provides an indication of stability of I3A in the various solvent systems. The stability of I3A in the solvents and excipients after 14 days (unless otherwise stated) at room temperature was quantified in terms of the ratio of isoform 'b' to isoforms 'a' and 'c', with a predominance of 'b' equating to stability. The results are summarised in Table 3. It is assumed that for an excipient in which I3A is not stable, other like excipients will not be suitable.

TABLE 3

Summary of the results of the stability study of I3A in various solvents and excipients

| Solvent/Excipient | Stable? | Comments |
|---|---|---|
| Acetone | ✓ | |
| Acetonitrile | ✓ | |
| Methanol | x | Isoform 'a' forms |
| Methanol/water (70/30) | x | Isoform 'a' then 'c' form |
| Water* | x | Isoform 'a' then 'c' form |
| DMSO* | ✓ | |

TABLE 3-continued

Summary of the results of the stability study of I3A in various solvents and excipients

| Solvent/Excipient | Stable? | Comments |
|---|---|---|
| Phosphate buffer pH 4.5 | ✓ | |
| Phosphate buffer pH 5.5 | x | Isoform 'a' forms |
| Phosphate buffer pH 6.5 | x | Isoform 'a' then 'c' form |
| Phosphate buffer pH 7.0 | x | Rapid formation of isoform 'c' |
| Ammonium buffer pH 4.5 | ✓ | |
| Mineral oil | ✓ | Viscous nature makes it difficult to extract I3A for HPLC analysis Precipitation of I3A |
| Miglyol 810 | ✓ | |
| Polyethylene glycol | ✓ | |
| Propylene glycol | x | Formation of 'a' and 'c' isoforms |
| Oleic acid | x | Difficult to quantify due to many interfering peaks in chromatogram. isoform 'a' present, shoulder on 'b' ('c' forming) |
| 2-Hydroxypropyl-β-cyclodextrin (Cavasol ®)/$H_2O$ | x | Large peak for isoform 'c' |
| 2-Hydroxypropyl-β-cyclodextrin (Cavasol ®)/$PO_4$ pH 4.5 | ✓ | Some precipitation of I3A |
| Tween 80/Span 80/$H_2O$ | ✓ | |
| Tween 80/Span 80/$PO_4$ pH 4.5 | ✓ | |
| β-cyclodextrin sulphobutyl ether (Captisol ®)/$H_2O$** | x | Isoforms 'a' and 'c' present |
| β-cyclodextrin sulphobutyl ether (Captisol ®)/$PO_4$ pH 4.5** | ✓ | |
| Sodium hyaluronate/$H_2O$*** | x | Isoform 'a' present |
| Sodium hyaluronate/$PO_4$ pH 4.5*** | ✓ | |

*10 days study
**7 days study
***2 days study

Preliminary In Vitro Diffusion Study

Table 4 gives a comparison of the flux between formulations of I3A as determined from the cumulative amount of I3A permeated per unit area DMSO is one of the earliest and most widely investigated penetration enhancers, and it has been shown to enhance the percutaneous penetration of many drugs in vitro and in vivo experiments. As such, DMSO was a useful comparator excipient to confirm the penetration of stratum corneum by I3A. However, given the highly toxic nature of this solvent and the fact that it produces irreversible skin damage, DMSO would not be used in a final formulation. There was no permeation of I3A observed with the miglyol formulation. A possible explanation for this lack of diffusion of I3A from miglyol across the stratum corneum is that I3A is highly soluble in this excipient.

TABLE 4

Comparison of the flux between formulations of I3A as determined from the cumulative amount of I3A permeated per unit area (mean ± s.e.m, n = 3 and 4, respectively)

| Formulation | (µg/cm²/h) |
|---|---|
| I3A/Captisol ®/phosphate buffer pH 4.5 | 1.92 ± 1.02 |
| I3A/DMSO/phosphate buffer pH 4.5 | 0.61 ± 0.13 |

The results show that I3A diffuses across the stratum corneum (which forms the main barrier for the diffusion of most drugs) at detectable levels.

Stability Study at 4-8° C.

The stability of I3A in various solvents at 4-8° C. was investigated. A stock solution of 1.26 mg of I3A was weighed out and dissolved in 2 ml acetone. This stock solution was used to prepare the stability samples as follows:

Aliquots of 100 µl of stock solution were transferred to individual glass HPLC vials via a Hamilton syringe, with careful rinsing and drying of the syringe between each sample. The samples were dried down by air jet and then 0.5 ml of the appropriate test solvent system added. The solvent systems were tested in triplicate and are listed below:

1. 100% v/v acetone
2. 100% v/v acetonitrile
3. 100% v/v methanol
4. 70% v/v methanol: 30% w/w water
5. 100% w/w water Blank samples were also prepared in triplicate using 100 µl of acetone in place of the stock solution. The blank samples wore then dried down and 0.5 ml acetone added to each vial. The vials were all crimped, sealed with Parafilm® and placed at 4-8° C. for the duration of the stability study. HPLC analysis was performed on the samples on Day 0, Day 1, Day 5 and Day 14 of the stability study. The samples were prepared for the HPLC assay as described below:

The stability samples were removed from 4-8° C. and left at ambient temperature for 30 mins. Aliquots of 100 µl were transferred to fresh glass HPLC vials using a Hamilton syringe, with careful rinsing and drying of the syringe between each sample. To facilitate drying of the samples, 0.5 ml of acetone was added to each vial and then the samples were dried down by air jet. The samples were reconstituted with 1 ml of acetonitrile and analysed by HPLC using the chromatographic conditions specified above.

Thus, I3A is stable in acetone and acetonitrile at 4-8° C., as reflected in the predominance of peak 'b' for both solvents over the 14 days. In protic solvents, the formation of isomer 'a' and then isomer 'c' increases rapidly.

Stability at Various pH's

The stability of I3A was investigated at pH 4.5 in two buffers i.e. monopotassium phosphate/disodium phosphate and acetic acid/ammonium acetate for 24 h at room temperature. HPLC analysis showed that I3A is stable in both buffers at pH 4.5 i.e. there was still a predominance of isoform 'b' (FIG. 1) after 24 h.

The stability of I3A was investigated at pH 5.5, 6.5 and 7.0 over 14 days at room temperature, and was found to decrease with an increase in pH i.e. the formation of isoform 'a' and subsequently isoform 'c' occurs by Day 14.

Stability in DMSO

I3A was investigated for stability in DMSO at room temperature and at 37° C. over a 10 day time period. A control sample of I3A in acetonitrile was kept under the same conditions as the test sample. The samples were analysed by HPLC at the start of the experiment (Day 0), after 48 hours (Day 2) and again after 10 days.

The chromatographic conditions employed were as follows:

Column: Hypercarb (ThermoQuest, Phenomenex)
  (S/no. 3-34070)
Column length: 100×4.60 mm
Column temperature: 25° C.
Guard column: $C_{18}$ Columbus (Phenomenex)
  (S/no. 202678)
Guard column length: 50×4.60 mm
Mobile phase: 50% v/v Phosphate buffer pH 4.5/50% v/v acetonitrile
Flow rate: 1.0 ml/min
UV wavelength: 230 nm
Injection volume: 10 µl
Run time: 35 mins
Retention time: 15 mins, 24 mins I3A appears to be stable in DMSO at room temperature and at 37° C. for 10 days.

EXAMPLE 2

Isopropanol Gel pH 6.5

The stability of I3A 'b' in an isopropanol gel preparation (pH 6.5) was investigated. The protocol was as follows:

Composition of the Isopropanol Gel (pH 6.5)

| Excipient | Target mass | Actual mass | % w/w |
| --- | --- | --- | --- |
| Glycerin | 5.0000 g | 5.0000 g | 5.02 |
| Cyclomethicone | 0.5000 g | 0.5000 g | 0.50 |
| Isopropyl alcohol | 25.0000 g | 25.0000 g | 25.10 |
| Carbopol ® 934 | 0.3000 g | 0.3018 g | 0.30 |
| Propyl alcohol | 25.0000 g | 25.0000 g | 25.10 |
| Water | 43.7000 g | 43.7000 g | 43.87 |
| Ethanolamine | To pH 6.5 | 0.1000 g | 0.10 |
| Total: | | | 100 |

The Carbopol® was dispersed in the water and glycerin and dissolved by heating to 40° C. in a water bath. The propyl alcohol was then added to this solution. The cyclomethicone was dissolved in the isopropyl alcohol and this second solution was mixed well with the Carbopol® solution, and then water was added, with stirring, to 100%. The pH of the gel was brought to 6.5 with the dropwise addition of ethanolamine. The isopropanol gel was stored at 2-8° C. until use.

To investigate the stability of I3A 'b' in isopropanol gel (pH 6.5), a 0.02% (w/w) I3A 'b'/isopropanol gel formulation was prepared and divided into three samples for storage at 2-8° C., RTP and 40° C. At regular time points the samples were analysed in duplicate for the stability of I3A 'b' in terms of the formation of isoform 'a', with the results given in FIG. 2. I3A 'b' rearranges to isoform 'a' and subsequently isoform 'c'. This can possibly be attributed to the higher pH and presence of water in the isopropanol gel facilitating this conversion of I3A 'b' to isoforms 'a' and 'c'.

I3A 'b' in 30% w/w Isopropyl Alcohol/Citrate Buffer pH 3.0

The stability of I3A 'b' (Batch no. 240902) in 30% w/w IPA/citrate buffer (pH 3) when stored at 2-8° C., and 40° C. was investigated in duplicate, with the results given in FIG. 3.

Preservatives

Various preservatives were investigated for their suitability for use in the formulations of I3A 'b' at concentrations likely to pass a preservative efficacy test. Initially the preservatives were prepared in citrate buffer (pH 3) and analysed by HPLC to check for peaks in the chromatograms that might interfere with the assay for I3A isoforms. The results are summarised in Table 5.

TABLE 5

| Preservative | % w/w | Comments |
|---|---|---|
| Benzyl alcohol | 1.0 | No interfering peaks |
| Methyl paraben (M.P.) | 0.2 | Large peak over isoform 'a' region |
| Propyl paraben (P.P.) | 0.02 | Large peak over isoform 'a' region |
| M.P./P.P. | 0.2/0.02 | Large peak over isoform 'a' region |
| Phenoxyethanol | 1.0 | Small peak over isoform 'a' region |
| Citrate buffer control | 0 | No interfering peaks |

It is not desirable to have many interfering peaks in the chromatogram from the preservatives, as this leads to difficulties in the analysis of the drug in formulations, and could necessitate the introduction of a separate assay for the preservatives.

I3A 'b' (0.05% w/w) was dissolved separately in the preservatives selected (benzyl alcohol and phenoxyethanol), stored at 2-8° C. RTP and 40° C. and checked for stability in duplicate in terms of the formation of isoform 'a' at regular intervals. The results of this stability study are given in FIGS. 4 and 5.

The results indicate that benzyl alcohol is the most suitable preservative of those tested.

Preparation of I3A 'b' Formulations

The following three formulations and their respective placebos were prepared:
A. 0.1% (w/w) I3A 'b'/macrocetyl ether cream with 1.0% (w/w) benzyl alcohol as preservative
B. 0.1% (w/w) I3A 'b'/30% (w/w) IPA/1.5% (w/w) HEC/1.0% (w/w) benzyl alcohol/citrate pH 3
C. 0.1% (w/w) I3A 'b'/9.5% (w/w) cyclomethicone/9.5% (w/w) IPM/1.0% (w/w) benzyl alcohol/Elastomer 10

A stock solution of I3A 'b' was prepared in benzyl alcohol (Table 6) and this stock was used to prepare the formulations. For the placebos, benzyl alcohol alone was used in place of the I3A 'b'/benzyl alcohol stock. The accurate masses of the components of the I3A 'b' formulations are detailed in Tables 7-9. The formulations and their respective placebos were prepared as follows:

Formulation A: I3A 'b'/Macrocetyl Ether Cream

The macrocetyl ether emulsifying ointment was accurately weighed out into a glass vial and then melted in a water bath at 60° C. Freshly prepared citrate buffer (pH 3) was accurately weighed into a separate glass vial, warmed in the water bath and then gradually incorporated into the molten emulsifying ointment with constant stirring until cool. This process produced the macrocetyl ether cream. To prepare the formulation, I3A 'b' in benzyl alcohol was accurately weighed out into a glass vial and the macrocetyl ether cream was gradually and accurately weighed out onto this, with constant stirring.

Formulation B: I3A 'b'/30% IPA Gel

The I3A 'b'/benzyl alcohol was accurately weighed out into a glass vial. The remaining components were accurately weighed onto this solution in the order of IPA, then citrate buffer and then HEC, with vigorous mixing between each addition.

Formulation C: I3A 'b'/Silicones

The I3A 'b'/benzyl alcohol was accurately weighed out into a glass vial. The remaining components were accurately weighed onto this solution in the order of Elastomer 10, then cyclomethicone and then IPM, with vigorous mixing between each addition.

Formulation Analysis

The formulations were analysed at the start of the study to confirm the concentration of I3A 'b' (w/w) in the formulations and were found to be ca 0.1% (w/w) I3A 'b'. Of this total I3A 'b' content, there was less than 0.7% of isoform 'a' and no isoform 'c' in the formulations. The formulations were checked for the appearance of isoform 'a' by the time of the conclusion of the study and were shown to have less than 0.3% of isoform 'a' when stored at 2-8° C. Isoform 'c' was not detected in any of the formulations.

TABLE 6

Stock solution I3A 'b'/benzyl alcohol

| | Target mass | Actual mass | % w/w |
|---|---|---|---|
| I3A 'b' (Batch No. 240902) | 0.0650 g | 0.0650 g | 0.15 |
| Benzyl alcohol | 0.6500 g | 0.6547 g | 99.85 |
| Total: | 0.7150 g | 0.7197 g | 100.00 |

TABLE 7

Formulation A

| | Formulation | | | Placebo | | |
|---|---|---|---|---|---|---|
| Excipients for base cream | Target mass | Actual mass | % w/w | Target mass | Actual mass | % w/w |
| Macrocetyl ether emulsifying ointment | 7.5000 g | 7.5015 g | 30.00 | 6.0000 g | 6.0589 g | 30.50 |
| Citrate buffer | 17.5000 g | 17.5030 g | 70.00 | 13.8000 g | 13.8049 g | 69.50 |
| Total: | 25.0000 g | 25.0045 g | 100 | 19.8000 g | 19.8638 g | 100 |
| Macrocetyl ether base cream | 19.8000 g | 19.8860 g | 98.96 | 19.8000 g | 19.8638 g | 98.99 |
| I3A 'b'/benzyl alcohol | 0.2000 g | 0.2088 g | 1.04 | 0 | 0 | 0 |
| Benzyl alcohol only | 0 | 0 | 0 | 0.2000 g | 0.2020 g | 1.01 |
| Total: | 20.0000 g | 20.0948 g | 100.00 | 20.0000 g | 20.0658 g | 100.00 |

TABLE 8

Formulation B

| Excipients | Formulation | | | Placebo | | |
|---|---|---|---|---|---|---|
| | Target mass | Actual mass | % w/w | Target mass | Actual mass | % w/w |
| I3A 'b'/benzyl alcohol | 0.2000 g | 0.2035 g | 1.02 | 0 | 0 | 0 |
| Benzyl alcohol only | 0 | 0 | 0 | 0.2000 g | 0.2019 g | 1.01 |
| IPA | 6.0000 g | 6.0027 g | 29.97 | 6.0000 g | 6.0002 g | 29.99 |
| Citrate buffer pH 3 | 13.5000 g | 13.5158 g | 67.49 | 13.5000 g | 13.5018 g | 67.49 |
| HEC | 0.3000 g | 0.3040 g | 1.52 | 0.3000 g | 0.3029 g | 1.51 |
| Total: | 20.0000 g | 20.0260 g | 100 | 20.0000 g | 20.0068 g | 100 |

TABLE 9

Formulation C

| Excipients | Formulation | | | Placebo | | |
|---|---|---|---|---|---|---|
| | Target mass | Actual mass | % w/w | Target mass | Actual mass | % w/w |
| I3A 'b'/benzyl alcohol | 0.2000 g | 0.2011 g | 1.00 | 0 | 0 | 0 |
| Benzyl alcohol only | 0 | 0 | 0 | 0.2000 g | 0.2109 g | 1.05 |
| Cyclomethicone | 1.9000 g | 1.9040 g | 9.51 | 1.9000 g | 1.9026 g | 9.49 |
| IPM | 1.9000 g | 1.9068 g | 9.53 | 1.9000 g | 1.9156 g | 9.56 |
| Elastomer 10 | 16.0000 g | 16.0026 g | 79.96 | 16.0000 g | 16.0099 g | 79.89 |
| Total: | 20.0000 g | 20.0145 g | 100 | 20.0000 g | 20.0390 g | 100 |

Stability of I3A Isoforms in the Assay Solvent Systems over 72 h

The stability of I3A isoforms 'a', 'b' and 'c' in the three sample systems over 72 h (equivalent to the maximum possible length of time the samples might be held in the autosampler during a long HPLC analytical run) was confirmed as follows. Standards of the three isoforms of I3A (approximately 1.00 μg/ml) were freshly prepared in acetonitrile, acetonitrile/citrate buffer (pH 3) and acetonitrile/ammonium acetate buffer (pH 4.5) and analysed immediately by HPLC. The standards were then each divided into three equal volumes and placed at 2-8° C., room temperature and 40° C. for 72 h and were then again analysed by HPLC. The results of this study are presented in Table 10. The largest conversion of I3A 'b' to isoform 'a' at room temperature occurred with the sample prepared in 100% v/v acetonitrile whereas the I3A 'b' standard in acetonitrile/citrate (pH 3) showed very little conversion to isoform 'a' even at 40° C., suggesting that this solvent system might be the most appropriate for ensuring the samples remain stable over the sampling time.

TABLE 10

Stability of isoforms 'a', 'b' and 'c' in different solvent systems

Acetonitrile

| Time (h) | Isoform 'a' | | | Isoform 'b' | | | Isoform 'c' | | |
|---|---|---|---|---|---|---|---|---|---|
| | % 'a' | % 'b' | % 'c' | % 'a' | % 'b' | % 'c' | % 'a' | % 'b' | % 'c' |
| 0 | 96.82 | 2.24 | 0.29 | 0.39 | 99.27 | 0 | 1.28 | 0.41 | 97.30 |
| 72 h 2-8° C. | 90.63 | 5.71 | 2.55 | 3.94 | 95.45 | 0 | 1.62 | 0 | 96.69 |
| 72 h RTP | 86.58 | 7.8 | 3.65 | 5.83 | 93.51 | 0 | 1.55 | 0.27 | 97.19 |
| 72 h 40° C. | 16.36 | 47.01 | 35.74 | 15.52 | 83.35 | 0 | 0.6 | 0 | 97.09 |

Acetonitrile/Sodium acetate buffer (pH 4.5)

| Time (h) | Isoform 'a' | | | Isoform 'b' | | | Isoform 'c' | | |
|---|---|---|---|---|---|---|---|---|---|
| | % 'a' | % 'b' | % 'c' | % 'a' | % 'b' | % 'c' | % 'a' | % 'b' | % 'c' |
| 0 | 96.65 | 2.16 | 0.23 | 0.34 | 98.88 | 0.01 | 1.34 | 0.45 | 97.02 |
| 72 h 2-8° C. | 96.47 | 2.83 | 0 | 0.63 | 99.02 | 0 | 1.41 | 0.27 | 97.17 |
| 72 h RTP | 95.25 | 4.22 | 0 | 1.16 | 98.41 | 0 | 0.83 | 0 | 97.97 |
| 72 h 40° C. | 82.51 | 16.62 | 0 | 6.35 | 93.13 | 0 | 0 | 0 | 97.75 |

Acetonitrile/Citrate buffer (pH 3)

| Time (h) | Isoform 'a' | | | Isoform 'b' | | | Isoform 'c' | | |
|---|---|---|---|---|---|---|---|---|---|
| | % 'a' | % 'b' | % 'c' | % 'a' | % 'b' | % 'c' | % 'a' | % 'b' | % 'c' |
| 0 | 97.91 | 1.63 | 0 | 0.13 | 99.64 | 0 | 1.12 | 0.20 | 98.41 |
| 72 h 2-8° C. | 98.31 | 1.46 | 0 | 0.18 | 99.49 | 0 | 0.87 | 0.16 | 98.84 |
| 72 h RTP | 98.84 | 1.08 | 0 | 0.13 | 99.76 | 0 | 0.53 | 0 | 99.24 |
| 72 h 40° C. | 98.13 | 1.79 | 0 | 0.34 | 99.63 | 0 | 0 | 0 | 98.7 |

EXAMPLE 3

A pH stability study of I3A 'b' in IPA gels prepared with citrate buffer in the pH range 2.5 to 4.0 was conducted at 2-8° C. and 40° C. (accelerated stability).

Materials

| Materials | Supplier |
|---|---|
| I3A 'b' (ingenol angelate) Batch No. 070303 Batch No. 0319 | Peplin Limited, Australia |
| Sodium dihydrate citrate (USP grade) Batch R009243 | Raught Ltd, UK |
| Citric acid monohydrate (USP grade) Batch R11115 | |
| Glacial acetic acid Lot K2953917 | BDH Laboratory Supplies, UK |
| Sodium acetate Lot TA1044704 | |
| Benzyl alcohol (USP grade) Lot No. K31593981 | Merck, Germany |
| Isopropyl alcohol (USP grade) Lot No. K31802995310 | |
| Natrosol ® 250 HHX Batch No. Z-0177 | Honeywell and Stein, UK |
| Acetonitrile-HPLC grade | Fisher Chemicals, UK |
| Deionised water | MilliQ, UK |

Methods

Preparation of I3A 'b' gels and placebos using citrate buffer in the pH range 2.5 to 4.0.

The compositions of the active and placebo IPA gels prepared for the pH range stability study are given in Tables 11 and 12, respectively. Large quantities of placebo were prepared to facilitate the measurement of the pH of the placebo gels at Time 0. Smaller quantities of the active gel i.e. 30 g of each were prepared since the amount of drug available for the study was limited. Previous stability studies conducted on the I3A IPA gel, in which the apparent pH of the placebo and active gel were monitored over 12 months, have shown that there is no noticeable difference between the two. Furthermore, the same apparent pH was measured for both the active and placebo gels. Thus, only the pH of the placebo gels was measured, to determine the apparent pH of the gels at the start of the stability study. After overnight hydration, the gels were analysed for the T=0 time point and the apparent pH values of the placebos were measured. The samples were divided equally into 7 ml soda glass vials to avoid temperature cycling of the material when sampling at the different time points and the vials were stored at 2-8° C. and 40° C. (accelerated stability), respectively.

TABLE 11

Composition of Active IPA gels prepared with citrate buffer in the pH range 2.5 to 4.0

| Excipient | Target mass (g) | citrate buffer pH 2.5 | Actual % w/w | citrate buffer pH 2.75 | Actual % w/w | citrate buffer pH 3.0 | Actual % w/w | citrate buffer pH 3.5 | Actual % w/w | citrate buffer pH 4.0 | Actual % w/w |
|---|---|---|---|---|---|---|---|---|---|---|---|
| I3A BN 070303 | 0.0300 | 0.03004 | 0.10 | 0.03003 | 0.10 | 0.03005 | 0.10 | 0.03003 | 0.10 | 0.03000 | 0.10 |
| Benzyl alcohol | 0.2700 | 0.27112 | 0.90 | 0.27055 | 0.90 | 0.27060 | 0.90 | 0.27278 | 0.91 | 0.27193 | 0.91 |
| IPA | 9.0000 | 9.00340 | 30.00 | 9.01909 | 30.04 | 9.00107 | 30.00 | 9.00243 | 30.00 | 9.00158 | 30.00 |
| Citrate buffer | 20.2500 | 20.25235 | 67.50 | 20.25345 | 67.46 | 20.25086 | 67.50 | 20.25061 | 67.49 | 20.2533 | 67.49 |
| HEC HHX | 0.4500 | 0.45063 | 1.50 | 0.45041 | 1.50 | 0.45031 | 1.50 | 0.45053 | 1.50 | 0.45041 | 1.50 |
| Total | 30.0000 | 30.00754 | 100.00 | 30.02353 | 100.00 | 30.00289 | 100.00 | 30.00638 | 100.00 | 30.00722 | 100.00 |

TABLE 12

Composition of Placebo IPA gels prepared with citrate buffer in the pH range 2.5 to 4.0

| Excipient | Target mass (g) | Citrate buffer pH 2.5 | Actual % w/w | citrate buffer pH 2.75 | Actual % w/w | citrate buffer pH 3.0 | Actual % w/w | citrate buffer pH 3.5 | Actual % w/w | citrate buffer pH 4.0 | Actual % w/w |
|---|---|---|---|---|---|---|---|---|---|---|---|
| Benzyl alcohol | 0.9000 | 0.9070 | 0.91 | 0.9003 | 0.90 | 0.9046 | 0.90 | 0.9036 | 0.90 | 0.9042 | 0.90 |
| IPA | 30.0000 | 30.0035 | 30.00 | 30.0016 | 30.00 | 30.0233 | 30.00 | 30.0136 | 30.00 | 30.0201 | 30.01 |
| Citrate buffer | 67.6000 | 67.6107 | 67.59 | 67.6108 | 67.60 | 67.6400 | 67.59 | 67.6211 | 67.60 | 67.6139 | 67.58 |
| HEC HHX | 1.5000 | 1.5022 | 1.50 | 1.5065 | 1.50 | 1.5086 | 1.51 | 1.5031 | 1.50 | 1.5064 | 1.51 |
| Total | 100.0000 | 100.0234 | 100.00 | 100.0192 | 100.00 | 100.0765 | 100.00 | 100.0414 | 100.00 | 100.0446 | 100.00 |

Measurement of the apparent pH of IPA placebo gels prepared using citrate buffer in the pH range 2-5 to 4.0

The apparent pH of the IPA placebo gels prepared using citrate buffer in the pH range 2.5 to 4.0 were measured using a Jenway 3320 pH meter.

Extraction of I3A from the IPA Gels

The drug was extracted from the IPA gels as follows. One gram of each of the gels or their respective placebos was accurately weighed into a 10 ml volumetric flask in duplicate or triplicate. The samples were first mixed with 1 ml of citrate buffer (pH 3) by vigorous and repetitive mixing on a vortex mixer set to maximum speed and then left shaking on an orbital shaker for 30 mins at 400 rpm. The volumetric flasks were then made up to the volume mark with HPLC-grade acetonitrile and the samples were again subjected to vigorous mixing by repetitive mixing on a vortex mixer set to maximum speed and then left shaking on an orbital shaker for 60 mins at 400 rpm. Aliquots were transferred to HPLC vials for analysis.

The extraction of I3A from the gel was performed in triplicate i.e. three separate weighing-outs with duplicate injections for the Time 0 and Time=three months (2-8° C. samples) points and in duplicate i.e. two separate weighing-outs with duplicate injections for the Time=one week and four weeks (40° C. samples).

HPLC Analysis

The analysis was performed using the following systems and conditions:

Instruments

Waters Alliance 2695 Separations Module (S/no. B98SM4209M)

Waters 2487 Dual λ Absorbance detector (S/no. M97487050N).

Waters Alliance 2695 D Separations Module (S/no. G98SM8039N)

Waters 2487 Dual λ Absorbance detector (S/no. L02487106M)

Empower Pro Empower™ Software

The chromatographic conditions employed were as follows:

Columns: Hypercarb (ThermoQuest, Phenomenex)
S/no. 3-34070 and S/no. 1034024A
Column length: 100×4.60 mm
Column temperature: ambient
Guard columns: $C_{18}$ Columbus (Phenomenex)
S/no. 202678 and S/no. 74554-7
Guard column length: 50×4.60 mm
Mobile phase: 50% v/v sodium acetate buffer pH 4.5/50% acetonitrile (v/v)
Flow rate: 1.0 ml/min
UV wavelength: 230 nm
Injection volume: 30 µl
Run time: 35 mins
Autosampler temperature: 8° C.±2° C.
Retention times: 13 mins±2 mins isoform 'a'; 22 mins±2 mins isoform 'b'; 23 mins±2 mins isoform 'c'; unassigned peak with relative retention time to isoform 'b' of 0.93±0.02.

Results

Measurement of the apparent pH of the placebo gels at Time 0

The results for the measurement of the apparent pH of the placebo gels are given in Table 13. No pH measurements were taken at any of the stability time points.

TABLE 13

Measurement of the apparent pH of placebo IPA gels (n = 1)

| pH of Citrate Buffer (±0.05) | Apparent pH of placebo gel |
|---|---|
| 2.50 | 3.07 |
| 2.75 | 3.34 |
| 3.00 | 3.62 |
| 3.50 | 4.22 |
| 4.00 | 4.74 |

Determination of Percentage Peak Purities of I3A Isoforms in the Active Gels

The percentage peak purities of I3A 'b' in the active gels at the start of the stability stud (T=0), and after one week of storage at 40° C., four weeks of storage at 40° C., and after three months storage at 2-8° C., are given in Tables 14, 15, 16 and 17, respectively. The percentage peak purity of I3A 'b' was greater than 98% whilst the percentage peak purity of isoform 'a' was less than 1.2% for all the gels after three months of storage at −28° C. For the accelerated stability study at 40° C., the greatest decrease in the percentage peak parity of 'b' over the four weeks was observed with the gel with apparent placebo value of 4.74. Since I3A 'b' has been shown to convert to isoform 'a', the formation of isoform 'a' was also examined as a stability marker. The increases in the percentage peak purities of isoform 'a' from Time 0 after one week and four weeks storage at 40° C., and after three months storage at 2-8° C. were calculated, with the results given in Table 18.

TABLE 14

Percentage peak purities of isoforms of I3A in the active gels (n = 3, mean ± standard deviation, UAP = unassigned peak, RRT = relative retention time) at Time 0

| pH of Citrate buffer (±0.05) | Apparent pH of placebo gel | Percentage peak purity | | | | |
|---|---|---|---|---|---|---|
| | | Isoform 'a' | Isoform 'b' | Isoform 'c' | UAP RRT to isoform 'b' 0.93 ± 0.02 | Total other UAPs |
| 2.50 | 3.07 | 0.44 ± 0.03 | 99.20 ± 0.11 | 0.00 ± 0.00 | 0.20 ± 0.04 | 0.16 ± 0.07 |
| 2.75 | 3.34 | 0.24 ± 0.06 | 99.70 ± 0.09 | 0.00 ± 0.00 | 0.02 ± 0.02 | 0.04 ± 0.04 |
| 3.00 | 3.62 | 0.52 ± 0.01 | 99.16 ± 0.06 | 0.00 ± 0.00 | 0.14 ± 0.02 | 0.19 ± 0.06 |
| 3.50 | 4.22 | 0.47 ± 0.02 | 99.36 ± 0.10 | 0.00 ± 0.00 | 0.09 ± 0.03 | 0.08 ± 0.04 |
| 4.00 | 4.74 | 0.44 ± 0.03 | 99.30 ± 0.10 | 0.00 ± 0.00 | 0.10 ± 0.01 | 0.16 ± 0.07 |

TABLE 15

Percentage peak purities of isoforms of I3A in the active gels (n = 2, mean ± range, UAP = unassigned peak, RRT = relative retention time) after one week of storage at 40° C.

| pH of Citrate buffer (±0.05) | Apparent pH of placebo gel | Percentage peak purity | | | | |
|---|---|---|---|---|---|---|
| | | Isoform 'a' | Isoform 'b' | Isoform 'c' | UAP RRT to isoform 'b' 0.93 ± 0.02 | Total other UAPs |
| 2.50 | 3.07 | 1.01 ± 0.02 | 98.83 ± 0.05 | 0.00 ± 0.00 | 0.04 ± 0.01 | 0.13 ± 0.03 |
| 2.75 | 3.34 | 0.53 ± 0.34 | 99.06 ± 0.06 | 0.00 ± 0.00 | 0.06 ± 0.01 | 0.35 ± 0.31 |
| 3.00 | 3.62 | 1.61 ± 0.05 | 98.26 ± 0.09 | 0.00 ± 0.00 | 0.05 ± 0.01 | 0.07 ± 0.04 |
| 3.50 | 4.22 | 2.56 ± 0.04 | 97.27 ± 0.22 | 0.00 ± 0.00 | 0.04 ± 0.04 | 0.12 ± 0.15 |
| 4.00 | 4.74 | 4.68 ± 0.03 | 95.12 ± 0.07 | 0.00 ± 0.00 | 0.08 ± 0.02 | 0.12 ± 0.04 |

TABLE 16

Percentage peak purities of isoforms of I3A in the active gels (n = 2, mean ± range, UAP = unassigned peak, RRT = relative retention time) after four weeks of storage at 40° C.

| pH of Citrate buffer (±0.05) | Apparent pH of placebo gel | Percentage peak purity | | | | |
|---|---|---|---|---|---|---|
| | | Isoform 'a' | Isoform 'b' | Isoform 'c' | UAP RRT to isoform 'b' 0.93 ± 0.02 | Total other UAPs |
| 2.50 | 3.07 | 2.70 ± 0.01 | 96.24 ± 0.09 | 0.00 ± 0.00 | 0.07 ± 0.02 | 0.99 ± 0.06 |
| 2.75 | 3.34 | 2.91 ± 0.02 | 96.44 ± 0.14 | 0.00 ± 0.00 | 0.06 ± 0.02 | 0.59 ± 0.11 |
| 3.00 | 3.62 | 4.74 ± 0.02 | 94.75 ± 0.12 | 0.00 ± 0.00 | 0.08 ± 0.02 | 0.44 ± 0.09 |
| 3.50 | 4.22 | 7.68 ± 0.02 | 92.01 ± 0.12 | 0.00 ± 0.00 | 0.07 ± 0.04 | 0.25 ± 0.08 |
| 4.00 | 4.74 | 13.34 ± 0.02 | 86.47 ± 0.14 | 0.00 ± 0.00 | 0.06 ± 0.03 | 0.13 ± 0.09 |

TABLE 17

Percentage peak purities of isoforms of I3A in the active gels (n = 3, mean ± standard deviation, UAP = unassigned peak, RRT = relative retention time) after three months of storage at 2-8° C.

| pH of Citrate buffer (±0.05) | Apparent pH of placebo gel | Percentage peak purity | | | | |
|---|---|---|---|---|---|---|
| | | Isoform 'a' | Isoform 'b' | Isoform 'c' | UAP RRT to isoform 'b' 0.93 ± 0.02 | Total other UAPs |
| 2.50 | 3.07 | 0.56 ± 0.01 | 99.34 ± 0.03 | 0.00 ± 0.00 | 0.00 ± 0.00 | 0.10 ± 0.03 |
| 2.75 | 3.34 | 0.20 ± 0.08 | 99.71 ± 0.13 | 0.00 ± 0.00 | 0.00 ± 0.00 | 0.09 ± 0.05 |
| 3.00 | 3.62 | 0.73 ± 0.01 | 99.15 ± 0.01 | 0.00 ± 0.00 | 0.00 ± 0.00 | 0.12 ± 0.01 |
| 3.50 | 4.22 | 0.91 ± 0.01 | 99.00 ± 0.01 | 0.00 ± 0.00 | 0.00 ± 0.00 | 0.09 ± 0.01 |
| 4.00 | 4.74 | 1.16 ± 0.09 | 98.73 ± 0.13 | 0.00 ± 0.00 | 0.00 ± 0.00 | 0.11 ± 0.05 |

TABLE 18

Calculated increase in percentage peak purities of I3A isoform 'a' from Time 0 in the IPA gels

| pH of Citrate buffer (±0.05) | Apparent pH of placebo gel | Increase in percentage peak purity isoform 'a' from Time 0 (Table 5): | | |
|---|---|---|---|---|
| | | Stored at 40° C. | | Stored at 2-8° C. |
| | | T = 1 week | T = 4 weeks | T = 3 months |
| 2.50 | 3.07 | 0.57 | 2.26 | 0.12 |
| 2.75 | 3.34 | 0.29 | 2.67 | 0.00 |
| 3.00 | 3.62 | 1.09 | 4.22 | 0.21 |
| 3.50 | 4.22 | 2.09 | 7.21 | 0.44 |
| 4.00 | 4.74 | 4.24 | 12.90 | 0.72 |

The data suggests that the pH on the formation of isoform 'a' even when the gel is stored at 2-8° C. for three months. An increase in the percentage peak area of isoform 'a' of 0.21% was measured with the gel prepared with citrate buffer of pH 3.00 compared to an increase of 0.44% in the percentage peak area of isoform 'a' for the gel prepared with citrate buffer of pH 3.5. By T=4 weeks at 40° C. the differences between the gels in terms of the increases in the percentage peak purities of isoform 'a' were amplified.

EXAMPLE 4

Oil Formations

Materials

| Material | Supplier |
| --- | --- |
| I3A Batch No. 0302 | Peplin Limited, Australia |
| Benzyl alcohol Ph Eur, BP, NF Batch No. K31593981 301 | Merck KGaA, Germany |
| Crodamol GTC/C (Medium chain triglycerides) Batch No. GE03907 | Croda, Singapore |
| Sodium dihydrate citrate Lot No. 27833.261 | Merck Chemicals, UK |
| Citric acid Lot No. 111K0142 | Sigma Chemical Co., UK |
| Glacial acetic acid Sodium acetate Lot 102363P | BDH Laboratory Supplies, UK |
| Acetonitrile-HPLC grade Trifluoroacetic acid (TFA) Lot no. 0392851 | Fisher Scientific, UK |
| Deionised water | Millipore, UK |

Methods

Selection of Suitable Oils/Excipients

Sesame oil, fractionated coconut oil (medium chain triglycerides), soybean oil, corn oil, and peanut oil, were identified as vehicles for parenteral administration. Each can be used up to a level of 100%.

Other excipients, which may be included in parenteral oil formulations, are shown below, together with the maximum concentrations used.

| Excipient (use) | Maximum concentration used (%) |
| --- | --- |
| Benzyl alcohol (solubiliser/preservative) | 3.0 |
| Ethanol (solubiliser) | 70 |
| Butylated hydroxyanisole (antioxidant) | 0.03 |
| Butylated hydroxytoluene (antioxidant) | 0.03 |

Preparation of I3A and Placebo Formulations for Preliminary Stability Studies

Sterilisation of Fractionated Coconut Oil

Approximately 50 g of the fractionated coconut oil (CRODAMOL GTC/C) was weighed into a 100 ml conical flask (borosilicate glass), stoppered (borosilicate glass stopper) and placed inside a pre-heated oven (Gallenkampf Hot box Oven with fan, Size 2) at 173±5° C. for 1 h. After this procedure, the oil was allowed to cool to room temperature before use.

Addition of I3A to the Sterilised Oil

Approximately 10 mg of I3A was accurately weighed into a 28 ml glass vial and added to approximately 200 mg of benzyl alcohol (exact weight noted), which had previously been filtered through a 0.22 μm MILLEX-GV filter. This mixture was periodically vortexed for approximately 2 h until the I3A had dissolved in the benzyl alcohol. To this mixture approximately 9.79 g of the sterilized oil was added and vortexed for approximately 5 mins until a homogeneous solution was obtained. The placebo was prepared in a similar manner except that approximately 9.80 g (as opposed to 9.79 g) of the sterilised oil (exact weight noted) was used to compensate for I3A. Exact weights and percentage compositions are shown in Tables 19 and 20 for active (I3A) and placebo formulations.

TABLE 19

Target and actual amounts (and % w/w) for the I3A oil formulation

| | Target weight | Target % w/w | Actual weight | *Actual % w/w |
| --- | --- | --- | --- | --- |
| I3A | 10 mg | 0.10 | 10.15 mg | 0.101 |
| Benzyl alcohol | 200 mg | 2.0 | 200.16 mg | 1.998 |
| Fractionated coconut oil | 9.79 g | 97.9 | 9.80854 g | 97.901 |
| Total | 10 g | 100 | 10.01885 g | 100 |

*Rounded up to 3 d.p.

TABLE 20

Target and actual amounts (and % w/w) for the placebo oil formulation

| | Target weight | Target % w/w | Actual weight | *Actual % w/w |
| --- | --- | --- | --- | --- |
| Benzyl alcohol | 200 mg | 2.0 | 200.89 mg | 1.971 |
| Fractionated coconut oil | 9.8 g | 98.0 | 9.99313 g | 98.029 |
| Total | 10 g | 100 | 10.19402 g | 100 |

*Rounded up to 3 d.p.

Storage Conditions for I3A and Placebo Formulations

Aliquots of each formulation (placebo or active) were dispensed into 2 ml screw cap amber glass vials (borosilicate glass), sealed and stored at two storage conditions namely 2-8° C. and 25±2° C. The formulations were tested using the method described below at storage times up to and including one month.

Preliminary Stability of I3A in Fractionated Coconut Oil

Table 21 summarises the stability of I3A in fractionated coconut oil stored at 2-8° C. and 25° C. over 43 days. The stability data indicates that there appears to be no increase in the percentage of isoform 'a' during storage at 2-8 and 25° C. after 43 days, comparable to the percentage of isoform 'a' from a fresh batch of I3A at t=0 and t=43 days.

TABLE 21

The percentage of isoform 'a' as a percentage of isoform 'a' and I3A 'b' stored at two conditions for 43 days.

| | % I3A 'a' |
| --- | --- |
| Fresh sample I3A in Acetonitrile at time zero | 2.50 |
| Time 0 | 1.90 |
| Time 5 days (2-8° C.) | 1.86 |
| Time 5 days (25° C.) | 1.97 |
| Time 20 days (2-8° C.) | 1.94 |
| Time 20 days (25° C.) | 1.93 |
| Time 28 days (2-8° C.) | 1.93 |
| Time 28 days (25° C.) | 1.94 |
| Time 43 days (2-8° C.) | 1.95 |
| Time 43 days (25° C.) | 1.91 |
| Fresh sample I3A in Acetonitrile at time 43 days | 2.14 |

Results

There was no significant difference (p>0.05) in peak area and retention time of I3A isoforms 'a' and 'b' between the samples injected in acetonitrile or acetonitrile/oil.

From the list of oils available two were deemed suitable for formulation of I3A namely, fractionated coconut oil and sesame oil. The recommended sterilisation of sesame oil is 2 h a 170° C. whereas for fractionated coconut oil it is 1 h at 170° C. This has advantages with regards to the amount of time and energy spent preparing the formulation. Due to the instability of I3A to heat (experimentally proven, data not shown), the oil has to be sterilised separately and the I3A added aseptically (filtered) as a solution dissolved in benzyl alcohol. A filter medium has been identified to be suitable for filtration of the I3A/benzyl alcohol mixture namely a 0.22 μm MILLEX-GV filter, however, the adsorption of I3A on the filter membrane still requires investigation. If desired, due to the relatively low viscosity of this oil (approximately 30 mPas compared to sesame oil which has a viscosity of approximately 44 mPas) the formulation could also be prepared in situ with I3A/benzyl alcohol and the complete formulation sterilised by filtration.

EXAMPLE 5

Oral Formulations

A number of excipients were selected for the buccal formulations, and 17 non-aqueous formulations were prepared and visually evaluated for consistency and solvation.

A variety of polymers was as potential mucoadhesive vehicles. Due to the inherent instability of I3A in aqueous systems, the formulations investigated were non-aqueous, substituting glycerol and polyethylene glycol (PEG) for the aqueous phase.

Materials

| Material | Supplier |
| --- | --- |
| I3A Batch No. 0319 | Peplin Limited, Australia |
| Benzyl alcohol Ph Eur, BP, NF Batch No. K31593981 301 | Merck KGaA, Germany |
| Polyethylene glycol 400 (PEG 400) Batch no. 8.17003.1000 | Merck KgaA, Germany |
| Glycerol Batch no. 121K0152 | Sigma Chemical Co., UK |
| Citric acid Batch No. 111K0142 | |
| Porcine Mucin - Type III Batch no. 68H7480 | |
| Carbopol 934 Batch no. 15885 | Serva, Germany |
| Methylcellulose (MC) Batch no. 404006/1 | Fluka, UK |
| Hydroxyethylcellulose HX (HEC) | Hercules, USA |
| Hydroxypropylcellulose (HP) | |
| HPLC grade Methanol | Fisher Scientific, UK |
| Trifluoroacetic acid (TFA) Lot no. 0392851 | |
| Deionised water (18.2M ohm cm) | Millipore, UK |

Methods

Preliminary Visual Screening of Placebo Formulations

Seventeen placebo formulations were initially prepared and visually screened for consistency and solvation (Table 22). Briefly, the required amounts of PEG 400 and carbopol 934 were stirred in 28 ml glass vials for 10 mins with a spatula and the other ingredients were added in the following order, glycerol, benzyl alcohol and methylcellulose or HEC or HPC. The formulations were then mixed with a Silverson 14RT stirrer at approximately 10,000 rpm for approximately 2-3 mins. All the mixed placebo formulations were left to solvate overnight (>24 h) before visual screening.

TABLE 22

Composition of placebo formulations for visual assessment

Formulation Number/% w/w excipient added

| Excipient | 1 | 2 | 3 | 4 | 5 | 6 | 7 | 8 | 9 | 10 | 11 | 12 | 13 | 14 | 15 | 16 | 17 |
| --- | --- | --- | --- | --- | --- | --- | --- | --- | --- | --- | --- | --- | --- | --- | --- | --- | --- |
| PEG 400 | 26.0 | 25.0 | 26.0 | 26.5 | 25.0 | 26.0 | 26.8 | 26.5 | 27.0 | 27.5 | 27.0 | 28.0 | 26.5 | 26,.5 | 26.0 | 26.5 | 26.0 |
| Glycerol | 70.0 | 70.0 | 70.0 | 70.0 | 70.0 | 70.0 | 70.0 | 70.0 | 70.0 | 70.0 | 70.0 | 70.0 | 70.0 | 70.0 | 70.0 | 70.0 | 70.0 |
| Benzyl alcohol | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Methyl-cellulose | 1.0 | 1.0 | | | | | 0.2 | 2.0 | 1.0 | 1.0 | | | | 1.0 | 1.5 | | |
| Carbopol | 2.0 | 3.0 | 2.0 | 1.5 | 3.0 | 2.0 | 2.0 | 0.5 | 1.0 | 0.5 | 1.0 | 0.5 | 0.5 | 1.5 | 1.5 | 1.5 | 1.5 |
| HEC | | | 1.0 | 1.0 | 1.0 | | | | | | | | | | | | |
| HPC | | | | | | 1.0 | | | | | 1.0 | 0.5 | 2.0 | | | 1.0 | 1.5 |

Rheological Screening of Placebo Formulations (Mucoadhesion)

One approach to the study of mucoadhesion is rheological characterisation of mucoadhesive interface. It is based on the assumption that the extent of interpenetration can be detected by measuring differences in rheological parameters between polymer gels and their mixtures with mucin. The synergistic increase in viscosity has been proposed as an index of bioadhesion bond strength. From the visual screening, five placebo formulations were chosen based on viscosity and solvation, for further rheological assessment using porcine mucin. The formulations chosen are listed in Table 23.

TABLE 23

Formulations chosen for rheological screening

| Excipient | Formulation Number/% w/w excipient added | | | | |
|---|---|---|---|---|---|
| | 4 | 14 | 15 | 16 | 17 |
| PEG 400 | 26.5 | 26,.5 | 26.0 | 26.5 | 26.0 |
| Glycerol | 70.0 | 70.0 | 70.0 | 70.0 | 70.0 |
| Benzyl alcohol | 1.0 | 1.0 | 1.0 | 1.0 | 1.0 |
| Methylcellulose | | 1.0 | 1.5 | | |
| Carbopol | 1.5 | 1.5 | 1.5 | 1.5 | 1.5 |
| HEC | 1.0 | | | | |
| HPC | | | | 1.0 | 1.5 |

Preparation of Samples for Rheological Assessment
Preparation of Porcine Mucin

Briefly, 15 g of porcine mucin powder was weighed into a beaker and made up to 150 g using deionised water to give a final concentration of 10% w/w mucin. This was allowed to hydrate at 2-8° C. for approximately 2-3 h. The hydrated mucin was further diluted with deionised water to obtain a final concentration of 5% w/w mucin in deionised water. This was left to hydrate overnight in the fridge at 2-8° C.

Preparation of Formulation/Mucin Mix

The selected formulations (Table 23) were prepared as described above. To each of the formulations an equal weight of 10% w/w mucin was added and gently stirred with a spatula. This was left to hydrate at 2-8° C. overnight. In addition, the selected formulations were also diluted (50:50 w/w) with deionised water and left to hydrate overnight in the fridge at 2-8° C.

Dynamic (Oscillatory) Rheology Testing Procedure

The rheological screening was carried out using a Car-rimed $CSL^2$ rheometer. Approximately 0.5 g of the test sample was placed between the platform and parallel plate geometry. Once the sample was compressed between the platform and plate any excess sample was carefully removed using a spatula at right angles to the geometry. Each sample was tested a total of five times resulting in mechanical spectra. The resultant parameters obtained G', G" and tan δ were used to assess the mucoadhesive strength of the formulations, where G' is the elastic modulus, G" the viscous modulus and tan δ the ratio of G' to G".

Optimisation and Preparation of Selected Active and Placebo Formulations

Following rheological testing two formulations was selected for further optimisation (Formulation 16 and 17) with respect to preparation of batch of formulation for stability. The optimised manufacturing process was used to prepare batches of active (containing I3A) and placebo formulations (25 g of each). FIG. 6 shows the preparation of the active and placebo Formulation 16 with the target amounts of excipients/drug used. Briefly, the required amount of carbopol 934 was added to PEG 400 in a borosilicate bottle and heated to 50° C. for approximately 2 h until the mixture was fully solvated. This mixture was cooled to room temperature; the required amount of glycerol added and the mixture was heated to approximately 60° C. in a water bath for 2 h until a homogenous paste was formed. The required amount of HEC was added and stirred into the cooled mixture using a Silverson L4RT mixer set at approximately 10,000 rpm for 2-3 minutes. This mixture was then allowed to fully solvate overnight (ca. 12 h) at room temperature. As FIG. 6 shows this produced a 'Base formulation'.

The active formulation was prepared by initially dissolving the I3A in benzyl alcohol. The required amount of I3A/benzyl alcohol was added to the solvated base formulation and gently stirred with a spatula to give a final concentration of 0.1% w/w I3A. Similarly, the placebo formulation was prepared by adding the benzyl alcohol to the solvated mixture and gently stirred. Formulation 17 was prepared in a similar manner. Table 24 shows the target % w/w of excipients/I3A in the active and placebo formulations.

Approximately 1 g of the placebo and active formulations were aliquoted into 2 ml screw cap vials and placed on stability at 2-8° C., 25° C. and 40° C. (the latter temperature was utilised for short term accelerated stability studies).

TABLE 24

Target % w/w (to 1 d.p.) in the optimised active and placebo formulations

| Excipient/drug | Formulation 16 | | Formulation 17 | |
|---|---|---|---|---|
| | Active | Placebo | Active | Placebo |
| PEG 400 | 26.5 | 26.5 | 26.0 | 26.0 |
| Carbopol | 1.5 | 1.5 | 1.5 | 1.5 |
| Glycerol | 69.9 | 70.0 | 69.9 | 70.0 |
| HPC | 1.0 | 1.0 | 1.5 | 1.5 |
| Benzyl alcohol | 1.0 | 1.0 | 1.0 | 1.0 |
| I3A (0319) | 0.1 | | 0.1 | |

Analysis of I3A in Formulation
Extraction of I3A from the Active Formulation

For the purpose of drug product evaluation an extraction method was set up to evaluate the degradation of I3A 'b' to isoform 'a' (chromatographic peak purity). The extraction of I3A from the active formulation was as follows (the same procedure was also used for the placebo formulation). Briefly, about 1 g of the formulation was accurately weighed into a 10 ml volumetric flask followed by 1 ml of citrate buffer (pH 3). This was gently shaken by hand for approximately 5 mins until homogeneous and made up to volume with HPLC grade methanol. The flask was then shaken on a mechanical shaker for approximately 2 h. The contents of the flask were then transferred to a 15 ml polypropylene tube and centrifuged for 5 mins at 2200 rpm. The supernatant was aliquoted into HPLC vials and analysed.

Preliminary recovery data (not shown) indicated that ca. 80% or more of I3A 'b' was recovered from the active formulation and more significantly, there was no interference from any of the excipients in the formulation.

HPLC Method

The method of analysis for the analysis of I3A in the buccal formulation is shown below.
Column: Symmetry $C_{18}$-5 μm (Waters)
  (S/no. T636515 07, P/no. WAT054205)
Column length: 150×3.90 mm
Column temperature: 30° C.
Guard column: Symmetry $C_{18}$-5 μm (Waters)
  (P/no. WAT054225)
Guard column length: 20×3.90 mm
Mobile phase: 0.02% v/v TFA in water (A); 0.02% v/v TFA in Acetonitrile (B)
  A:B; 50:50 (starting composition)
  (GRADIENT, see table below)
Flow rate: 1.0 ml/min
UV wavelength: 230 nm (PDA)

Injection volume: 10
Run time: 20 mins
Autosampler temperature: 8° C.

Samples and placebos were tested at time zero. At approximately 1-2 weeks, samples stored at 40° C. were also tested in order to obtain some accelerated stability data.

Results

Visual Screening

The visual screening as carried out qualitatively and provided a relatively efficient method of pre-screening a number of formulations with regard to viscosity and solvation. Placebo formulations were assessed by two independent assessors and rejected on the basis that the viscosity was either too high or too low. Furthermore, any formulation, which had not completely solvated, was also rejected. It was quite apparent that according to the method of preparation a carbopol 934 concentration greater than 1.5% w/w produced non-aqueous gels which were too viscous and/or not fully solvated. A reduction in the amount of carbopol 934 to 0.5% w/w and addition of methylcellulose at a concentration of 2.0% w/w produced a gel of low viscosity. However, increasing the carbopol 934 concentration to 1.0% w/w and concomitantly reducing the methylcellulose concentration to 1.0% w/w still gave a gel which was low in viscosity. Front the visual observations it would appear that the addition of methylcellulose did not influence the viscosity to a great extent compared to the addition of carbopol 934. However, methylcellulose has been shown to have mucoadhesive properties and therefore further formulations were prepared which contained 1.0 and 1.5% w/w methylcellulose in combination with 1.5% w/w carbopol 934. Visual assessment of these formulations showed that they were homogeneous and had the required consistency for further evaluation. Similarly, HPC was found not to affect the viscosity relative to the addition of carbopol 934. However since HPC has also been implicated as a potential mucoadhesive, formulations containing HPC at 1.0 and 1.5% w/w together with carbopol 934 at 1.5% w/w were found visually acceptable for further rheological assessment. Formulation 4 was also found to be visually acceptable with respect to viscosity and solvation and this included HEC (another potential mucoadhesive polymer). Therefore five formulations (Formulation 4, 14, 15, 16 and 17 were rheologically assessed for their mucoadhesive strength using pig mucin.

Rheological Assessment of Formulations 4, 14, 15, 16 and 17

The elastic modulus G' is a measure of sample resistance to elastic deformation (i.e. a reflection as the polymer network connectivity) and G" is a measure of sample resistance to viscous deformation.

The mean G' and G" at 5 Hz, averaged over 5 samples were extracted from the resultant data to allow comparisons between different formulations. An expression that allows for the determination of synergistic differences, in terms of G' and G"; between the formulation/mucin mixture and the individual components of that mixture is given in Equation 1. The higher, the relative G' values the greater the interaction of the formulation with the mucin.

$$\text{Relative} G' = \frac{G'_{(Formulation/Mucin)} - (G'_{(Formulation)} + G'_{(Mucin)})}{G'_{(Formulation)} + G'_{(Mucin)}} \quad \text{Equation 1}$$

A similar equation can be used to calculate G". Tan δ was calculated using the relative G' and G" values using Equation 2.

$$\tan \delta = \frac{\text{mean Relative} G''}{\text{mean Relative} G'} \quad \text{Equation 2}$$

FIG. 7 shows the relative G' and G" values for all five formulations tested and FIG. 8 shows the corresponding tan δ values.

Based on the rheological assessment, the order for the increase in mucoadhesive strength was found to be Formulation 17>Formulation 16>Formulation 14>Formulation 15>Formulation 4. However, Formulations 14 and 15 displayed large variations (as observed with the large standard deviations). This could be due to the non-homogeneous interactions of these formulations with mucin. Furthermore, the G' generated for the formulations in deionised water were also found to have large variations thus indicating that these formulations displayed non homogeneous hydration. Formulation 4 was found to have the highest G' values when mixed with the mucin, however, the relative G' value was significantly lower ($p<0.05$) compared to all the other formulations tested. This was attributed to the fact that the G' values for Formulation 4 dispersed in water were considerably higher compared to all the formulations dispersed in water. It would appear that Formulation 4 produced a relatively good viscoelastic gel in water (compared to the other formulations in water), however there appeared to be a relatively small interaction with mucin since the relative G' value, which eliminates the effect of the formulation (as well as the mucin effect) was significantly lower. Based on the relative G' values, Formulations 16 and 17 showed the largest interaction with pig mucin inferring that these two formulations could be used as potential mucoadhesive formulations. Formulations 14 and 15 showed some interaction with mucin, however the hydration/interaction of these formulations could be inhomogeneous as judged by the large standard deviations. Formulation 4 showed the lowest relative G' value and therefore the lowest interaction. The corresponding tan δ values are a relative measure of the viscoelasticity, the lower tan δ indicates a relatively higher entanglement and conversely the higher tan δ indicates a relatively low entanglement (due to a relatively larger viscous component) and thus supports these observations.

Optimisation and Preparation of Selected Active and Placebo Formulations

The optimisation procedure was carried out in order to reduce the time of preparation for the formulations from ca. 24 h down to ca. 12 h. Formulations 16 and 17 were chosen for optimisation and stability studies.

HPLC Analysis of I3A Formulations

Table 25 shows the percentage peak purities for I3A 'b' as well as percentage area of isoform 'a' and other unassigned peaks (UAP) for Formulations 16 and 17 taken at time zero. Also shown as a comparator is the percentage peak purity of a 0.1% w/w I3A IPA gel sample at time zero. All peaks for the buccal formulations were manually integrated and compared to the respective placebo formulations.

TABLE 25

Percentage peak purities of formulations at time zero.

| Formulation | % Peak purity I3A 'b' | % isoform 'a' | % Total UAP |
|---|---|---|---|
| 16 | 99.6 | 0.3 | 0.1 |
| 17 | 99.7 | 0.3 | 0.0 |
| 0.1% w/w IPA gel | 99.2 | 0.5 | 0.3 |

Table 26 shows the percentage peak purities for I3A 'b' as well as percentage area of isoform 'a' and other unassigned peaks (UAP) for Formulations 16 and 17 taken at approximately two weeks after storage at 2-8° C. and 40° C. (accelerated stability). Also tabulated as a comparator is the percentage peak purity 0.1% w/w I3A IPA gel stored at 40° C. for one week. All peaks for the buccal formulations were manually integrated compared to the respective placebo formulations.

TABLE 26

Percentage chromatographic peak purities of formulations at time ca. 1-2 weeks stored at 2-8° C. and 40° C.

| Formulation | % Peak purity I3A 'b' | | % isoform 'a' | | % Total UAP | |
|---|---|---|---|---|---|---|
| | 2-8° C. | 40° C. | 2-8° C. | 40° C. | 2-8° C. | 40° C. |
| 16 | 99.8 | 99.2 | 0.2 | 0.4 | 0.0 | 0.4 |
| 17 | 99.8 | 99.3 | 0.2 | 0.4 | 0.0 | 0.3 |
| *0.1% w/w IPA gel | ND | 98.3 | ND | 1.6 | ND | 0.1 |

*Peak purity after one week;
ND—not determined

There appears to be no apparent difference in the percentage peak purity of I3A in any of the formulations, at time zero to the initial value on receipt (99.3% I3A 'b', report PB21001/24). Furthermore, the percentage area of isoform 'a' on receipt was 0.40%, which is similar to the percentage peak area for isoform 'a' at time zero (Table 25).

There was no noticeable increase in the percentage of isoform 'a' after approximately 1-2 week storage of the buccal formulations, at 2-8° C. (Table 26), whereas an increase in the percentage of isoform 'a' was observed for all buccal samples stored at 40° C. However, the increase in the percentage of isoform 'a' observed for the 0.1% w/w IPA gel was higher (1.60%) after 1 week storage at 40° C. Based on the percentage peak purities, this preliminary data would appear to indicate that the I3A buccal formulations are at least as stable as the 0.1% I3A IPA gel and possibly even more stable.

EXAMPLE 6

Poloxamer Formulations
Four poloxamer formulations were investigated.
Materials

| Material | Supplier |
|---|---|
| I3A 'b' Batch No 0319. | Peplin Limited, Australia. |
| Citric acid monohydrate BP Lot no. R11115 | Raught Ltd, UK |
| Trisodium citrate dihydrate BP Lot no. R0092143 | Raught Ltd, UK |
| Deionised water | Millipore, UK |
| Poloxamer 407 (Lutrol F127) Lot no. WPTY562B | BASF, Germany |
| Ethanol (Analar) 99.7-100% w/w Lot no. L354007 | BDH, UK |
| Polyethyleneglycol 400 (PEG 400) Lot no. 53820403 312 | Merck, Germany |
| Propylene glycol Lot no. K32254378 336 | Merck, Germany |
| Acetonitrile (ACN) HPLC Gradient Grade Lot no 0309807 | Fisher Scientific, UK |
| Trifluoroacetic acid (TFA) Lot. no. 0263747 | Fisher Chemicals, UK |
| Benzyl alcohol Ph Eur, BP, NF Batch No. K31593981 301 | Merck KGaA, Germany |

Methods
Choice of Excipients
Prior to preformulation studies, several suitable excipients for poloxamer formulations were identified, and are listed below, together with maximum recommended concentrations.

| Excipients | Concentration |
|---|---|
| Propylene glycol | 75.2% w/v (IM); 60.0% v/v (IV) |
| *PEG 400 | 65.0% w/v (IV); 18% v/v (IM) |
| Benzyl alcohol | 3.0% w/v (IV) |
| Citric acid | 1.0% w/v (IM) |
| Sodium citrate | 2.85% w/v (IM) |

*Used for control formulation

Preparation of Formulations for Rheological Studies
Various placebo poloxamer 407 formulations were prepared using the excipients listed above in order to evaluate the rheological behaviour.
Preparation of Citrate Buffer pH 3
Citric acid monohydrate (Mwt 211 g/mole) was prepared in deionised water at a concentration of 0.1 M. A solution of tri-sodium citrate dihydrate, 0.1 M, (Mwt 294.1 g/mole) was also prepared in deionised water. Citrate buffer solution pH 3 was prepared by mixing 40% v/v citric acid monohydrate solution (0.1 M), 10% v/v trisodium citrate dihydrate solution (0.1 M) and 0% v/v deionised water and the final pH was measured using a pH Meter (3320 JENWAY).
Preparation of Poloxamer 407 'Base' Solutions
Preliminary studies indicated that poloxamer 407 solutions at a concentration range between 1.8-20% w/w were suitable, for providing a range of viscosities with varying cmt values. The poloxamer solutions were prepared using the cold method reported by Schmolka (1972).
Briefly, the required amounts of poloxamer 407 (Table 27) were added either to citrate buffer pH 3 or propylene glycol/citrate buffer pH 3 in 100 ml borosilicate glass Duran bottles. The propylene glycol/citrate buffer pH 3 was previously prepared by weighing the appropriate amount of propylene glycol and citrate buffer pH 3 (Table 27) and shaken for 1-2 mins until visually homogeneous. The Duran bottles containing the ingredients were capped and placed in an ice/water bath for 4 h with frequent shaking every 15 mins, until clear solutions were produced. These solutions were stored at 2-8° C. until required.
Sterilisation Procedure
Since the gels are required for intralesional therapy, sterilisation is important. In order to achieve sterilisation, the prepared gels wee autoclaved using the BP method, where approximately 100 g of each of the gels listed in Table 27 was placed in 100 ml Duran bottles and autoclaved for 15 mins at 121° C. After this procedure, the gels were left to cool at room temperature, and then stored at 2-8° C. until inquired.

TABLE 27

Actual and target amounts of poloxamer 'base' solutions

| Excipients | Polox-01 | | Polox-02 | | Polox-pg-01 | | Polox-pg-02 | |
|---|---|---|---|---|---|---|---|---|
| | Target weight/g | Actual weight/g | Target weight/g | Actual weight/g | Target weight/g | Actual weight/g | Target weight/g | Actual weight/g |
| Poloxamer 407 | 18 | 18.03366 | 20 | 20.0138 | 18 | 18.04115 | 20 | 20.02152 |
| Propylene glycol | | | | | 10 | 10.01009 | 10 | 10.01882 |
| Citrate buffer pH 3 | 82 | 82.1126 | 80 | 80.1427 | 72 | 72.1025 | 70 | 70.0849 |
| Total | 100 | 100.146 | 100 | 100.157 | 100 | 100.154 | 100 | 100.125 |

TABLE 28

Actual and target amounts of placebo formulations for rheological evaluation

| Excipients | Polox-01-placebo | | Polox-02-placebo | | Polox-pg-01-placebo | | Polox-pg-02-placebo | |
|---|---|---|---|---|---|---|---|---|
| | Target weight/g | Actual weight/g | Target weight/g | Actual weight/g | Target weight/g | Actual weight/g | Target weight/g | Actual weight/g |
| Polox-01 | 9.90 | 9.90671 | | | | | | |
| Polox-02 | | | 9.90 | 9.90458 | | | | |
| Polox-pg-01 | | | | | 9.90 | 9.90885 | | |
| Polox-pg-02 | | | | | | | 9.90 | 9.90033 |
| Benzyl alcohol/ Citrate buffer | 0.10 | 0.10173 | 0.10 | 0.10115 | 0.10 | 0.10027 | 0.10 | 0.10161 |
| Total | 10.0 | 10.00844 | 10.0 | 10.00573 | 10.0 | 10.00912 | 10.0 | 10.00194 |

Preparation of Placebo Poloxamer Formulations for Rheological Evaluation

Due to the instability of I3A to heat sterilisation, formulations containing I3A should be prepared by dissolving the I3A in an appropriate solvent followed by aseptic addition (i.e. aseptic filtration) to autoclaved 'base' poloxamer solutions. The solvent of choice was benzyl alcohol. However, for rheological assessment only placebo poloxamer formulations were prepared containing benzyl alcohol due to the limited availability of I3A.

Preparation of Benzyl Alcohol/Citrate Buffer pH 3 Solution

The amount of citrate buffer added to benzyl alcohol was 2.5% w/w, which was below the solubility of citrate buffer pH 3 in benzyl alcohol. Briefly, approximately 0.5 g of citrate buffer pH 3 was added to 19.5 g of benzyl alcohol to give a final percentage of citrate buffer of 2.5% w/w in benzyl alcohol. This solution was then filtered through a Millipore filter (0.22 μm MILLEX-GV, MILLIPORE) to mimic the condition of aseptic filtration.

Addition of Benzyl Alcohol/Citrate Buffer pH 3 Solution to Poloxamer 'Base' Solutions Placebo formulations (Table 28) were prepared by adding the required amount of filtered benzyl alcohol/citrate buffer pH 3 to the sterilised poloxamer 'base' solutions prepared above. Briefly, approximately 9.90 g (exact weight noted in Table 28) of each poloxamer 'base' solution was weighed into a 20 ml soda glass vial and this was cooled in ice/water to form a liquid (at room temperature these solutions form gels). To the cooled poloxamer 'base' approximately 0.10 g (exact weight shown in Table 28) of filtered benzyl alcohol/ citrate buffer pH 3 was added and vortexed for 2 mins until a visually clear, homogeneous solution was obtained. These formulations were then stored at 2-8° C. until required.

Rheological Evaluation

The rheological evaluation was carried out using a Carrimed $CSL^2$ rheometer. Approximately 0.4 g of the test sample was placed between the platform and parallel plate geometry. Once the sample was compressed between the platform and plate any excess sample was carefully removed using a spatula at right angles to the geometry. Each sample was tested a total of three times and the resultant viscosities were recorded as a function of temperature.

Preparation of Active Formulations and Relative Placebos for Stability and Release Studies Following on from the rheological assessment, active (I3A) and placebo poloxamer formulations were prepared for stability and release studies. Furthermore, placebo and active (0.1% w/w I3A) PEG 400 formulations were also prepared as control formulations for release testing.

Preparation of Stock I3A in Benzyl Alcohol/Citrate Buffer

Approximately 50 mg (target amount) of I3A was accurately weighed into a 7 ml glass bijou vial together with 500 mg (target amount) of benzyl alcohol/citrate buffer pH 3. This mixture was periodically vortexed for 5 mins until the I3A had dissolved.

Preparation of Active and Placebo Poloxamer Formulations

Placebo formulations were prepared as described above (Table 28). Active (I3A) poloxamer formulations containing a target concentration of 0.1% w/w I3A 'b' were prepared in a similar manner to the placebo formulations except that the extra weight due to the addition of I3A 'b' was compensated by a similar reduction in the amount poloxamer 'base' solution added (Table 29). Briefly, approximately 110 mg (exact weight noted) of I3A/benzyl alcohol/citrate buffer pH 3 was added to 9.89 g of the cooled, sterilised poloxamer 'base' solution and vortexed for ca. 2 mins until a visibly clear, homogeneous solution was obtained. The exact weights and target weights are shown in Table 29.

TABLE 29

Actual and target amounts of active poloxamer formulations for stability and release studies

| Excipients | Polox-01-active Target weight/g | Polox-01-active Actual weight/g | Polox-02-active Target weight/g | Polox-02-active Actual weight/g | Polox-pg-01-active Target weight/g | Polox-pg-01-active Actual weight/g | Polox-pg-02-active Target weight/g | Polox-pg-02-active Actual weight/g |
|---|---|---|---|---|---|---|---|---|
| Polox-01 | 9.89 | 9.89261 | | | | | | |
| Polox-02 | | | 9.89 | 9.89098 | | | | |
| Polox-pg-01 | | | | | 9.89 | 9.89461 | | |
| Polox-pg-02 | | | | | | | 9.89 | 9.89704 |
| *I3A/Benzyl alcohol/Citrate buffer | 0.11 | 0.11051 | 0.11 | 0.10999 | 0.11 | 0.11496 | 0.11 | 0.11338 |
| Total | 10.0 | 10.00312 | 10.0 | 10.00097 | 10.0 | 10.00957 | 10.0 | 10.01042 |

*Exact I3A in benzyl alcohol/citrate buffer pH 3 = 0.09118 g/g

TABLE 30

Actual and target amounts of placebo and active PEG400 control formulations for release studies

| Excipients | PEG 400-placebo Target weight/g | PEG 400-placebo Actual weight/g | PEG 400-active Target weight/g | PEG 400-active Actual weight/g |
|---|---|---|---|---|
| PEG400 | 7.92 | 7.92151 | 7.912 | 7.91457 |
| Citrate buffer pH 3 | 1.98 | 1.97021 | 1.978 | 1.99458 |
| Benzyl alcohol | 0.10 | 0.10592 | | |
| *I3A/Benzyl alcohol | | | 0.11 | 0.11274 |
| Total | 10.0 | 10.02189 | 10 | 10.02189 |

Exact I3A in benzyl alcohol = 0.09155 g/g

Preparation of PEG400 Control Formulations

Following a similar procedure, 12.5 mg of I3A was added to 125 mg benzyl alcohol, which had been previously filtered through a Millipore filter (0.22 μm MILLEX-GV, MILLIPORE). This solution was vortexed for approximately 5 mins until the I3A bad completely dissolved. To prepare the active control formulations approximately 110 mg of this mixture was added to a solution of 7.912 g PEG400 and 1.978 g of citrate buffer pH 3. The placebos were prepared in a similar manner except that approximately 7.92 g of PEG400 and 1.98 g of citrate buffer and 100 mg of sterilised benzyl alcohol were used. Exact weights and target weights are shown in Table 6 for placebo and active PEG 400 formulations, respectively.

Storage Conditions for Active and Placebo Poloxamer Formulations

Aliquots of each of poloxamer 407 formulation (placebo or active) were dispensed into 2 ml screw cap amber glass vials (borosilicate glass), sealed and stored at three storage conditions namely 2-8° C. 25±2° C. and 40±2° C. for stability studies.

Stability Testing of I3A in the Poloxamer Formulations

For the purpose of drug product evaluation an extraction method was set up to evaluate the degradation of I3A 'b' to isoform 'a' (chromatographic peak purity). The extraction of I3A from the active formulation was as follows (the same procedure was also used for the placebo formulation). Briefly, about 0.5 g of the formulation was accurately weighed into a 5 ml volumetric flask and made up to the mark with HPLC grade acetonitrile/citrate buffer pH 3 (90:10 v/v). The solution was aliquoted into HPLC vials and analysed.

Preliminary recovery data (not shown) indicated that ca. 80% or more of I3A 'b' was recovered from the active formulation and more significantly, there was no interference from any of the excipients in the formulation. Formulations were analysed at t=0 and accelerated stability studies (40° C.) were conducted at t=5 weeks.

Preliminary I3A Release Studies

The release of I3A 'b' from the formulations across synthetic membrane was investigated using Franz diffusion cells under occluded conditions.

Choice of Receiver Fluid

The receiver fluid employed to try and maintain sink conditions was 20% v/v ethanol/citrate buffer (pH 3.0) and this was incorporated into the Franz cell and stirred constantly with a magnetic stirrer. Preliminary stability studies were conducted on I3A in 20% v/v ethanol/citrate buffer (pH 3.0) at 37° C. over ca. 18 h. The percentage peak area increase in isoform 'a' after 18 h was found to be 0.26%. For the purpose of the Franz cell study this was considered acceptable. The kinetic solubility of I3A in 20% v/v ethanol/citrate buffer (pH 3.0) was determined to be 509.7±3 μg/ml at 25° C.

In Vitro Release Studies (Franz Cell)

Individually calibrated Franz diffusion cells with an average diffusional surface area of 0.53 cm² and an average receptor volume of 1.85±0.02 ml were used to conduct the release study. The regenerated cellulose membranes (MWCO 12000-14000) were prepared, cut and mounted onto the Franz tells. The membranes were allowed to equilibrate with the receiver phase for 30 mins before applying the formulations. An infinite dose of 0.5 g of each formulation was applied on the membrane surface using a positive displacement Finnpipette®. One sample reading was investigated (26 h after gel application) whereby 200 μl of the receiver fluid was carefully withdrawn from the arm of the Franz cell. Throughout the experiment, any losses in receiver fluid due to evaporation from the Franz cells were replaced to maintain a constant volume. The experiment was performed under occluded conditions (the top of the upper donor wells covered with Parafilm®), for all formulations (n=3 Franz cells per active formulation and n=1 Franz cell per placebo formulation). Samples were analysed via HPLC, as described in Example 1, and the concentration of I3A 'b' released evaluated using a series of calibration standards prepared in 80% v/v citrate buffer/20% v/v ethanol.

Results

Sterilisation of Poloxamer 'Base' Solutions

Immediately after sterilisation of the poloxamer 'base' solutions, Polox-01 and Polox-02—without propylene showed phase separation. Once cooled in ice/water these solutions became clear, homogeneous phases. However, the 'base' solutions containing propylene glycol, Polox-pg-01 and Polox-pg-02 showed no phase separation immediately after sterilisation, suggesting that the addition of propylene glycol inhibits this phenomenon.

Rheological Assessment

Rheological studies were carried out on poloxamer placebo formulations and the viscosity (Pa·s) was determined as a function of temperature (° C.), over the temperature range 4-40° C. The cmt value was determined by taking the mid-point of the inflexion. For all placebo formulations there was a small increase in viscosity with increase in temperature until at a certain point, at the cmt, there was a dramatic increase in viscosity with a small increase in temperature. The cmt value was found to be concentration dependent, i.e. the lower the poloxamer 407 concentration, the higher the cmt value. Furthermore, the addition of propylene glycol to the poloxamer placebo formulations further reduced the cmt. However, above the cmt, the viscosities for the same samples increased approximately 1.5-2 fold compared to the respective propylene glycol free formulations. For example, at 37° C. the viscosity of Polox-01-placebo was found to be ca. 1.2 Pa·s whereas the respective propylene glycol placebo formulation (Polox-pg-01-placebo) was found to be 2.4 Pa·s. Therefore, the addition of propylene glycol would appear to increase the viscosity above the cmt value, however the actual cmt value is reduced. Table 31 summarises the cmt values and the viscosities at 37° C. for all formulations.

TABLE 31

Cmt values and viscosities (at 37° C.) for all poloxamer placebo formulations (n = 3 ± SEM)

|  | Polox-01-placebo | Polox-02-placebo | Polox-pg-01-placebo | Polox-pg-02-placebo |
|---|---|---|---|---|
| Cmt/° C. | 28.5 ± 0.07 | 21.9 ± 0.03 | 22.7 ± 0.00 | 18.2 ± 0.03 |
| Viscosity (Pa · s) at 37° C. | 1.2 ± 0.08 | 2.9 ± 0.06 | 2.4 ± 0.01 | 3.4 ± 0.04 |

Stability Studies of I3A in Poloxamer Formulations

Table 32 shows the percentage peak purities for I3A 'b' as well as the percentage area of isoform 'a' and other unassigned peaks (UAP) for all active poloxamer formulations taken at time zero. Also shown as a comparator is the percentage peak purity of a 0.1% w/w I3A IPA gel at time zero. All peaks were manually integrated and compared to the respective placebo formulations.

TABLE 32

Percentage peak purities of formulations at time zero.

| Formulation | % Peak purity I3A 'b' | % isoform 'a' | % Total UAP |
|---|---|---|---|
| Polox-01-active | 99.8 | 0.2 | 0.0 |
| Polox-02-active | 99.8 | 0.2 | 0.0 |
| Polox-pg-01-active | 99.8 | 0.2 | 0.0 |
| Polox-pg-02-active | 99.8 | 0.2 | 0.0 |
| 0.1% w/w IPA gel | 99.2 | 0.5 | 0.3 |

Table 33 shows the percentage peak parities for I3A 'b' as well as percentage area of isoform 'a' and other UAP's for all active formulations taken at five week after storage at 40° C. (accelerated stability). Also tabulated as a comparator is the percentage peak purity of 0.1% w/w I3A IPA gel stored at 40° C. for four weeks. All peaks were manually integrated compared to the respective placebo formulation.

TABLE 33

Percentage chromatographic peak purities of formulations at time five weeks, stored at 40° C.

| Formulation | % Peak purity I3A 'b' | % isoform 'a' | % Total UAP |
|---|---|---|---|
| Polox-01-active | 95.6 | 2.6 | 1.8 |
| Polox-02-active | 93.3 | 2.8 | 3.9 |
| Polox-pg-01-active | 92.2 | 2.7 | 5.1 |
| Polox-pg-02-active | 93.3 | 3.0 | 3.7 |
| *0.1% w/w IPA gel | 94.8 | 4.7 | 0.5 |

*Tested after four weeks storage at 40° C. using HPLC method 1

There is no apparent difference in the percentage peak purity of I3A in any of poloxamer formulations. At time zero, however, the percentage of isoform 'a' is lower for these formulations compared to the I3A IPA gel, possibly as a result of the addition of a small amount of citrate buffer pH 3 added to benzyl alcohol during the manufacture of the formulations.

An increase in the percentage of isoform 'a' was observed for all active poloxamer formulations after five weeks storage at 40° C. However, the increase in percentage of isoform 'a' observed for the 0.1% w/w IPA gel was higher (4.7%) after four week storage at 40° C. Based on the percentage peak purities, these data would appear to indicate that the stability of the I3A poloxamer formulations are comparable to the 0.1% I3A IPA gel.

Preliminary Release Studies

FIG. 9 shows the amount released ($\mu g/cm^2$) after 26 h, of I3A from 0.1% w/w poloxamer gel and PEG 400 formulations. No significant difference in release was found ($p>0.05$) between any of the poloxamer formulations, however, the release from all the poloxamer formulations was significantly slower ($p<0.05$) than the release from the PEG400 control formulation. The amount of I3A 'b' released averaged for all poloxamer formulations was ca. 16 $\mu g/cm^2$ whereas the amount released from the control PEG 400 formulation was ca. 53 $\mu g/cm^2$; this represents a reduction of ca. 70% in the amount of I3A 'b' released from all the poloxamer formulations compared to the control after 26 h.

Results

Four poloxamer formulations were investigated in this study. These poloxamer gels gave an increase in viscosity (at 37° C.) where the viscosity of polox-01-placebo<polox-pg-01-placebo<polox-02-placebo<polox-pg-02-placebo. Furthermore, the addition of propylene glycol would appear to increase the viscosity above the cmt value, however the actual cmt value is reduced.

The stability of the poloxamer gels appears to be comparable to the 0.1% I3A IPA gel under accelerated conditions.

Release studies showed that there was no significant difference in release (p>0.05) between any of the poloxamer formulations; however, the release from all the poloxamer formulations was significantly slower (p<0.05) than the release from the PEG 400 control formulation. Furthermore, a reduction of ca. 70% in the amount of I3A 'b' released from all the poloxamer formulations was observed compared to the control, after 26 h.

EXAMPLE 7

The in vitro release of I3A 'b' from oily-based intralesional formulations compared to the PEG 400 control formulation was investigated.

Materials

| Material | Supplier |
|---|---|
| I3A 'b' Batch No 0319. | Peplin Limited, Australia. |
| Citric acid monohydrate BP Lot no. R11115 | Raught Ltd, UK |
| Trisodium citrate dihydrate BP Lot no. R0092143 | |
| Deionised water | Millipore, UK |
| Crodamol GTC/C (Medium chain triglycerides) Batch No. GE03907/3270 | Croda, Singapore |
| Ethanol (Analar) 99.7-100% w/w Lot no. L354007 | BDH, UK |
| Polyethyleneglycol 400 (PEG 400) Lot no. 53820403 312 | Merck, Germany |
| Benzyl alcohol Ph Eur, BP, NF Batch No. K31593981 301 | |
| Acetonitrile (ACN) HPLC Gradient Grade Lot no 0309807 | Fisher Scientific, UK |
| Trifluoroacetic acid (TFA) Lot. no. 0263747 | |
| Butylated Hydroxy Toluene (BHT) Lot no. CHASMP115 | Jan Dekker International, Netherlands |

Methods

Preparation of I3A (Active) and Placebo Formulations for Release Studies

Three oil formulations were prepared with there respective placebos. The amount of benzyl alcohol was kept to 1% w/w. The preparation of two formulations involved either the addition of an antioxidant prior to heat sterilisation of the oil or addition of antioxidant after sterilisation of the oil.

Preparation of Oil Formulation (as Reported in PB23001/2) 'Croda-BA'

Sterilisation of Fractionated Coconut Oil

Approximately 100 g of the fractionated coconut oil (CRODAMOL GTC/C) was weighted into a 100 ml conical flask (borosilicate glass), stoppered (borosilicate glass stopper) and placed inside a pre-heated oven (Gallenkampf Hot box Oven with fan, Size 2) at 170±2° C. for 1 h. After this procedure, the oil was allowed to cool to room temperature before use.

Addition of I3A to the Sterilised Oil

Approximately 15 mg, of I3A was accurately weighed into a 20 ml glass vial and added to approximately 150 mg of benzyl alcohol (exact weight noted), which had previously been filtered through a 0.22 μm MILLEX-GV filter. This mixture was periodically vortexed for approximately 2 h until the I3A had dissolved in the benzyl alcohol. To this mixture approximately 14.835 g or the sterilised oil was added and vortexed for approximately 5 mins until a homogeneous solution was obtained. The placebo was prepared in a similar manner except that approximately 14.85 g of the sterilised oil (exact weight noted) was used to compensate for I3A. Exact weights and percentage compositions are shown in Table 34 and 35 for active (I3A) and placebo formulations.

TABLE 34

Target and actual amounts (and % w/w) for the I3A Croda/BA oil formulation

|  | Target weight | Target % w/w | Actual weight | *Actual % w/w |
|---|---|---|---|---|
| I3A (0319) | 15 mg | 0.10 | 15.56 mg | 0.104 |
| Benzyl alcohol | 150 mg | 1.0 | 159.98 mg | 1.065 |
| Fractionated coconut oil | 14.835 g | 98.9 | 14.84625 | 98.831 |
| Total | 15 g | 100 | 15.02179 g | 100 |

*Rounded up to 3 d.p.

TABLE 35

Target and actual amounts (and % w/w) for the placebo Croda/BA oil formulation

|  | Target weight | Target % w/w | Actual weight | *Actual % w/w |
|---|---|---|---|---|
| Benzyl alcohol | 150 mg | 1.0 | 149.84 mg | 0.999 |
| Fractionated coconut oil | 14.85 g | 99.0 | 14.85161 g | 99.001 |
| Total | 15 g | 100 | 15.00145 g | 100 |

*Rounded up to 3 d.p.

Preparation of Oil Formulation 'Croda-BA/Antiox'

Long term storage of oils may lead to rancidity, which may degrade the drug product. Therefore, an antioxidant may be included in the formulation (after heat sterilisation) in order to reduce this effect. Placebo and active formulations containing an antioxidant after heat sterilisation of the oil were prepared according to the following methodology.

Preparation of Antioxidant/Benzyl Alcohol Mixture

Approximately 60 mg of antioxidant (BHT) was dissolved in 2 g of benzyl alcohol and filtered through a 0.22 μm MILLEX-GV filter.

Addition of I3A to the Sterilised Oil

Approximately 15 mg of I3A (Batch 0319) was accurately weighed into a 20 ml glass vial and added to approximately 154.5 mg of BHT/benzyl alcohol prepared as above. This mixture was periodically vortexed for approximately 2 h until the I3A had dissolved in the benzyl alcohol. To this mixture approximately 14.8305 g of the cooled sterilised oil was added and vortexed for approximately 5 mins until a homogeneous solution was obtained. The placebo was prepared in a similar manner except that approximately 14.8455 g of the sterilised oil (exact weight noted) was used to compensate for I3A. Exact weights and percentage compositions are shown in Table 36 and 37 for active (I3A) and placebo formulations.

TABLE 36

Target and actual amounts (and % w/w) for the I3A Croda-BA/Antiox oil formulation

|  | Target weight | Target % w/w | Actual weight | *Actual % w/w |
|---|---|---|---|---|
| I3A (0319) | 15 mg | 0.10 | 15.14 mg | 0.101 |
| Benzyl alcohol | 150 mg | 1.0 | 158.27 mg | 1.055 |
| BHT | 4.5 mg | 0.03 | 4.55 mg | 0.030 |
| Fractionated coconut oil | 14.8305 g | 98.87 | 14.83014 g | 98.814 |
| Total | 15 g | 100 | 15.0081 g | 100 |

*Rounded up to 3 d.p.

TABLE 37

Target and actual amounts (and % w/w) for the placebo Croda-BA/Antiox oil formulation

|  | Target weight | Target % w/w | Actual weight | *Actual % w/w |
|---|---|---|---|---|
| Benzyl alcohol | 150 mg | 1.0 | 150.56 mg | 1.004 |
| BHT | 4.5 mg | 0.03 | 4.55 mg | 0.030 |
| Fractionated coconut oil | 14.8455 g | 98.97 | 14.84591 g | 98.966 |
| Total | 15 g | 100 | 15.00102 g | 100 |

*Rounded up to 3 d.p.

Preparation of Oil Formulation 'Croda/Antiox-BA'

Dry heat sterilisation of oils may also lead to rancidity, which may degrade the drug product. Therefore, an antioxidant may be included in the formulation in order to reduce this effect prior to heat sterilisation. Placebo and active formulations containing an antioxidant prior heat sterilisation of the oil were prepared according to the following methodology.

Sterilisation of Antioxidant/Oil Mixture

Approximately 15 mg of antioxidant (BHT) was dissolved in approximately 50 g of oil in a 100 ml conical flask (borosilicate glass), stoppered (borosilicate glass stopper) and placed inside a pre-heated oven (Gallenkampf Hot box Oven with fan, Size 2) at 170±2° C. for 1 h. After this procedure, the antioxidant/oil was allowed to cool to room temperature before use.

Addition of I3A to the Sterilised Oil

Approximately 15 mg of I3A (Batch 0319) was accurately weighed into a 20 ml glass vial and added to approximately 150 mg of benzyl alcohol, which had previously been filtered through a 0.22 µm MILLEX-GV filter. This mixture was periodically vortexed for approximately 2 h until the I3A had dissolved in the benzyl alcohol. To this mixture approximately 14.835 g of the cooled sterilised antioxidant/oil mixture was added and vortexed for approximately 5 mins until a homogeneous solution was obtained. The placebo was prepared in a similar manner except that approximately 14.8455 g of the sterilised oil (exact weight noted) was used to compensate for I3A. Exact weights and percentage compositions are shown in Tables 38 and 39 for active (BA) and placebo formulations.

TABLE 38

Target and actual amounts (and % w/w) for the I3A Croda/Antiox-BA oil formulation

|  | Target weight | Target % w/w | Actual weight | *Actual % w/w |
|---|---|---|---|---|
| I3A (0319) | 15 mg | 0.10 | 15.09 mg | 0.100 |
| Benzyl alcohol | 150 mg | 1.0 | 146.92 mg | 0.979 |
| BHT | 4.5 mg | 0.03 | 4.42 mg | 0.030 |
| Fractionated coconut oil | 14.8305 g | 98.87 | 14.83568 g | 98.891 |
| Total | 15 g | 100 | 15.00211 g | 100 |

*Rounded up to 3 d.p.

TABLE 39

Target and actual amounts (and % w/w) for the placebo Croda/Antiox-BA oil formulation

|  | Target weight | Target % w/w | Actual weight | *Actual % w/w |
|---|---|---|---|---|
| Benzyl alcohol | 150 mg | 1.0 | 153.9 mg | 1.025 |
| BHT | 4.5 mg | 0.03 | 4.67 mg | 0.031 |
| Fractionated coconut oil | 14.8455 g | 98.97 | 14.85901 g | 98.944 |
| Total | 15 g | 100 | 15.01758 g | 100 |

*Rounded up to 3 d.p.

Aliquots of all the formulations were stored for preliminary release studies and the remainder were aliquoted into 2 ml amber borosilicate glass vials, capped and stored at 2-8° C. and 25° C. for stability studies.

Preliminary I3A Release Studies

The release of I3A 'b' from the formulations across synthetic membrane was investigated using Franz diffusion cells under occluded conditions.

Choice of Receiver Fluid

The receiver fluid employed to try and maintain sink conditions was 20% v/v ethanol/citrate buffer (pH 3.0) and this was incorporated into the Franz cell and stirred constantly with a magnetic stirrer. Preliminary stability studies were conducted on I3A in 20% v/v ethanol/citrate buffer (pH 3.0) at 37° C. over ca. 18 h. The percentage peak area increase in isoform 'a' after 18 h was found to be 0.26%. For the purpose of the Franz cell study this was considered acceptable. The kinetic solubility of I3A in 20% v/v ethanol/citrate buffer (pH 3.0) was determined to be 509.7±3 µg/ml at 25° C.

In Vitro Release Studies (Franz Cell)

Individually calibrated Franz diffusion cells with an average diffusional surface area of 0.53 cm$^2$ and an average receptor volume of 1.85±0.02 ml were used to conduct the release study. The regenerated cellulose membranes (MWCO 12000-14000) were prepared, cut and mounted onto the Franz cells. The membranes were allowed to equilibrate with the receiver phase for 30 mins before applying the formulations. An infinite dose of 0.5 g of each formulation was applied onto the membrane surface using a positive displacement Finnpipette®. One sample reading was investigated (26 h after gel application) whereby 200 µl of the receiver fluid was carefully withdrawn from the arm of the Franz cell. Throughout the experiment, any losses in receiver fluid due to evaporation from the Franz cells were replaced to maintain a constant volume. The experiment was performed under occluded conditions (the top of the upper donor wells covered with Parafilm®), for all formulations (n=3 Franz cells per active formulation and n=1 Franz cell per placebo formulation). Samples were analysed via HPLC and the concentration of I3A 'b' released evaluated using a series of calibration standards prepared in 80% v/v citrate buffer/20% v/v ethanol.

HPLC Method

The HPLC method previously described in Example 1 was used for the determination of I3A.

Results

Preliminary Release Studies

FIG. 10 shows the amount of I3A 'b' released ($\mu g/cm^2$) after 26 h, from 0.1% w/w oil and PEG 400 formulations. No significant difference in release was found (p>0.05) between any of the oil formulations. However, the release of I3A 'b' from all the oil formulations was significantly less (p<0.05) than the release from the PEG 400 control formulation. The amount of I3A 'b' released from all oil formulations was ca. 3.4 $\mu g/cm^2$ however, the amount released from the control PEG 400 formulation was ca. 16 fold greater (53 $\mu g/cm^2$). Furthermore, it would appear that the addition of BHT (antioxidant) did not significantly affect the release of I3A 'b' from the oil formulations.

EXAMPLE 8

Stability of IPA Gel Formulations

The stability (T=12 months) of I3A 'b' in IPA gel formulations prepared using different pH citrate buffers was determined. The pH range was from 2.5 to 4.0.

Materials

| Materials | Supplier |
|---|---|
| Acetonitrile (HPLC grade) Batch no. 0444972 | Fisher Chemicals, UK |
| Citric Acid Monohydrate (USP grade) Batch no. K9129642 | Merck, Germany |
| Deionised water (MilliQ) | Millipore, UK |
| I3Ab (ingenol angelate) Batch no. PEP 0401 | Supplied by Peplin Limited, Australia |
| Tri-Sodium Citrate Dihydrate (USP grade) Batch no. K9125363 | Merck, Germany |
| Trifluoroacetic Acid (HPLC grade) Batch no. 0434753 | Fisher Scientific, UK |

Methods

HPLC Instrumentation and Methodology

Sample solutions were analysed for percentage peak purity by HPLC. The chromatographic conditions for the HPLC Method 2 are detailed below:

Instrumentation:

Waters Alliance 2695 Separations Module plus Autosampler (SN: L96SM4656N)

Waters 996 PDA detector (SN: MX7AM7987M)

Millennium[32] Software, Version 4.00

Chromatographic Conditions:

Column: Symmetry $C_{18}$-5 µm (Waters)
(SN: T70641T 1.2)

Column length: 150×3.90 mm

Column temperature: 30° C.±2° C.

Guard column: Symmetry $C_{18}$-5 µm (Waters)
(PN: WAT054225)

Guard column length: 20×3.90 mm

Mobile phase: 0.02% v/v TFA in Water (A); 0.02% v/v TFA in Acetonitrile (B) A:B, 50:50 (starting composition)

Flow rate: 1.0 ml/min

Autosampler temperature: 8° C.±2° C.

UV wavelength: 230 nm

Injection volume: 10 µl

Run time: 20 mins

Gradients

| Step | Time | Flow | % A | % B | Curve |
|---|---|---|---|---|---|
| 1 | | 1.00 | 50.0 | 50.0 | |
| 2 | 2.00 | 1.00 | 50.0 | 50.0 | 6 |
| 3 | 5.00 | 1.00 | 40.0 | 60.0 | 6 |
| 4 | 12.00 | 1.00 | 20.0 | 80.0 | 6 |
| 5 | 16.00 | 1.00 | 20.0 | 80.0 | 6 |
| 6 | 16.50 | 1.00 | 50.0 | 50.0 | 6 |
| 7 | 20.00 | 1.00 | 50.0 | 50.0 | 6 |

Extraction of I3Ab from the IPA Gel Formulations

I3Ab was extracted from each of the IPA gel formulations as follows; approximately 0.5 g of each active or placebo gel formulation was accurately weighed into an A-grade 5 ml volumetric flask. This was performed in triplicate for each formulation. Citrate buffer (pH=3.0, 0.5 ml) was then added to each gel sample and vortex mixed at maximum speed for 1 min and then transferred to an orbital shaker and shaken at 400 rpm for 30 mins. HPLC grade acetonitrile was added, up to volume, to each of the volumetric flasks and vortex mixed again at maximum speed for 1 min. Finally, the volumetric flasks were transferred to an orbital shaker and shaken at 400 rpm for 60 mins. Aliquots were then transferred to HPLC vials for analysis.

Measurement of Apparent pH of Placebo Gels

The apparent pH of the placebo gels was measured using a Jenway 3320 pH meter with a combination pH electrode. Briefly approximately 0.5 g of each gel was transferred to 25 ml glass vials and allowed to stand at room temperature for at least 1 h. The combination pH electrode was placed into the IPA gel ensuring all of the membrane of the electrode was covered with gel. The reading on the pH meter was allowed to settle for a minimum of 1 min and the apparent pH of the gel recorded.

Results

Measurement of the Apparent pH of Placebo Gels at T=12 mths

The apparent pH of the placebo IPA gels at T=0 and T=12 months after storage at 2-8° C. is shown in Table 40.

TABLE 40

Apparent pH of the placebo IPA gels at T = 0 and T = 12 months

| pH Citrate Buffer (±0.05) | Apparent pH of Placebo Gel T = 0 (n = 1) | Apparent pH of Placebo Gel T = 12 months (n = 1) |
|---|---|---|
| 2.50 | 3.07 | 2.97 |
| 2.75 | 3.34 | 3.19 |
| 3.00 | 3.62 | 3.57 |
| 3.50 | 4.22 | 4.23 |
| 4.00 | 4.74 | 4.75 |

The data in Table 40 show that there was no significant change in apparent pH, after 12 months storage at 2-8° C., for the placebo IPA gels prepared with pH 3.00, 3.50 and 4.00 citrate buffers. However, for the placebo IPA gels prepared with pH 2.50 and 2.75 citrate buffers there was a slight reduction in pH observed after 12 months storage at 2-8° C. The reduction in pH observed for these gels may be attributable to the evaporation of IPA from the gel either during storage or during sample analysis.

Percentage Peak Purity of I3A Isomers in Active IPA Gels at T=12 Months

Table 41 shows the percentage peak purity of I3A isomers for the different active (0.1% w/w) IPA gel formulations after storage for 12 months at 2-8° C. and Table 42 shows the comparison of percentage peak purity of I3Aa at T=0 and T=12 months.

TABLE 41

Percentage peak purity of I3A isomers for the active IPA gels after 12 months storage at 2-8° C.

| pH of Citrate Buffer (±0.05) | Apparent pH of Placebo Gel (T = 12 months) | Percentage peak purity of isoform a | Percentage peak purity of I3Ab | Percentage peak purity of other UAPs |
|---|---|---|---|---|
| | | Percentage Peak Purity (mean ± SD, n = 3) | | |
| 2.50 | 2.97 | 0.64 ± 0.22 | 99.12 ± 0.40 | 0.24 ± 0.20 |
| 2.75 | 3.19 | 1.07 ± 0.16 | 98.32 ± 0.61 | 0.31 ± 0.17 |
| 3.00 | 3.57 | 1.26 ± 0.24 | 98.66 ± 0.31 | 0.08 ± 0.12 |
| 3.50 | 4.23 | 2.09 ± 0.17 | 97.74 ± 0.27 | 0.17 ± 0.11 |
| 4.00 | 4.75 | 4.92 ± 0.05 | 94.84 ± 0.07 | 0.24 ± 0.04 |

Data Analysed Using HPLC Method 2

The data in Table 41 show that, after 12 months storage at 2-8° C., there is a increase in percentage peak purity of isoform a with increasing apparent pH of the respective placebo gel formulation. For example, an IPA gel produced with pH 2.75 citrate buffer has a percentage peak purity of isoform a of 1.07% compared to an IPA gel formulation prepared with pH 4.00 citrate buffer which has a percentage peak purity of isoform a of 4.92%. These data highlight the increased stability of I3A b in IPA gel formulations prepared with lower pH citrate buffers.

TABLE 42

Comparison of percentage peak purity of I3Aa at T = 0 and T = 12 months

| pH of Citrate Buffer (±0.05) | Apparent pH of Placebo Gel (T = 12 months) | Percentage peak purity of isoform a T = 0 | Percentage peak purity of I3Aa T = 12 months |
|---|---|---|---|
| | | Percentage Peak Purity (mean ± SD, n = 3) | |
| 2.50 | 2.97 | 0.44 ± 0.03 | 0.64 ± 0.22 |
| 2.75 | 3.19 | 0.24 ± 0.06 | 1.07 ± 0.16 |
| 3.00 | 3.57 | 0.52 ± 0.01 | 1.26 ± 0.24 |
| 3.50 | 4.23 | 0.47 ± 0.02 | 2.09 ± 0.17 |
| 4.00 | 4.75 | 0.44 ± 0.03 | 4.92 ± 0.05 |

T = 0 data analysed by HPLC Method 1 and T = 12 months data analysed by HPLC Method 2

The data in Table 42 show that there is an increase in percentage peak purity of isoform a in all of the active IPA an formulations after 12 months storage at 2-8° C. However, the IPA gel formulation prepared with pH 2.50 citrate buffer showed only a slight increase in percentage peak purity of isoform a (0.22%) compared to, for example, the IPA gel formulation prepared with pH 4.00 citrate buffer which showed the largest increase in percentage peak purity of isoform a (4.48%). Again, these results highlight the increased stability of I3A b in IPA gel formulations prepared with lower pH citrate buffers. As such, the IPA gel formulation prepared with the lowest pH citrate buffer appears to remain within specification (<1% isoform a) for 12 months at 2-8° C.

Thus, after 12 months storage at 2-8° C., the IPA gel formulations that provided the better stability for I3Ab were those that were prepared with lower pH citrate buffers (pH=2.5-3.0).

EXAMPLE 9

Stability of I3A 'b' in Gel Solutions of Varying pH and Temperature

Methods

Preparation of Gel Premix Solutions

The gel premix solutions were prepared according to the following procedure:
1. Weigh the citrate buffer directly into a clean dry Duran bottle.
2. Weigh the IPA directly into the Duran bottle from Step 1.
3. Weigh the correct amount of I3A 'b' into a clean dry sample bottle.
4. Weigh the correct amount of benzyl alcohol into the sample bottle from Step 3.
5. Place the sample bottle from Step 4 on an orbital shaker and shake at 400 rpm until all of the I3A 'b' has dissolved.
6. Add the I3A 'b'/benzyl alcohol solution from Step 5 to the Duran bottle from Step 2.
7. Still the mixture until a homogeneous solution is obtained.

The compositions of the gel premix solutions to be prepared and placed on stability are:

TABLE 43

Gel premix solution 1

| Component | Concentration w/w | Amount to be Weighed (g) |
|---|---|---|
| Citrate Buffer pH 2.75 | 69.0 | 13.80 |
| Isopropyl Alcohol | 30.0 | 6.00 |
| Benzyl Alcohol | 0.9 | 0.18 |
| I3A 'b' | 0.1 | 0.02 |

TABLE 44

Gel premix solution 2

| Component | Concentration w/w | Amount to be Weighed (g) |
|---|---|---|
| Citrate Buffer pH 3.00 | 69.0 | 13.80 |
| Isopropyl Alcohol | 30.0 | 6.00 |
| Benzyl Alcohol | 0.9 | 0.18 |
| I3A 'b' | 0.1 | 0.02 |

TABLE 45

Gel premix solution 3

| Component | Concentration w/w | Amount to be Weighed (g) |
|---|---|---|
| Citrate Buffer pH 3.50 | 69.0 | 13.80 |
| Isopropyl Alcohol | 30.0 | 6.00 |

TABLE 45-continued

Gel premix solution 3

| Component | Concentration w/w | Amount to be Weighed (g) |
|---|---|---|
| Benzyl Alcohol | 0.9 | 0.18 |
| I3A 'b' | 0.1 | 0.02 |

TABLE 46

Gel premix solution 4

| Component | Concentration w/w | Amount to be Weighed (g) |
|---|---|---|
| Citrate Buffer pH 4.00 | 69.0 | 13.80 |
| Isopropyl Alcohol | 30.0 | 6.00 |
| Benzyl Alcohol | 0.9 | 0.18 |
| I3A 'b' | 0.1 | 0.02 |

TABLE 47

Gel premix solution 5

| Component | Concentration w/w | Amount to be Weighed (g) |
|---|---|---|
| Citrate Buffer pH 2.75 | 69.09 | 69.09 |
| Isopropyl Alcohol | 30.00 | 30.00 |
| Benzyl Alcohol | 0.90 | 0.90 |
| I3A 'b' | 0.01 | 0.01 |

TABLE 48

Gel premix solution 6

| Component | Concentration w/w | Amount to be Weighed (g) |
|---|---|---|
| Citrate Buffer pH 3.00 | 69.09 | 69.09 |
| Isopropyl Alcohol | 30.00 | 30.00 |
| Benzyl Alcohol | 0.90 | 0.90 |
| I3A 'b' | 0.01 | 0.01 |

TABLE 49

Gel premix solution 7

| Component | Concentration w/w | Amount to be Weighed (g) |
|---|---|---|
| Citrate Buffer pH 3.50 | 69.09 | 69.09 |
| Isopropyl Alcohol | 30.00 | 30.00 |
| Benzyl Alcohol | 0.90 | 0.90 |
| I3A 'b' | 0.01 | 0.01 |

TABLE 50

Gel premix solution 8

| Component | Concentration w/w | Amount to be Weighed (g) |
|---|---|---|
| Citrate Buffer pH 4.00 | 69.09 | 69.09 |
| Isopropyl Alcohol | 30.00 | 30.00 |
| Benzyl Alcohol | 0.90 | 0.90 |
| I3A 'b' | 0.01 | 0.01 |

Stability Testing of Gel Premix Formulations

The gel premix solutions prepared above were placed on stability at 2-8, 25 and 40° C. and were tested at time points T=0 and 2 weeks. At each time point the premix solutions were assessed for I3A 'b' content according the procedure detailed below.

1.1.3 Stability Testing of Gel Premix Formulations

The gel premix solutions prepared wore placed on stability at 2-8, 25 and 40° C. and were tested at time points T=0 and 2 weeks. At each time point the premix solutions were assessed for I3A 'b' content by calculating the percentage HPLC peak area of I3A 'b' relative to the peak areas of the I3A 'b' related substances isoform 'a' and isoform 'c' as described below.

HPLC Instrumentation and Methodology

All samples to be analysed for I3A 'b' were analysed using HPLC Method 2. The instrumentation and chromatographic conditions for HPLC Method 2 are as follows:

Instrumentation:
Waters Alliance 2695 Separations Module plus Autosampler
Waters 996 PDA detector
Empower Software, version 2.00
Chromatographic Conditions:
Column: Symmetry $C_{18}$-5 μm (Waters)
Column length: 150×3.90 mm
Column temperature: 30° C.±2° C.
Guard column: Symmetry $C_{18}$-5 μm (Waters) (PN: WAT054225)
Guard column length: 20×3.90 mm
Mobile phase: 0.02% v/v TFA in Water (A); 0.02% v/v TFA in Acetonitrile (B) A:B, 50:50 (starting composition)
(Gradient, see Table 51 below)
Flow rate: 1.0 ml/min
Autosampler temperature: 8° C.±2+ C.
UV wavelength: 230 nm
Injection volume: 10/40 μl
Run time: 20 mins

TABLE 51

Gradient Table for HPLC Method 2

| Step | Time | Flow | % A | % B | Curve |
|---|---|---|---|---|---|
| 1 | | 1.00 | 50.0 | 50.0 | |
| 2 | 2.00 | 1.00 | 50.0 | 50.0 | 6 |
| 3 | 5.00 | 1.00 | 40.0 | 60.0 | 6 |
| 4 | 12.00 | 1.00 | 20.0 | 80.0 | 6 |
| 5 | 16.00 | 1.00 | 20.0 | 80.0 | 6 |
| 6 | 16.50 | 1.00 | 50.0 | 50.0 | 6 |
| 7 | 20.00 | 1.00 | 50.0 | 50.0 | 6 |

Stability Data for I3A 'b' in Gel Premix Solutions pH Range 2.75 to 4.00 at 2-8, 25 and 40° C. (Mean, n=3)

| Gel Premix # | Storage Temperature (° C.) | Time (weeks) | % Peak Purity of I3A 'b' Relative to I3A 'b', isoform 'a' and isoform 'c' | % Peak Purity of isoform 'a' Relative to I3A 'b', isoform 'c' and isoform 'a' | % Peak Purity of isoform 'c' Relative to isoform 'a', isoform 'c' and I3A 'b' |
|---|---|---|---|---|---|
| 1 | N/A | 0 | 98.98 | 1.02 | 0.00 |
| 2 | N/A | 0 | 98.96 | 1.04 | 0.00 |
| 3 | N/A | 0 | 98.97 | 1.03 | 0.00 |

| Gel Premix # | Storage Temperature (° C.) | Time (weeks) | % Peak Purity of I3A 'b' Relative to I3A 'b', isoform 'a' and isoform 'c' | % Peak Purity of isoform 'a' Relative to I3A 'b', isoform 'c' and isoform 'a' | % Peak Purity of isoform 'c' Relative to isoform 'a', isoform 'c' and I3A 'b' |
|---|---|---|---|---|---|
| 4 | N/A | 0 | 98.91 | 1.09 | 0.00 |
| 5 | N/A | 0 | 99.09 | 0.91 | 0.00 |
| 6 | N/A | 0 | 98.99 | 1.01 | 0.00 |
| 7 | N/A | 0 | 98.99 | 1.01 | 0.00 |
| 8 | N/A | 0 | 99.00 | 1.00 | 0.00 |
| 1 | 2-8 | 2 | 98.77 | 1.23 | 0.00 |
| 2 | 2-8 | 2 | 98.65 | 1.35 | 0.00 |
| 3 | 2-8 | 2 | 98.61 | 1.39 | 0.00 |
| 4 | 2-8 | 2 | 98.50 | 1.50 | 0.00 |
| 5 | 2-8 | 2 | 98.80 | 1.20 | 0.00 |
| 6 | 2-8 | 2 | 98.57 | 1.43 | 0.00 |
| 7 | 2-8 | 2 | 98.44 | 1.56 | 0.00 |
| 8 | 2-8 | 2 | 98.03 | 1.97 | 0.00 |
| 1 | 25 | 2 | 98.69 | 1.31 | 0.00 |
| 2 | 25 | 2 | 98.51 | 1.49 | 0.00 |
| 3 | 25 | 2 | 98.19 | 1.81 | 0.00 |
| 4 | 25 | 2 | 97.42 | 2.58 | 0.00 |
| 5 | 25 | 2 | 98.78 | 1.22 | 0.00 |
| 6 | 25 | 2 | 98.55 | 1.45 | 0.00 |
| 7 | 25 | 2 | 98.39 | 1.61 | 0.00 |
| 8 | 25 | 2 | 97.71 | 2.29 | 0.00 |
| 1 | 40 | 2 | 97.77 | 2.23 | 0.00 |
| 2 | 40 | 2 | 96.99 | 3.01 | 0.00 |
| 3 | 40 | 2 | 96.48 | 3.52 | 0.00 |
| 4 | 40 | 2 | 96.02 | 3.98 | 0.00 |
| 5 | 40 | 2 | 98.09 | 1.91 | 0.00 |
| 6 | 40 | 2 | 97.93 | 2.07 | 0.00 |
| 7 | 40 | 2 | 97.23 | 2.77 | 0.00 |
| 8 | 40 | 2 | 96.43 | 3.57 | 0.00 |

CONCLUSIONS

Storage of all gel premix solutions at 2-8° C. provides the best stability for I3A 'b', based on the higher percentage peak HPLC purity obtained for I3A 'b' compared to the storage of the gel premix solutions at 25 and 40° C.

The two gel premix solutions that provided the best stability for I3A 'b', based on percentage HPLC peak purity, were numbers 1 and 5. These premix solutions contained the citrate buffer at the lowest pH used in the study (pH=2.75).

The two gel premix solutions that provided the least stability for I3A 'b', based on percentage HPLC peak purity, were numbers 4 and 8. These premix solutions contain the citrate buffer at the highest pH used in the study (pH=4.00).

Lowering the temperature and the citrate buffer pH in the gel premix solutions provided the best stability for I3A 'b' where the percentage HPLC peak purity of I3A 'b' was used as an indicator of stability in this study.

REFERENCES

Ho V C, Griffiths C E M, Ellis C N, Gupta A K, McCuaig C C, Nickoloff B J, Cooper K D, Hamilton T A and Voorhees J J. J Am Acad Dermatol 22:94-100, 1999.

Ford J L. Parenteral products In: Pharmaceutics, The Science of dosage form design (Ed M E Aulton), Churchill Livingstone, London, 1988.

Wade A and Weller P J. Handbook of Pharmaceutical Excipients 2$^{nd}$ Edition. American Pharmaceutical Association, Washington, 1994.

Barichello J M, Morishita M, Takayama K and Nagai T, Absorption of insulin from pluronic F-127 gels following subcutaneous administration in rats. Int J Pharm 184:189-198, 1999.

Tobiyama T, Miyazaki S, and Takada M, Use of pluronic F-127 gels as a vehicle for percutaneous absorption. Yakuzaigaku 54:205-213, 1994.

Morikawa K et al., Enhancement of therapeutic effects of recombinant interleukin-2 on a transplantable rat fibrosarcoma by the use of a sustained release vehicle, Pluronic gel. Cancer 47:37-41, 1987

Katakama M et al., Controlled release of human growth hormone in rats following parenteral administration of poloxamer gels. J Control Rel 49:21-26, 1997.

Wasan K M, Subramanian R, Kwong M, Goldberg I J, Wright T and Johnston T P, Poloxamer 407 mediated alternations in the activities of enzymes regulating lipid metabolism in rats. J. Pharm Sci. 6 189-197, 2003.

Powell M F, Nguyen T and Baloian L. Compendium of Excipients for Parenteral Formulations. PDA J Pharm Sci Tech 52:238-311, 1998.

Schmolka I R, Artificial skin I. Preparation and properties of pluronic F-127 gels for the treatment of burns. J. Biomed. Mater. Res., 6, 571-582, 1972.

The invention claimed is:

1. A formulation, comprising:
   ingenol angelate, at least about 95% of the ingenol angelate being ingenol-3-angelate (isoform 'b');
   a penetration enhancer;
   a gelling agent;
   an acidifying agent; and a pharmaceutically acceptable solvent,
   wherein the formulation is a topical formulation and comprises ingenol-3-angelate (isoform 'b') in an amount from 0.001% by weight to 0.15% by weight.

2. The formulation of claim 1, wherein the solvent is selected from the group consisting of polyethylene glycol, methyl ethyl ketone, ethyl acetate, diethyl ether, and benzyl alcohol.

3. The formulation of claim 2, wherein the solvent is benzyl alcohol.

4. The formulation of claim 3, wherein the formulation comprises 0.9% by weight benzyl alcohol.

5. The formulation of claim 1, wherein the formulation has a pH of no greater than 4.5.

6. The formulation of claim 1, wherein the formulation has a pH of no less than 2.5.

7. The formulation of claim 1, wherein ingenol-3-angelate (isoform 'b') is the only active ingredient.

8. The formulation of claim 1, wherein the formulation is selected from the group consisting of a gel, a cream, an ointment, a paint, a lotion, and a foam.

9. The formulation of claim 1, wherein the formulation is suitable for storage at 2-8° C.

10. The formulation of claim 1, wherein the formulation is suitable for storage at 2-8° C. for at least one year.

11. A formulation, comprising:
    ingenol-3-angelate (isoform 'b');
    isopropyl alcohol;
    hydroxyethylcellulose;
    benzyl alcohol;
    an acid buffer comprising citric acid and sodium citrate; and
    water;
    wherein the formulation is a topical formulation and comprises ingenol-3-angelate (isoform 'b') in an amount from 0.001% by weight to 0.15% by weight.

12. The formulation of claim 11, wherein the formulation comprises from 0.01% by weight to 0.1% by weight ingenol-3-angelate (isoform 'b').

13. The formulation of claim 11, wherein the formulation comprises 30% by weight isopropyl alcohol.

14. The formulation of claim 11, wherein the formulation comprises from 1% by weight to 5% by weight hydroxyethylcellulose.

15. The formulation of claim 11, wherein the formulation comprises 0.9% by weight benzyl alcohol.

16. The formulation of claim 11, wherein the formulation comprises from 0.5% by weight to 10% by weight acid buffer.

17. The formulation of claim 11, wherein the formulation comprises:
- from 0.001% by weight to 0.15% by weight ingenol-3-angelate (isoform 'b');
- 30% by weight isopropyl alcohol;
- 1.5% by weight hydroxyethylcellulose;
- 0.9% by weight benzyl alcohol;
- from 0.5% by weight to 10% by weight acid buffer; and
- water.

18. The formulation of claim 11, wherein the formulation has a pH of no greater than 4.5.

19. The formulation of claim 11, wherein the formulation has a pH of no less than 2.5.

20. The formulation of claim 11, wherein ingenol-3-angelate (isoform 'b') is the only active ingredient.

21. The formulation of claim 11, wherein the formulation is selected from the group consisting of a gel, a cream, an ointment, a paint, a lotion, and a foam.

22. The formulation of claim 11, wherein the formulation is suitable for storage at 2-8° C.

23. The formulation of claim 11, wherein the formulation is suitable for storage at 2-8° C. for at least one year.

24. The formulation of claim 1, wherein at least about 99% of the ingenol angelate is ingenol-3-angelate (isoform 'b').

* * * * *